(12) United States Patent
Mueller et al.

(10) Patent No.: US 10,927,399 B2
(45) Date of Patent: Feb. 23, 2021

(54) ACETYL-COA PRODUCING ENZYMES IN YEAST

(71) Applicant: DSM IP ASSETS B.V., Heerlen (NL)

(72) Inventors: Ulrike Maria Mueller, Linnich (DE); Liang Wu, Delft (NL); Lourina Madeleine Raamsdonk, Nootdorp (NL); Aaron Adriaan Winkler, The Hague (NL)

(73) Assignee: DSM IP ASSETS B.V., Heerlen (NL)

( * ) Notice: Subject to any disclaimer, the term of this patent is extended or adjusted under 35 U.S.C. 154(b) by 218 days.

(21) Appl. No.: 14/045,683

(22) Filed: Oct. 3, 2013

(65) Prior Publication Data

US 2014/0030730 A1 Jan. 30, 2014

Related U.S. Application Data

(63) Continuation of application No. 12/670,050, filed as application No. PCT/EP2008/059119 on Jul. 11, 2008, now abandoned.

(60) Provisional application No. 60/935,031, filed on Jul. 23, 2007, provisional application No. 61/064,120, filed on Feb. 19, 2008.

(30) Foreign Application Priority Data

| Jul. 23, 2007 | (EP) | 07112956 |
| Dec. 21, 2007 | (EP) | 07123976 |
| Feb. 19, 2008 | (EP) | 08101747 |

(51) Int. Cl.

| C12N 1/16 | (2006.01) |
| C12N 9/04 | (2006.01) |
| C12Q 1/32 | (2006.01) |
| C07K 14/33 | (2006.01) |
| C12N 9/02 | (2006.01) |
| C12P 7/16 | (2006.01) |

(52) U.S. Cl.
CPC .............. *C12Q 1/32* (2013.01); *C07K 14/33* (2013.01); *C12N 9/001* (2013.01); *C12P 7/16* (2013.01); *Y02E 50/10* (2013.01)

(58) Field of Classification Search
None
See application file for complete search history.

(56) References Cited

U.S. PATENT DOCUMENTS

| 6,610,836 B1 | 8/2003 | Breton et al. |
| 7,927,861 B2 | 4/2011 | Mills et al. |
| 2003/0104523 A1* | 6/2003 | Bauer ............... C07K 14/705 435/69.1 |
| 2004/0235060 A1* | 11/2004 | Dhanasekaran et al. ...... 435/7.2 |
| 2005/0059136 A1 | 3/2005 | van Maris et al. |
| 2005/0153411 A1 | 7/2005 | Wahlbom et al. |
| 2006/0078901 A1 | 4/2006 | Buchrieser et al. |
| 2008/0182308 A1* | 7/2008 | Donaldson ........... C12N 9/0004 435/160 |
| 2009/0155869 A1* | 6/2009 | Buelter ................. C12N 15/52 435/160 |
| 2010/0159546 A1 | 6/2010 | Aristidou et al. |

FOREIGN PATENT DOCUMENTS

| WO | 02077183 | 10/2002 |
| WO | 2007041269 | 4/2007 |
| WO | 2008080124 | 7/2008 |
| WO | 2008121701 | 10/2008 |

OTHER PUBLICATIONS

SEQ ID No. 51 Alignment (2015) pp. 1-7.*
SEQ ID No. 52 Alignment (2015) pp. 1-3.*
NCBI Q99X67 (2006) "Alcohol-acetaldehyde dehydrogenase" pp. 1-2.*
SEQ alignment (2013) SCORE result for instant SEQ ID No. 52, pp. 1-2.
DNA SEQ alignment (2013) SCORE result for instant SEQ ID No. 51, pp. 1-3.
Boxma et al. (2004) The anaerobic chytridiomycete fungus *Piromyces* sp. E2 produces ethanol via pyruvate:formate lyase and an alcohol dehydrogenase E, Mot. Microbiol., vol. 51, No. 5, pp. 1389-1399.
Remize et al. (2000) Engineering of the Pyruvate Dehydrogenase Bypass in *Saccharomyces cerevisiae*: Role of the Cytosolic Mg21 and Mitochondrial K1 Acetaldehyde Dehydrogenases Ald6p and Ald4p in Acetate Formation during Alcoholic Fermentation, Appl. Environ. Microbiol., vol. 66, No. 8, pp. 3151-3159.

(Continued)

*Primary Examiner* — Manjunath N Rao
*Assistant Examiner* — Samuel W Liu
(74) *Attorney, Agent, or Firm* — McBee Moore & Vanik IP, LLC

(57) ABSTRACT

The present invention relates to a method of identifying a heterologous polypeptide having enzymatic activity for converting pyruvate, acetaldehyde or acetate into acetyl-CoA in (the cytosol of) a yeast cell comprising: a) providing a mutated yeast cell comprising a deletion of at least one gene of the (PDH) by-pass, selected from the genes encoding the enzymes pyruvate decarboxylase (PDC), acetaldehyde dehydrogenase (ALD), and acetyl-CoA synthetase (ACS); b) transforming said mutated yeast cell with an expression vector comprising a heterologous nucleotide sequence encoding a candidate polypeptide having potential enzymatic activity for converting pyruvate, acetaldehyde or acetate into acetyl-CoA; c) testing said recombinant mutated yeast cell for its ability to grow on minimal medium containing glucose as sole carbon source, and d) identifying said candidate polypeptide as a heterologous polypeptide having enzymatic activity for converting pyruvate, acetaldehyde or acetate into acetyl-CoA in (the cytosol of) said yeast cell when growth of said cell is observed. The invention further relates to a method of producing a fermentation production such as butanol.

15 Claims, 4 Drawing Sheets

Specification includes a Sequence Listing.

(56) References Cited

OTHER PUBLICATIONS

Boubekeur et al. (1999) A Mitochondrial Pyruvate Dehydrogenase Bypass in the Yeast *Saccharomyces cerevisiae*, J. Biol. Chem., vol. 274, No. 30, pp. 21044-21048.
Database USPTO Proteins [Online], Accession No. AAR49390, "Sequence 9107 form U.S. Pat. No. 6,610,836", Dec. 2003), 1 page.
Database Geneseq [Online], Accession No. ABB47983, "Listeria monocytogenes protein #687", (Feb. 5, 2002), 2 pages.
Database EPO Proteins [Online], Accession No. AX639358, "Sequence 548 from Patent W00101118", (Feb. 21, 2003), 1 page.
Database Geneseq [Online], Accession No. ABB48178, "Listeria monocytogenes protein #882", (Feb. 5, 2002), 2 pages.
Database Geneseq [Online], Accession No. ABU16560, "Protein encoded by Prokaryotic essential gene #2087", (Jun. 19, 2003), 2 pages.
Database Geneseq [Online], Accession No. ABU25371, "Protein encoded by Prokaryotic essential gene #10898", (Jun. 19, 2003), 2 pages.
Blomqvist, K. et al., "Chromosomal Integration and Expression of Two Bacterial a-Acetolactate Decarboxylase Genes in Brewer's Yeast", Applied and Environmental Microbiology, (Oct. 1991), pp. 2796-2803.
Saint-Prix, F. et al., "Functional analysis of the ALD gene family of *Saccharomyces cerevisiae* during anaerobic growth on glucose: the NADP+-dependent Ald6p and Ald5p isoforms play a major role in acetate formation", Microbiology, vol. 150, (2004), pp. 2209-2220.
Hwang, Wen-Zhe et al, "Expression of a Bacterial Ice Nucleation Gene in a Yeast *Saccaromyces cerevisiae* and Its Possible Application in Food Freezing Processes", J. Agric. Food Chem., vol. 49, (2001), pp. 4662-4666.
Flikweert, M. et al., "Pyruvate Dacarboxylase: An Indispensable Enzyme for Growth of *Saccaromyces cerevisiae* on Glucose", Yeast, vol. 12, (1996), pp. 247-257.
Boxma, B. et al, "The anaerobic chytridiomycete fungus *Piromyces* sp. E2 produces ethanol via pyruvate: formate lyase and an alcohol dehydrogenase E", Molecular Microbiology, vol. 51, No. 5, (2004), pp. 1389-1399.
International Search Report for PCTIEP2008/059119, dated Mar. 6, 2009.
BioCyc (2013, update) Lactococcus lactis lactis 111403 EC 1.2.1.10—acetaldehyde dehydrogenase (acetylating), pp. 1-3.
Van Den Berg et al., "ACS2, a *Saccharomyces cerevisiae* gene encoding acetyl-coenzyme A synthetase, essential for growth on glucose." Eur. J. Biochem. 231,704-713 (1995).
Manjasetty et al., "Crystal structure of a bifunctional aldolase-dehydrogenase: Sequestering a reactive and volatile intermediate." PNAS, Jun. 10, 2003, vol. 100, No. 12, 6992-6997.

\* cited by examiner

SEQUENCE LISTING

```
<160> NUMBER OF SEQ ID NOS: 52

<210> SEQ ID NO 1
<211> LENGTH: 64
<212> TYPE: DNA
<213> ORGANISM: Artificial
<220> FEATURE:
<223> OTHER INFORMATION: primer 5'acs2

<400> SEQUENCE: 1
atacacaaac agaatacagg aaagtaaatc aatacaataa taaaacagct gaagcttcgt      60
acgc                                                                   64

<210> SEQ ID NO 2
<211> LENGTH: 67
<212> TYPE: DNA
<213> ORGANISM: Artificial
<220> FEATURE:
<223> OTHER INFORMATION: primer 3'acs2

<400> SEQUENCE: 2
tctcattacg aaattttct catttaagtt atttcttttt ttgaggcata ggccactagt      60
ggatctg                                                                67

<210> SEQ ID NO 3
<211> LENGTH: 20
<212> TYPE: DNA
```

```
<213> ORGANISM: Artificial
<220> FEATURE:
<223> OTHER INFORMATION: probe 5'acs2

<400> SEQUENCE: 3
gatattcggt agccgattcc                                               20

<210> SEQ ID NO 4
<211> LENGTH: 20
<212> TYPE: DNA
<213> ORGANISM: Artificial
<220> FEATURE:
<223> OTHER INFORMATION: probe 3'acs2

<400> SEQUENCE: 4
ccgtaacctt ctcgtaatgc                                               20

<210> SEQ ID NO 5
<211> LENGTH: 20
<212> TYPE: DNA
<213> ORGANISM: Artificial
<220> FEATURE:
<223> OTHER INFORMATION: probe ACS2internal

<400> SEQUENCE: 5
cggattcgtc atcagcttca                                               20

<210> SEQ ID NO 6
<211> LENGTH: 20
<212> TYPE: DNA
<213> ORGANISM: Artificial
<220> FEATURE:
<223> OTHER INFORMATION: probe KanA

<400> SEQUENCE: 6
cgcacgtcaa gactgtcaag                                               20

<210> SEQ ID NO 7
<211> LENGTH: 20
<212> TYPE: DNA
<213> ORGANISM: Artificial
<220> FEATURE:
<223> OTHER INFORMATION: probe KanB

<400> SEQUENCE: 7
tcgtatgtga atgctggtcg                                               20

<210> SEQ ID NO 8
<211> LENGTH: 64
<212> TYPE: DNA
<213> ORGANISM: Artificial
<220> FEATURE:
<223> OTHER INFORMATION: primer MCS-5'Tadh

<400> SEQUENCE: 8
aaggtacctc tagactagtc ccgggctgca gtcgactcga gcgaatttct tatgatttat   60
gatt                                                                64

<210> SEQ ID NO 9
<211> LENGTH: 39
<212> TYPE: DNA
<213> ORGANISM: Artificial
<220> FEATURE:
<223> OTHER INFORMATION: primer Tadh1-Hind

<400> SEQUENCE: 9
```
aggaagctta ggcctgtgtg gaagaacgat tacaacagg                    39

<210> SEQ ID NO 10
<211> LENGTH: 24
<212> TYPE: DNA
<213> ORGANISM: Artificial
<220> FEATURE:
<223> OTHER INFORMATION: primer P1

<400> SEQUENCE: 10
gaattgaagg atatctacat caag                                    24

<210> SEQ ID NO 11
<211> LENGTH: 25
<212> TYPE: DNA
<213> ORGANISM: Artificial
<220> FEATURE:
<223> OTHER INFORMATION: primer P2

<400> SEQUENCE: 11
cccatctacg gaaccctgat caagc                                   25

<210> SEQ ID NO 12
<211> LENGTH: 26
<212> TYPE: DNA
<213> ORGANISM: Artificial
<220> FEATURE:
<223> OTHER INFORMATION: primer P3

<400> SEQUENCE: 12
gatggtgtca ccattaccag gtctag                                  26

<210> SEQ ID NO 13
<211> LENGTH: 56
<212> TYPE: DNA
<213> ORGANISM: Artificial
<220> FEATURE:
<223> OTHER INFORMATION: Primer P4

<400> SEQUENCE: 13
gttctctggt caagttgaag tccattttga ttgatttgac tgtgttattt tgcgtg    56

<210> SEQ ID NO 14
<211> LENGTH: 25
<212> TYPE: DNA
<213> ORGANISM: Artificial
<220> FEATURE:
<223> OTHER INFORMATION: Primer P5

<400> SEQUENCE: 14
gaacaataga gcgaccatga ccttg                                   25

<210> SEQ ID NO 15
<211> LENGTH: 25
<212> TYPE: DNA
<213> ORGANISM: Artificial
<220> FEATURE:
<223> OTHER INFORMATION: Primer P6

<400> SEQUENCE: 15
gacatcagcg tcaccagcct tgatg                                   25

<210> SEQ ID NO 16
<211> LENGTH: 27
<212> TYPE: DNA

<213> ORGANISM: Artificial
<220> FEATURE:
<223> OTHER INFORMATION: Primer P7

<400> SEQUENCE: 16
gattgaaggt ttcaagaaca ggtgatg                                    27

<210> SEQ ID NO 17
<211> LENGTH: 25
<212> TYPE: DNA
<213> ORGANISM: Artificial
<220> FEATURE:
<223> OTHER INFORMATION: Primer P8

<400> SEQUENCE: 17
ggcgatcaga gttgaaaaaa aaatg                                      25

<210> SEQ ID NO 18
<211> LENGTH: 1404
<212> TYPE: DNA
<213> ORGANISM: Escherichia coli
<220> FEATURE:
<221> NAME/KEY: CDS
<222> LOCATION: (1)..(1404)

<400> SEQUENCE: 18

| | | | | | | | | | | | | | | | | |
|---|---|---|---|---|---|---|---|---|---|---|---|---|---|---|---|---|---|
| atg | aat | caa | cag | gat | att | gaa | cag | gtg | gtg | aaa | gcg | gta | ctg | ctg | aaa | | 48 |
| Met | Asn | Gln | Gln | Asp | Ile | Glu | Gln | Val | Val | Lys | Ala | Val | Leu | Leu | Lys | | |
| 1 | | | | 5 | | | | | 10 | | | | | 15 | | | |

| | | | | | | | | | | | | | | | | |
|---|---|---|---|---|---|---|---|---|---|---|---|---|---|---|---|---|
| atg | caa | agc | agt | gac | acg | ccg | tcc | gcc | gcc | gtt | cat | gag | atg | ggc | gtt | 96 |
| Met | Gln | Ser | Ser | Asp | Thr | Pro | Ser | Ala | Ala | Val | His | Glu | Met | Gly | Val | |
| | | | 20 | | | | | 25 | | | | | 30 | | | |

| | | | | | | | | | | | | | | | | |
|---|---|---|---|---|---|---|---|---|---|---|---|---|---|---|---|---|
| ttc | gcg | tcc | ctg | gat | gac | gcc | gtt | gcg | gca | gcc | aaa | gtc | gcc | cag | caa | 144 |
| Phe | Ala | Ser | Leu | Asp | Asp | Ala | Val | Ala | Ala | Ala | Lys | Val | Ala | Gln | Gln | |
| | | 35 | | | | | 40 | | | | | 45 | | | | |

| | | | | | | | | | | | | | | | | |
|---|---|---|---|---|---|---|---|---|---|---|---|---|---|---|---|---|
| ggg | tta | aaa | agc | gtg | gca | atg | cgc | cag | tta | gcc | att | gct | gcc | att | cgt | 192 |
| Gly | Leu | Lys | Ser | Val | Ala | Met | Arg | Gln | Leu | Ala | Ile | Ala | Ala | Ile | Arg | |
| | 50 | | | | | 55 | | | | | 60 | | | | | |

| | | | | | | | | | | | | | | | | |
|---|---|---|---|---|---|---|---|---|---|---|---|---|---|---|---|---|
| gaa | gca | ggc | gaa | aaa | cac | gcc | aga | gat | tta | gcg | gaa | ctt | gcc | gtc | agt | 240 |
| Glu | Ala | Gly | Glu | Lys | His | Ala | Arg | Asp | Leu | Ala | Glu | Leu | Ala | Val | Ser | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gaa | acc | ggc | atg | ggg | cgc | gtt | gaa | gat | aaa | ttt | gca | aaa | aac | gtc | gct | 288 |
| Glu | Thr | Gly | Met | Gly | Arg | Val | Glu | Asp | Lys | Phe | Ala | Lys | Asn | Val | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| cag | gcg | cgc | ggc | aca | cca | ggc | gtt | gag | tgc | ctc | tct | ccg | caa | gtg | ctg | 336 |
| Gln | Ala | Arg | Gly | Thr | Pro | Gly | Val | Glu | Cys | Leu | Ser | Pro | Gln | Val | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| act | ggc | gac | aac | ggc | ctg | acc | cta | att | gaa | aac | gca | ccc | tgg | ggc | gtg | 384 |
| Thr | Gly | Asp | Asn | Gly | Leu | Thr | Leu | Ile | Glu | Asn | Ala | Pro | Trp | Gly | Val | |
| | | 115 | | | | | 120 | | | | | 125 | | | | |

| | | | | | | | | | | | | | | | | |
|---|---|---|---|---|---|---|---|---|---|---|---|---|---|---|---|---|
| gtg | gct | tcg | gtg | acg | cct | tcc | act | aac | ccg | gcg | gca | acc | gta | att | aac | 432 |
| Val | Ala | Ser | Val | Thr | Pro | Ser | Thr | Asn | Pro | Ala | Ala | Thr | Val | Ile | Asn | |
| | 130 | | | | | 135 | | | | | 140 | | | | | |

| | | | | | | | | | | | | | | | | |
|---|---|---|---|---|---|---|---|---|---|---|---|---|---|---|---|---|
| aac | gcc | atc | agc | ctg | att | gcc | gcg | ggc | aac | agc | gtc | att | ttt | gcc | ccg | 480 |
| Asn | Ala | Ile | Ser | Leu | Ile | Ala | Ala | Gly | Asn | Ser | Val | Ile | Phe | Ala | Pro | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cat | ccg | gcg | gcg | aaa | aaa | gtc | tcc | cag | cgg | gcg | att | acg | ctg | ctc | aac | 528 |
| His | Pro | Ala | Ala | Lys | Lys | Val | Ser | Gln | Arg | Ala | Ile | Thr | Leu | Leu | Asn | |
| | | | | 165 | | | | | 170 | | | | | 175 | | |

| | | | | | | | | | | | | | | | | |
|---|---|---|---|---|---|---|---|---|---|---|---|---|---|---|---|---|
| cag | gcg | att | gtt | gcc | gca | ggt | ggg | ccg | gaa | aac | tta | ctg | gtt | act | gtg | 576 |
| Gln | Ala | Ile | Val | Ala | Ala | Gly | Gly | Pro | Glu | Asn | Leu | Leu | Val | Thr | Val | |
| | | | 180 | | | | | 185 | | | | | 190 | | | |

```
gca aat ccg gat atc gaa acc gcg caa cgc ttg ttc aag ttt ccg ggt      624
Ala Asn Pro Asp Ile Glu Thr Ala Gln Arg Leu Phe Lys Phe Pro Gly
        195                 200                 205 atc ggc ctg ctg gtg gta acc ggc ggc gaa gcg gta gta gaa gcg gcg      672
Ile Gly Leu Leu Val Val Thr Gly Gly Glu Ala Val Val Glu Ala Ala
    210                 215                 220 cgt aaa cac acc aat aaa cgt ctg att gcc gca ggc gct ggc aac ccg      720
Arg Lys His Thr Asn Lys Arg Leu Ile Ala Ala Gly Ala Gly Asn Pro
225                 230                 235                 240 ccg gta gtg gtg gat gaa acc gcc gac ctc gcc cgt gcc gct cag tcc      768
Pro Val Val Val Asp Glu Thr Ala Asp Leu Ala Arg Ala Ala Gln Ser
                245                 250                 255 atc gtc aaa ggc gct tct ttc gat aac aac atc att tgt gcc gac gaa      816
Ile Val Lys Gly Ala Ser Phe Asp Asn Asn Ile Ile Cys Ala Asp Glu
            260                 265                 270 aag gta ctg att gtt gtt gat agc gta gcc gat gaa ctg atg cgt ctg      864
Lys Val Leu Ile Val Val Asp Ser Val Ala Asp Glu Leu Met Arg Leu
        275                 280                 285 atg gaa ggc cag cac gcg gtg aaa ctg acc gca gaa cag gcg cag cag      912
Met Glu Gly Gln His Ala Val Lys Leu Thr Ala Glu Gln Ala Gln Gln
    290                 295                 300 ctg caa ccg gtg ttg ctg aaa aat atc gac gag cgc gga aaa ggc acc      960
Leu Gln Pro Val Leu Leu Lys Asn Ile Asp Glu Arg Gly Lys Gly Thr
305                 310                 315                 320 gtc agc cgt gac tgg gtt ggt cgc gac gca ggc aaa atc gcg gcg gca     1008
Val Ser Arg Asp Trp Val Gly Arg Asp Ala Gly Lys Ile Ala Ala Ala
                325                 330                 335 atc ggc ctt aaa gtt ccg caa gaa acg cgc ctg ctg ttt gtg gaa acc     1056
Ile Gly Leu Lys Val Pro Gln Glu Thr Arg Leu Leu Phe Val Glu Thr
            340                 345                 350 acc gca gaa cat ccg ttt gcc gtg act gaa ctg atg atg ccg gtg ttg     1104
Thr Ala Glu His Pro Phe Ala Val Thr Glu Leu Met Met Pro Val Leu
        355                 360                 365 ccc gtc gtg cgc gtc gcc aac gtg gcg gat gcc att gcg cta gcg gtg     1152
Pro Val Val Arg Val Ala Asn Val Ala Asp Ala Ile Ala Leu Ala Val
    370                 375                 380 aaa ctg gaa ggc ggt tgc cac cac acg gcg gca atg cac tcg cgc aac     1200
Lys Leu Glu Gly Gly Cys His His Thr Ala Ala Met His Ser Arg Asn
385                 390                 395                 400 atc gaa aac atg aac cag atg gcg aat gct att gat acc agc att ttc     1248
Ile Glu Asn Met Asn Gln Met Ala Asn Ala Ile Asp Thr Ser Ile Phe
                405                 410                 415 gtt aag aac gga ccg tgc att gcc ggg ctg ggg ctg gcg ggg gaa ggc     1296
Val Lys Asn Gly Pro Cys Ile Ala Gly Leu Gly Leu Ala Gly Glu Gly
            420                 425                 430 tgg acc acc atg acc atc acc acg cca acc ggt gaa ggg gta acc agc     1344
Trp Thr Thr Met Thr Ile Thr Thr Pro Thr Gly Glu Gly Val Thr Ser
        435                 440                 445 gcg cgt acg ttt gtc cgt ctg cgt cgc tgt gta tta gtc gat gcg ttt     1392
Ala Arg Thr Phe Val Arg Leu Arg Arg Cys Val Leu Val Asp Ala Phe
    450                 455                 460 cgc att gtt taa                                                     1404
Arg Ile Val
465

<210> SEQ ID NO 19
<211> LENGTH: 467
<212> TYPE: PRT
<213> ORGANISM: Escherichia coli

<400> SEQUENCE: 19
```

```
Met Asn Gln Gln Asp Ile Glu Gln Val Val Lys Ala Val Leu Leu Lys
1               5                   10                  15

Met Gln Ser Ser Asp Thr Pro Ser Ala Ala Val His Glu Met Gly Val
            20                  25                  30

Phe Ala Ser Leu Asp Asp Ala Val Ala Ala Lys Val Ala Gln Gln
            35                  40                  45

Gly Leu Lys Ser Val Ala Met Arg Gln Leu Ala Ile Ala Ala Ile Arg
50                      55                  60

Glu Ala Gly Glu Lys His Ala Arg Asp Leu Ala Glu Leu Ala Val Ser
65                  70                  75                  80

Glu Thr Gly Met Gly Arg Val Glu Asp Lys Phe Ala Lys Asn Val Ala
                85                  90                  95

Gln Ala Arg Gly Thr Pro Gly Val Glu Cys Leu Ser Pro Gln Val Leu
            100                 105                 110

Thr Gly Asp Asn Gly Leu Thr Leu Ile Glu Asn Ala Pro Trp Gly Val
            115                 120                 125

Val Ala Ser Val Thr Pro Ser Thr Asn Pro Ala Ala Thr Val Ile Asn
        130                 135                 140

Asn Ala Ile Ser Leu Ile Ala Ala Gly Asn Ser Val Ile Phe Ala Pro
145                 150                 155                 160

His Pro Ala Ala Lys Lys Val Ser Gln Arg Ala Ile Thr Leu Leu Asn
                165                 170                 175

Gln Ala Ile Val Ala Ala Gly Gly Pro Glu Asn Leu Leu Val Thr Val
            180                 185                 190

Ala Asn Pro Asp Ile Glu Thr Ala Gln Arg Leu Phe Lys Phe Pro Gly
        195                 200                 205

Ile Gly Leu Leu Val Val Thr Gly Gly Glu Ala Val Val Glu Ala Ala
210                 215                 220

Arg Lys His Thr Asn Lys Arg Leu Ile Ala Ala Gly Ala Gly Asn Pro
225                 230                 235                 240

Pro Val Val Val Asp Glu Thr Ala Asp Leu Ala Arg Ala Ala Gln Ser
            245                 250                 255

Ile Val Lys Gly Ala Ser Phe Asp Asn Asn Ile Ile Cys Ala Asp Glu
            260                 265                 270

Lys Val Leu Ile Val Val Asp Ser Val Ala Asp Glu Leu Met Arg Leu
        275                 280                 285

Met Glu Gly Gln His Ala Val Lys Leu Thr Ala Glu Gln Ala Gln Gln
290                 295                 300

Leu Gln Pro Val Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
            325                 330                 335

Ile Gly Leu Lys Val Pro Gln Glu Thr Arg Leu Leu Phe Val Glu Thr
            340                 345                 350

Thr Ala Glu His Pro Phe Ala Val Thr Glu Leu Met Met Pro Val Leu
            355                 360                 365

Pro Val Val Arg Val Ala Asn Val Ala Asp Ala Ile Ala Leu Ala Val
        370                 375                 380

Lys Leu Glu Gly Gly Cys His His Thr Ala Ala Met His Ser Arg Asn
385                 390                 395                 400

Ile Glu Asn Met Asn Gln Met Ala Asn Ala Ile Asp Thr Ser Ile Phe
            405                 410                 415
```

```
Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
        435                 440                 445

Ala Arg Thr Phe Val Arg Leu Arg Arg Cys Val Leu Val Asp Ala Phe
    450                 455                 460

Arg Ile Val
465

<210> SEQ ID NO 20
<211> LENGTH: 1401
<212> TYPE: DNA
<213> ORGANISM: Artificial
<220> FEATURE:
<223> OTHER INFORMATION: optimised sequence

<400> SEQUENCE: 20
```

| | | | | | |
|---|---|---|---|---|---|
| atgaaccaac | aagatatcga | acaagttgtc | aaggctgtct | tgttgaaaat | gcaatcttct | 60 |
| gacactccat | ctgctgctgt | ccacgaaatg | ggtgttttcg | cttctttgga | cgacgctgtt | 120 |
| gctgctgcca | aggttgctca | acaaggtttg | aaatctgttg | ccatgagaca | attggccatt | 180 |
| gctgccatca | gagaagctgg | tgaaaagcat | gccagagact | ggctgaatt | ggctgtctcc | 240 |
| gaaaccggta | tgggtagagt | tgaagacaaa | ttcgctaaga | acgttgctca | agctagaggt | 300 |
| actccaggtg | tcgaatgttt | gtctccacaa | gtcttgaccg | tgataatgg | tttgactttg | 360 |
| attgaaaatg | ctccatgggg | tgttgttgct | tccgtcaccc | catctaccaa | cccagctgct | 420 |
| actgtcatca | caacgccat | ctctttgatt | gctgctggta | actccgttat | cttcgctcca | 480 |
| cacccagctg | ccaagaaggt | ttctcaaaga | gccatcactc | tattgaacca | agccattgtt | 540 |
| gctgctggtg | tccagaaaaa | cttgttggtc | actgttgcca | acccagatat | cgaaactgct | 600 |
| caaagattat | tcaagttccc | aggtatcggt | ctattagtcg | tcactggtgg | tgaagctgtt | 660 |
| gttgaagctg | ccagaaagca | caccaacaag | agattgattg | ctgctggtgc | tggtaaccct | 720 |
| cctgttgttg | tcgatgaaac | cgctgatttg | gccagagctg | ctcaatccat | tgtcaagggt | 780 |
| gcttcttccg | acaacaacat | catctgtgct | gacgaaaagg | ttttgattgt | tgttgactcc | 840 |
| gttgctgacg | aattgatgag | attgatggaa | ggtcaacatg | ccgtcaagtt | gactgctgaa | 900 |
| caagctcaac | aattgcaacc | agttttgttg | aagaacatcg | atgaaagagg | taagggtacc | 960 |
| gtctccagag | actgggttgg | tagagatgct | ggtaagattg | ctgctgccat | cggtttgaag | 1020 |
| gttccacaag | aaaccagatt | attattcgtc | gaaaccaccg | ctgaacaccc | atttgctgtc | 1080 |
| actgaattga | tgatgccagt | cttaccagtt | gtccgtgttg | ctaacgttgc | tgacgctatt | 1140 |
| gctttggctg | tcaaattgga | aggtggttgt | caccacactg | ctgccatgca | ctccagaaac | 1200 |
| atcgaaaaca | tgaaccaaat | ggctaacgcc | attgacactt | ccatctttgt | caagaacggt | 1260 |
| ccatgtatcg | ctggtttggg | tttgggtggt | gaaggttgga | ccaccatgac | catcaccacc | 1320 |
| ccaactggtg | aaggtgtcac | ttctgccaga | actttcgtca | gattacgtcg | ttgtgttttg | 1380 |
| gtcgatgctt | tcagaattgt | t | | | | 1401 |

```
<210> SEQ ID NO 21
<211> LENGTH: 1410
<212> TYPE: DNA
<213> ORGANISM: Listeria innocua
<220> FEATURE:
<221> NAME/KEY: CDS
<222> LOCATION: (1)..(1410)
```

<400> SEQUENCE: 21

```
atg gaa tca tta gaa ctc gaa caa ctg gta aaa aaa gtt ctc tta gaa       48
Met Glu Ser Leu Glu Leu Glu Gln Leu Val Lys Lys Val Leu Leu Glu
1               5                   10                  15 aaa tta gca gaa caa aaa gaa gta cca aca aaa aca act aca caa ggc       96
Lys Leu Ala Glu Gln Lys Glu Val Pro Thr Lys Thr Thr Thr Gln Gly
            20                  25                  30 gcg aaa agt ggc gtt ttt gat aca gtt gac gag gct gtt caa gca gca      144
Ala Lys Ser Gly Val Phe Asp Thr Val Asp Glu Ala Val Gln Ala Ala
        35                  40                  45 gtt ata gcg cag aat tgc tat aaa gaa aaa tca ctt gaa gaa cgc cgc      192
Val Ile Ala Gln Asn Cys Tyr Lys Glu Lys Ser Leu Glu Glu Arg Arg
50                  55                  60 aat gtt gta aaa gca att cgt gaa gca ctt tat cca gaa att gaa aca      240
Asn Val Val Lys Ala Ile Arg Glu Ala Leu Tyr Pro Glu Ile Glu Thr
65                  70                  75                  80 att gcg aca aga gca gtt gca gag act ggt atg gga aat gtg aca gat      288
Ile Ala Thr Arg Ala Val Ala Glu Thr Gly Met Gly Asn Val Thr Asp
                85                  90                  95 aaa att ttg aaa aac acg tta gca atc gaa aaa acg cca ggg gta gaa      336
Lys Ile Leu Lys Asn Thr Leu Ala Ile Glu Lys Thr Pro Gly Val Glu
            100                 105                 110 gat tta tat aca gaa gta gct aca ggt gat aac ggt atg aca cta tat      384
Asp Leu Tyr Thr Glu Val Ala Thr Gly Asp Asn Gly Met Thr Leu Tyr
        115                 120                 125 gaa ctc tct ccg tat ggc gta att ggt gca gta gcg ccg agc aca aac      432
Glu Leu Ser Pro Tyr Gly Val Ile Gly Ala Val Ala Pro Ser Thr Asn
130                 135                 140 cca acg gaa aca ttg att tgt aat tca atc ggt atg ctc gca gct gga      480
Pro Thr Glu Thr Leu Ile Cys Asn Ser Ile Gly Met Leu Ala Ala Gly
145                 150                 155                 160 aat gcc gtt ttt tat agc cct cat cca ggg gca aaa aac att tca ctg      528
Asn Ala Val Phe Tyr Ser Pro His Pro Gly Ala Lys Asn Ile Ser Leu
                165                 170                 175 tgg ttg att gaa aaa cta aac aca att gtt cgc gat agt tgt ggt ata      576
Trp Leu Ile Glu Lys Leu Asn Thr Ile Val Arg Asp Ser Cys Gly Ile
            180                 185                 190 gat aat cta att gtc acc gtg gct aaa cca tcc atc caa gca gct caa      624
Asp Asn Leu Ile Val Thr Val Ala Lys Pro Ser Ile Gln Ala Ala Gln
        195                 200                 205 gaa atg atg aac cat cca aaa gta ccg cta ctt gtt att aca ggt ggt      672
Glu Met Met Asn His Pro Lys Val Pro Leu Leu Val Ile Thr Gly Gly
210                 215                 220 ccg ggc gtt gtt ctc caa gcg atg caa tca ggt aaa aaa gtg att gga      720
Pro Gly Val Val Leu Gln Ala Met Gln Ser Gly Lys Lys Val Ile Gly
225                 230                 235                 240 gca gga gca ggg aac ccg cct tct att gtt gac gaa aca gct aat atc      768
Ala Gly Ala Gly Asn Pro Pro Ser Ile Val Asp Glu Thr Ala Asn Ile
                245                 250                 255 gaa aaa gcg gct gct gac atc gta gac gga gca tct ttt gac cat aat      816
Glu Lys Ala Ala Ala Asp Ile Val Asp Gly Ala Ser Phe Asp His Asn
            260                 265                 270 att tta tgt att gct gaa aaa agt gtg gta gct gtt gat agc att gct      864
Ile Leu Cys Ile Ala Glu Lys Ser Val Val Ala Val Asp Ser Ile Ala
        275                 280                 285 gat ttc ttg tta ttc caa atg gaa aaa aat ggt gcc ctt cat gtt act      912
Asp Phe Leu Leu Phe Gln Met Glu Lys Asn Gly Ala Leu His Val Thr
290                 295                 300 aat cca agt gat att caa aaa tta gaa aaa gta gcc gtt acc gat aaa      960
```

```
Asn Pro Ser Asp Ile Gln Lys Leu Glu Lys Val Ala Val Thr Asp Lys
305                 310                 315                 320 ggt gta act aat aaa aaa tta gtc gga aaa agt gca act gaa atc tta        1008
Gly Val Thr Asn Lys Lys Leu Val Gly Lys Ser Ala Thr Glu Ile Leu
                325                 330                 335 aaa gaa gca gga ata gct tgt gat ttt aca cca cgt tta atc att gtg        1056
Lys Glu Ala Gly Ile Ala Cys Asp Phe Thr Pro Arg Leu Ile Ile Val
                340                 345                 350 gaa acg gag aaa tct cat cca ttt gca aca gta gag cta tta atg cca        1104
Glu Thr Glu Lys Ser His Pro Phe Ala Thr Val Glu Leu Leu Met Pro
            355                 360                 365 atc gtt cca gtt gta agg gtg cct gat ttt gac gaa gcc ctt gaa gtg        1152
Ile Val Pro Val Val Arg Val Pro Asp Phe Asp Glu Ala Leu Glu Val
370                 375                 380 gct att gaa ctc gaa caa ggc tta cat cat aca gca aca atg cat tca        1200
Ala Ile Glu Leu Glu Gln Gly Leu His His Thr Ala Thr Met His Ser
385                 390                 395                 400 caa aat atc tcg aga tta aac aaa gct gca aga gat atg caa act tcc        1248
Gln Asn Ile Ser Arg Leu Asn Lys Ala Ala Arg Asp Met Gln Thr Ser
                405                 410                 415 atc ttt gtc aaa aat ggt ccg tcc ttt gcg gga tta ggc ttt aga gga        1296
Ile Phe Val Lys Asn Gly Pro Ser Phe Ala Gly Leu Gly Phe Arg Gly
                420                 425                 430 gaa ggt agt act act ttc act att gca acg cct act gga gaa gga aca        1344
Glu Gly Ser Thr Thr Phe Thr Ile Ala Thr Pro Thr Gly Glu Gly Thr
            435                 440                 445 act aca gca cgt cat ttt gct aga cgc cgc cgc tgt gtt tta aca gat        1392
Thr Thr Ala Arg His Phe Ala Arg Arg Arg Arg Cys Val Leu Thr Asp
450                 455                 460 ggt ttt tcg att cgt taa                                                 1410
Gly Phe Ser Ile Arg
465

<210> SEQ ID NO 22
<211> LENGTH: 469
<212> TYPE: PRT
<213> ORGANISM: Listeria innocua

<400> SEQUENCE: 22

Met Glu Ser Leu Glu Leu Glu Gln Leu Val Lys Lys Val Leu Leu Glu
1               5                   10                  15

Lys Leu Ala Glu Gln Lys Glu Val Pro Thr Lys Thr Thr Gln Gly
            20                  25                  30

Ala Lys Ser Gly Val Phe Asp Thr Val Asp Glu Ala Val Gln Ala Ala
        35                  40                  45

Val Ile Ala Gln Asn Cys Tyr Lys Glu Lys Ser Leu Glu Glu Arg Arg
    50                  55                  60

Asn Val Val Lys Ala Ile Arg Glu Ala Leu Tyr Pro Glu Ile Glu Thr
65                  70                  75                  80

Ile Ala Thr Arg Ala Val Ala Glu Thr Gly Met Gly Asn Val Thr Asp
                85                  90                  95

Lys Ile Leu Lys Asn Thr Leu Ala Ile Glu Lys Thr Pro Gly Val Glu
            100                 105                 110

Asp Leu Tyr Thr Glu Val Ala Thr Gly Asp Asn Gly Met Thr Leu Tyr
        115                 120                 125

Glu Leu Ser Pro Tyr Gly Val Ile Gly Ala Val Ala Pro Ser Thr Asn
    130                 135                 140

Pro Thr Glu Thr Leu Ile Cys Asn Ser Ile Gly Met Leu Ala Ala Gly
```

```
                    145                 150                 155                 160
        Asn Ala Val Phe Tyr Ser Pro His Pro Gly Ala Lys Asn Ile Ser Leu
                        165                 170                 175

Trp Leu Ile Glu Lys Leu Asn Thr Ile Val Arg Asp Ser Cys Gly Ile
                        180                 185                 190

Asp Asn Leu Ile Val Thr Val Ala Lys Pro Ser Ile Gln Ala Ala Gln
                        195                 200                 205

Glu Met Met Asn His Pro Lys Val Pro Leu Leu Val Ile Thr Gly Gly
                        210                 215                 220

Pro Gly Val Val Leu Gln Ala Met Gln Ser Gly Lys Lys Val Ile Gly
        225                 230                 235                 240

Ala Gly Ala Gly Asn Pro Pro Ser Ile Val Asp Glu Thr Ala Asn Ile
                        245                 250                 255

Glu Lys Ala Ala Ala Asp Ile Val Asp Gly Ala Ser Phe Asp His Asn
                        260                 265                 270

Ile Leu Cys Ile Ala Glu Lys Ser Val Val Ala Val Asp Ser Ile Ala
                        275                 280                 285

Asp Phe Leu Leu Phe Gln Met Glu Lys Asn Gly Ala Leu His Val Thr
                        290                 295                 300

Asn Pro Ser Asp Ile Gln Lys Leu Glu Lys Val Ala Val Thr Asp Lys
        305                 310                 315                 320

Gly Val Thr Asn Lys Lys Leu Val Gly Lys Ser Ala Thr Glu Ile Leu
                        325                 330                 335

Lys Glu Ala Gly Ile Ala Cys Asp Phe Thr Pro Arg Leu Ile Ile Val
                        340                 345                 350

Glu Thr Glu Lys Ser His Pro Phe Ala Thr Val Glu Leu Leu Met Pro
                        355                 360                 365

Ile Val Pro Val Val Arg Val Pro Asp Phe Asp Glu Ala Leu Glu Val
                        370                 375                 380

Ala Ile Glu Leu Glu Gln Gly Leu His His Thr Ala Thr Met His Ser
        385                 390                 395                 400

Gln Asn Ile Ser Arg Leu Asn Lys Ala Ala Arg Asp Met Gln Thr Ser
                        405                 410                 415

Ile Phe Val Lys Asn Gly Pro Ser Phe Ala Gly Leu Gly Phe Arg Gly
                        420                 425                 430

Glu Gly Ser Thr Thr Phe Thr Ile Ala Thr Pro Thr Gly Glu Gly Thr
                        435                 440                 445

Thr Thr Ala Arg His Phe Ala Arg Arg Arg Cys Val Leu Thr Asp
                        450                 455                 460

Gly Phe Ser Ile Arg
        465

<210> SEQ ID NO 23
<211> LENGTH: 1407
<212> TYPE: DNA
<213> ORGANISM: Artificial
<220> FEATURE:
<223> OTHER INFORMATION: optimised sequence

<400> SEQUENCE: 23
atggaatctt tggaattgga acaattagtc aagaaggttt tgttggaaaa attggctgaa    60
caaaaggaag ttccaaccaa gaccaccacc caaggtgcca agtccggtgt tttcgatacc   120
gtcgatgaag ctgtccaagc tgccgtcatt gctcaaaact gttacaagga aaaatctttg   180
gaagaaagaa gaaacgttgt caaggccatc agagaagctt ataccccaga aatcgaaacc   240
```

-continued

```
attgctacca gagctgttgc tgaaaccggt atgggtaatg tcaccgataa aatcttgaag      300
aacactttag ctatcgaaaa gactccaggt gttgaagact tgtacactga agttgctacc      360
ggtgacaacg gtatgacttt atacgaatta tctccatacg gtgtcatcgg tgctgttgct      420
ccatctacca acccaactga aactttgatc tgtaactcca tcggtatgtt ggctgctggt      480
aacgccgttt tctactctcc tcacccaggt gccaagaaca tctctttatg gttgattgaa      540
aagttgaaca ctatcgtcag agattcttgt ggtattgaca acttgattgt caccgttgcc      600
aagccatcta tccaagctgc tcaagaaatg atgaaccacc caaaggttcc attgttggtc      660
atcactggtg gtccaggtgt tgtcttgcaa gctatgcaat ctggtaagaa ggttatcggt      720
gctggtgctg gtaaccctcc atccatcgtt gacgaaaccg ctaacattga aaaggctgct      780
gctgacattg tcgacggtgc ttcctttgac cataatatct tgtgtatcgc tgaaaagtct      840
gttgttgccg ttgactccat tgctgacttc ttgttgttcc aaatggaaaa gaacggtgct      900
ttgcacgtca ctaacccatc tgatatccaa aaattggaaa aggttgccgt cactgacaag      960
ggtgtcacca acaagaaatt ggttggtaag tctgccactg aaatcttgaa gaagctggt     1020 attgcttgtg atttcacccc aagattgatc attgtcgaaa ctgaaaagtc ccacccattc     1080
gctactgttg aattgttgat gccaattgtt ccagttgtca gagttccaga cttcgatgaa     1140
gctttggaag ttgccattga attggaacaa ggtctacatc acactgctac catgcactct     1200
caaaacatct ccagattgaa caaggctgcc cgtgacatgc aaacctccat ctttgtcaag     1260
aacggtccat ctttcgctgg tttaggtttc agaggtgaag gttccaccac tttcaccatt     1320
gctactccaa ctggtgaagg tactaccact gcccgtcact tcgctagaag aagaagatgt     1380
gtcttgactg atggtttctc cattaga                                          1407
```

<210> SEQ ID NO 24
<211> LENGTH: 1476
<212> TYPE: DNA
<213> ORGANISM: Clostridium kluyveri
<220> FEATURE:
<221> NAME/KEY: CDS
<222> LOCATION: (1)..(1476)

<400> SEQUENCE: 24

```
atg gag ata atg gat aag gac tta cag tca ata cag gaa gta aga act       48
Met Glu Ile Met Asp Lys Asp Leu Gln Ser Ile Gln Glu Val Arg Thr
1               5                  10                  15 ctt ata gca aaa gca aag aaa gct caa gca gaa ttt aaa aat ttt tct       96
Leu Ile Ala Lys Ala Lys Lys Ala Gln Ala Glu Phe Lys Asn Phe Ser
            20                  25                  30 caa gaa gct gta aac aag gta ata gaa aaa ata gct aag gct aca gaa      144
Gln Glu Ala Val Asn Lys Val Ile Glu Lys Ile Ala Lys Ala Thr Glu
        35                  40                  45 gtt gaa gct gta aaa ctt gca aaa ttg gca tat gaa gat aca gga tat      192
Val Glu Ala Val Lys Leu Ala Lys Leu Ala Tyr Glu Asp Thr Gly Tyr
    50                  55                  60 gga aaa tgg gaa gat aaa gta ata aag aat aag ttt tca agt ata gta      240
Gly Lys Trp Glu Asp Lys Val Ile Lys Asn Lys Phe Ser Ser Ile Val
65                  70                  75                  80 gtt tat aac tat att aaa gat ttg aaa acg gtt gga att tta aaa gaa      288
Val Tyr Asn Tyr Ile Lys Asp Leu Lys Thr Val Gly Ile Leu Lys Glu
                85                  90                  95 gac aag gaa aag aaa tta ata gat ata gct gtt cca ctt gga gtt ata      336
Asp Lys Glu Lys Lys Leu Ile Asp Ile Ala Val Pro Leu Gly Val Ile
            100                 105                 110
```

```
gca gga ctt ata cct tca act aac cca act tca aca gca ata ttc aag    384
Ala Gly Leu Ile Pro Ser Thr Asn Pro Thr Ser Thr Ala Ile Phe Lys
        115                 120                 125 gta tta ata gca tta aag gca gga aat gca ata gta ttc tca cca cat    432
Val Leu Ile Ala Leu Lys Ala Gly Asn Ala Ile Val Phe Ser Pro His
    130                 135                 140 cca aca gca gta aga agt att aca gaa act gta aag ata atg cag aaa    480
Pro Thr Ala Val Arg Ser Ile Thr Glu Thr Val Lys Ile Met Gln Lys
145                 150                 155                 160 gct gca gta gaa gca gga gca cca gat gga tta atc caa tgt atg tca    528
Ala Ala Val Glu Ala Gly Ala Pro Asp Gly Leu Ile Gln Cys Met Ser
                165                 170                 175 ata ttg aca gta gaa ggt act gct gaa ttg atg aag aat aag gat aca    576
Ile Leu Thr Val Glu Gly Thr Ala Glu Leu Met Lys Asn Lys Asp Thr
        180                 185                 190 gca ctt atc ctt gca aca ggt gga gaa gga atg gta aga gca gct tac    624
Ala Leu Ile Leu Ala Thr Gly Gly Glu Gly Met Val Arg Ala Ala Tyr
    195                 200                 205 agt tca gga aca cca gct ata gga gtt gga cct gga aac ggc cca tgc    672
Ser Ser Gly Thr Pro Ala Ile Gly Val Gly Pro Gly Asn Gly Pro Cys
210                 215                 220 ttt att gaa aga aca gca gat att cct aca gca gta aga aaa gta ata    720
Phe Ile Glu Arg Thr Ala Asp Ile Pro Thr Ala Val Arg Lys Val Ile
225                 230                 235                 240 ggc agt gat act ttt gat aat gga gta ata tgt gct tca gaa caa tca    768
Gly Ser Asp Thr Phe Asp Asn Gly Val Ile Cys Ala Ser Glu Gln Ser
                245                 250                 255 ata ata gca gag aca gta aag aaa gca gag ata att gaa gaa ttc aag    816
Ile Ile Ala Glu Thr Val Lys Lys Ala Glu Ile Ile Glu Glu Phe Lys
        260                 265                 270 aga caa aaa gga tat ttc tta aat gca gaa gaa tca gaa aaa gta ggc    864
Arg Gln Lys Gly Tyr Phe Leu Asn Ala Glu Glu Ser Glu Lys Val Gly
    275                 280                 285 aag att tta tta aga gct aat gga aca cca aac cca gca ata gta gga    912
Lys Ile Leu Leu Arg Ala Asn Gly Thr Pro Asn Pro Ala Ile Val Gly
290                 295                 300 aaa gat gtt caa gca tta gca aaa tta gca gga ata agc ata cca agc    960
Lys Asp Val Gln Ala Leu Ala Lys Leu Ala Gly Ile Ser Ile Pro Ser
305                 310                 315                 320 gat gcg gta ata tta ctt tca gag cag aca gat gtg agt cca aag aac   1008
Asp Ala Val Ile Leu Leu Ser Glu Gln Thr Asp Val Ser Pro Lys Asn
                325                 330                 335 cct tat gca aag gaa aaa tta gct cca gta ctt gca ttc tat aca gta   1056
Pro Tyr Ala Lys Glu Lys Leu Ala Pro Val Leu Ala Phe Tyr Thr Val
        340                 345                 350 gaa gac tgg cat gaa gca tgt gaa aaa tcc tta gca ctt ctt cat aac   1104
Glu Asp Trp His Glu Ala Cys Glu Lys Ser Leu Ala Leu Leu His Asn
    355                 360                 365 caa gga agt gga cat aca tta ata att cac tca cag aat gaa gaa atc   1152
Gln Gly Ser Gly His Thr Leu Ile Ile His Ser Gln Asn Glu Glu Ile
370                 375                 380 ata aga gaa ttc gca ttg aag aaa cca gta tca aga ata ctt gta aat   1200
Ile Arg Glu Phe Ala Leu Lys Lys Pro Val Ser Arg Ile Leu Val Asn
385                 390                 395                 400 tca cct gga tca ctt gga gga ata ggt gga gct aca aat ctt gta cca   1248
Ser Pro Gly Ser Leu Gly Gly Ile Gly Gly Ala Thr Asn Leu Val Pro
                405                 410                 415 tca ctt aca tta ggc tgt gga gca gta ggt gga agt gca act tca gat   1296
Ser Leu Thr Leu Gly Cys Gly Ala Val Gly Gly Ser Ala Thr Ser Asp
```

```
                     420             425             430
aac gta gga cca gaa aac tta ttc aac ata aga aaa gta gct tat gga    1344
Asn Val Gly Pro Glu Asn Leu Phe Asn Ile Arg Lys Val Ala Tyr Gly
            435                 440                 445 act acg aca gta gaa gaa ata aga gaa gct ttt ggt gta gga gca gct    1392
Thr Thr Thr Val Glu Glu Ile Arg Glu Ala Phe Gly Val Gly Ala Ala
450                 455                 460 tca tca agt gca cca gca gaa cca gaa gat aat gaa gat gta cag gct    1440
Ser Ser Ser Ala Pro Ala Glu Pro Glu Asp Asn Glu Asp Val Gln Ala
465                 470                 475                 480 ata gta aaa gct ata atg gct aaa tta aat ctt taa                    1476
Ile Val Lys Ala Ile Met Ala Lys Leu Asn Leu
                485                 490
```

<210> SEQ ID NO 25
<211> LENGTH: 491
<212> TYPE: PRT
<213> ORGANISM: Clostridium kluyveri

<400> SEQUENCE: 25

```
Met Glu Ile Met Asp Lys Asp Leu Gln Ser Ile Gln Glu Val Arg Thr
1               5                   10                  15

Leu Ile Ala Lys Ala Lys Lys Ala Gln Ala Glu Phe Lys Asn Phe Ser
                20                  25                  30

Gln Glu Ala Val Asn Lys Val Ile Glu Lys Ile Ala Lys Ala Thr Glu
            35                  40                  45

Val Glu Ala Val Lys Leu Ala Lys Leu Ala Tyr Glu Asp Thr Gly Tyr
        50                  55                  60

Gly Lys Trp Glu Asp Lys Val Ile Lys Asn Lys Phe Ser Ser Ile Val
65                  70                  75                  80

Val Tyr Asn Tyr Ile Lys Asp Leu Lys Thr Val Gly Ile Leu Lys Glu
                85                  90                  95

Asp Lys Glu Lys Lys Leu Ile Asp Ile Ala Val Pro Leu Gly Val Ile
            100                 105                 110

Ala Gly Leu Ile Pro Ser Thr Asn Pro Thr Ser Thr Ala Ile Phe Lys
        115                 120                 125

Val Leu Ile Ala Leu Lys Ala Gly Asn Ala Ile Val Phe Ser Pro His
130                 135                 140

Pro Thr Ala Val Arg Ser Ile Thr Glu Thr Val Lys Ile Met Gln Lys
145                 150                 155                 160

Ala Ala Val Glu Ala Gly Ala Pro Asp Gly Leu Ile Gln Cys Met Ser
                165                 170                 175

Ile Leu Thr Val Glu Gly Thr Ala Glu Leu Met Lys Asn Lys Asp Thr
            180                 185                 190

Ala Leu Ile Leu Ala Thr Gly Gly Glu Gly Met Val Arg Ala Ala Tyr
        195                 200                 205

Ser Ser Gly Thr Pro Ala Ile Gly Val Gly Pro Gly Asn Gly Pro Cys
210                 215                 220

Phe Ile Glu Arg Thr Ala Asp Ile Pro Thr Ala Val Arg Lys Val Ile
225                 230                 235                 240

Gly Ser Asp Thr Phe Asp Asn Gly Val Ile Cys Ala Ser Glu Gln Ser
                245                 250                 255

Ile Ile Ala Glu Thr Val Lys Lys Ala Glu Ile Ile Glu Glu Phe Lys
            260                 265                 270

Arg Gln Lys Gly Tyr Phe Leu Asn Ala Glu Glu Ser Glu Lys Val Gly
        275                 280                 285
```

Lys Ile Leu Leu Arg Ala Asn Gly Thr Pro Asn Pro Ala Ile Val Gly
         290                 295                 300

Lys Asp Val Gln Ala Leu Ala Lys Leu Ala Gly Ile Ser Ile Pro Ser
305                 310                 315                 320

Asp Ala Val Ile Leu Leu Ser Glu Gln Thr Asp Val Ser Pro Lys Asn
                325                 330                 335

Pro Tyr Ala Lys Glu Lys Leu Ala Pro Val Leu Ala Phe Tyr Thr Val
            340                 345                 350

Glu Asp Trp His Glu Ala Cys Glu Lys Ser Leu Ala Leu Leu His Asn
        355                 360                 365

Gln Gly Ser Gly His Thr Leu Ile Ile His Ser Gln Asn Glu Glu Ile
370                 375                 380

Ile Arg Glu Phe Ala Leu Lys Lys Pro Val Ser Arg Ile Leu Val Asn
385                 390                 395                 400

Ser Pro Gly Ser Leu Gly Gly Ile Gly Gly Ala Thr Asn Leu Val Pro
                405                 410                 415

Ser Leu Thr Leu Gly Cys Gly Ala Val Gly Gly Ser Ala Thr Ser Asp
            420                 425                 430

Asn Val Gly Pro Glu Asn Leu Phe Asn Ile Arg Lys Val Ala Tyr Gly
        435                 440                 445

Thr Thr Thr Val Glu Glu Ile Arg Glu Ala Phe Gly Val Gly Ala Ala
    450                 455                 460

Ser Ser Ser Ala Pro Ala Glu Pro Glu Asp Asn Glu Asp Val Gln Ala
465                 470                 475                 480

Ile Val Lys Ala Ile Met Ala Lys Leu Asn Leu
                485                 490

<210> SEQ ID NO 26
<211> LENGTH: 1473
<212> TYPE: DNA
<213> ORGANISM: Artificial
<220> FEATURE:
<223> OTHER INFORMATION: optimised sequence

<400> SEQUENCE: 26
atggaaatca tggacaagga tttgcaatcc atccaagaag ttagaacttt gattgccaag      60
gccaagaagg ctcaagctga attcaagaac ttttcccaag aagctgttaa caaggtcatc     120
gaaaagatcg ccaaggctac tgaagttgaa gctgtcaaat tggccaaatt ggcttacgaa     180
gacaccggtt acgtaaatg ggaagacaag gtcatcaaga caaaattctc ctccattgtt     240
gtctacaact acatcaagga tttgaagacc gttggtatct tgaaggaaga caaggaaaag     300
aaattgattg acattgctgt cccattaggt gtcattgctg gtttgattcc atctaccaac     360
ccaacttcca ctgccatttt caaggtcttg attgctttga aggctggtaa cgccattgtc     420
ttctctccac acccaactgc tgtccgttcc atcactgaaa ccgttaagat catgcaaaag     480
gctgctgttg aagctggtgc tccagatggt ttgatccaat gtatgtccat ttgaccgtt      540 gaaggtactg ctgaattgat gaagaacaag gacaccgctt tgatcttggc taccggtggt     600
gaaggtatgg ttagagctgc ttactcctct ggtactccag ccatcggtgt cggtccaggt     660
aacggtccat gtttcatcga agaactgct gacattccaa ctgctgttag aaaggttatc     720
ggttctgaca ctttcgacaa cggtgtcatc tgtgcttctg aacaatccat cattgctgaa     780
accgtcaaga aggctgaaat catcgaagaa ttcaagagac aaaagggtta cttcttgaat     840
gctgaagaat ctgaaaaggt tggtaagatt ctattacgtg ccaacggtac tccaaaccca     900

-continued

```
gccatcgttg gtaaggatgt ccaagctttg gccaaattgg ctggtatttc cattccatct     960
gatgctgtta tcttactatc cgaacaaacc gatgtttctc ctaaaaatcc atacgctaag    1020
gaaaaattgg ctccagtctt ggctttctac accgtcgaag actggcatga agcttgtgaa    1080
aagtctttgg ctttattgca caaccaaggt tctggtcaca ctttgatcat ccactctcaa    1140
aacgaagaaa tcattagaga atttgctttg aagaagcctg tttccagaat tttggttaac    1200
tctccaggtt ctttgggtgg tatcggtggt gctaccaact tagtcccatc tttgacttta    1260
ggttgtggtg ctgttggtgg ttctgccacc tctgacaacg ttggtccaga aaacttgttc    1320
aacatcagaa aggttgctta cggtaccacc accgtcgaag aaatcagaga agctttcggt    1380
gtcggtgctg cttcttcttc tgctccagct gaaccagaag acaacgaaga tgttcaagcc    1440
attgttaagg ccatcatggc caaattgaac ttg                                 1473
```

<210> SEQ ID NO 27
<211> LENGTH: 2610
<212> TYPE: DNA
<213> ORGANISM: Staphylococcus aureus
<220> FEATURE:
<221> NAME/KEY: CDS
<222> LOCATION: (1)..(2610)

<400> SEQUENCE: 27

```
atg tta act ata cct gaa aaa gaa aat cgt gga tcg aaa gaa caa gaa      48
Met Leu Thr Ile Pro Glu Lys Glu Asn Arg Gly Ser Lys Glu Gln Glu
1               5                   10                  15 gtg gca att atg att gat gct cta gct gac aaa ggg aaa aaa gca tta      96
Val Ala Ile Met Ile Asp Ala Leu Ala Asp Lys Gly Lys Lys Ala Leu
            20                  25                  30 gaa gca tta tct aaa aag tca caa gaa gaa att gat cat att gtt cat     144
Glu Ala Leu Ser Lys Lys Ser Gln Glu Glu Ile Asp His Ile Val His
        35                  40                  45 caa atg agc tta gca gct gtt gat caa cat atg gtg cta gca aaa tta     192
Gln Met Ser Leu Ala Ala Val Asp Gln His Met Val Leu Ala Lys Leu
    50                  55                  60 gca cat gaa gaa act gga aga ggt ata tac gaa gat aaa gcg att aaa     240
Ala His Glu Glu Thr Gly Arg Gly Ile Tyr Glu Asp Lys Ala Ile Lys
65                  70                  75                  80 aat tta tac gct tct gaa tat ata tgg aat tca ata aaa gac aat aag     288
Asn Leu Tyr Ala Ser Glu Tyr Ile Trp Asn Ser Ile Lys Asp Asn Lys
                85                  90                  95 aca gta ggg att att ggt gaa gat aaa gaa aaa gga tta acg tat gta     336
Thr Val Gly Ile Ile Gly Glu Asp Lys Glu Lys Gly Leu Thr Tyr Val
            100                 105                 110 gcg gaa cca att ggt gtt att tgt ggt gtt acg cca aca aca aat cct     384
Ala Glu Pro Ile Gly Val Ile Cys Gly Val Thr Pro Thr Thr Asn Pro
        115                 120                 125 acg tcg aca act att ttt aaa gcg atg att gca att aag aca gga aat     432
Thr Ser Thr Thr Ile Phe Lys Ala Met Ile Ala Ile Lys Thr Gly Asn
    130                 135                 140 cca atc att ttt gca ttc cat cca agt gca caa gaa tcg tcg aag cgt     480
Pro Ile Ile Phe Ala Phe His Pro Ser Ala Gln Glu Ser Ser Lys Arg
145                 150                 155                 160 gca gca gaa gtt gta tta gaa gcg gca atg aag gca ggt gca cct aaa     528
Ala Ala Glu Val Val Leu Glu Ala Ala Met Lys Ala Gly Ala Pro Lys
                165                 170                 175 gat att att cag tgg att gaa gtg cct tct atc gaa gca aca aaa caa     576
Asp Ile Ile Gln Trp Ile Glu Val Pro Ser Ile Glu Ala Thr Lys Gln
            180                 185                 190
```

| | | | | | | | | | | | | | | | | |
|---|---|---|---|---|---|---|---|---|---|---|---|---|---|---|---|---|
| tta | atg | aat | cac | aaa | ggt | att | gca | tta | gtt | cta | gca | aca | ggt | ggt | tcg | 624 |
| Leu | Met | Asn | His | Lys | Gly | Ile | Ala | Leu | Val | Leu | Ala | Thr | Gly | Gly | Ser | |
| | | | 195 | | | | 200 | | | | 205 | | | | | |
| ggc | atg | gtt | aag | tct | gca | tat | tca | act | ggc | aaa | ccg | gca | tta | ggt | gtg | 672 |
| Gly | Met | Val | Lys | Ser | Ala | Tyr | Ser | Thr | Gly | Lys | Pro | Ala | Leu | Gly | Val | |
| | 210 | | | | | 215 | | | | | 220 | | | | | |
| gga | cca | ggt | aac | gtg | ccg | tct | tac | att | gaa | aaa | aca | gca | cac | att | aaa | 720 |
| Gly | Pro | Gly | Asn | Val | Pro | Ser | Tyr | Ile | Glu | Lys | Thr | Ala | His | Ile | Lys | |
| 225 | | | | | 230 | | | | | 235 | | | | | 240 | |
| cgt | gca | gta | aat | gat | atc | att | ggt | tca | aaa | aca | ttt | gat | aat | ggt | atg | 768 |
| Arg | Ala | Val | Asn | Asp | Ile | Ile | Gly | Ser | Lys | Thr | Phe | Asp | Asn | Gly | Met | |
| | | | | 245 | | | | | 250 | | | | | 255 | | |
| att | tgt | gct | tct | gaa | caa | gtt | gta | gtc | att | gat | aaa | gaa | att | tat | aaa | 816 |
| Ile | Cys | Ala | Ser | Glu | Gln | Val | Val | Val | Ile | Asp | Lys | Glu | Ile | Tyr | Lys | |
| | | | | 260 | | | | | 265 | | | | | 270 | | |
| gat | gtt | act | aat | gaa | ttt | aaa | gca | cat | caa | gca | tac | ttt | gtt | aaa | aaa | 864 |
| Asp | Val | Thr | Asn | Glu | Phe | Lys | Ala | His | Gln | Ala | Tyr | Phe | Val | Lys | Lys | |
| | | 275 | | | | | 280 | | | | | 285 | | | | |
| gat | gaa | tta | caa | cgc | tta | gaa | aat | gca | att | atg | aat | gaa | caa | aaa | aca | 912 |
| Asp | Glu | Leu | Gln | Arg | Leu | Glu | Asn | Ala | Ile | Met | Asn | Glu | Gln | Lys | Thr | |
| | 290 | | | | | 295 | | | | | 300 | | | | | |
| ggt | att | aag | cct | gat | att | gtc | ggt | aaa | tct | gca | gtt | gaa | ata | gct | gaa | 960 |
| Gly | Ile | Lys | Pro | Asp | Ile | Val | Gly | Lys | Ser | Ala | Val | Glu | Ile | Ala | Glu | |
| 305 | | | | | 310 | | | | | 315 | | | | | 320 | |
| tta | gca | ggt | ata | cct | gtc | ccc | gaa | aat | aca | aaa | ctt | atc | ata | gcc | gaa | 1008 |
| Leu | Ala | Gly | Ile | Pro | Val | Pro | Glu | Asn | Thr | Lys | Leu | Ile | Ile | Ala | Glu | |
| | | | | 325 | | | | | 330 | | | | | 335 | | |
| att | agc | ggt | gta | ggt | tca | gac | tat | ccg | tta | tct | cgt | gaa | aaa | tta | tct | 1056 |
| Ile | Ser | Gly | Val | Gly | Ser | Asp | Tyr | Pro | Leu | Ser | Arg | Glu | Lys | Leu | Ser | |
| | | | | 340 | | | | | 345 | | | | | 350 | | |
| cca | gta | tta | gcc | tta | gta | aaa | gcc | caa | tct | aca | aaa | caa | gca | ttt | caa | 1104 |
| Pro | Val | Leu | Ala | Leu | Val | Lys | Ala | Gln | Ser | Thr | Lys | Gln | Ala | Phe | Gln | |
| | | 355 | | | | | 360 | | | | | 365 | | | | |
| att | tgt | gaa | gac | aca | cta | cat | ttt | ggt | gga | tta | gga | cac | aca | gcc | gtt | 1152 |
| Ile | Cys | Glu | Asp | Thr | Leu | His | Phe | Gly | Gly | Leu | Gly | His | Thr | Ala | Val | |
| | 370 | | | | | 375 | | | | | 380 | | | | | |
| atc | cat | aca | gaa | gat | gaa | aca | tta | caa | aaa | gat | ttt | gga | cta | aga | atg | 1200 |
| Ile | His | Thr | Glu | Asp | Glu | Thr | Leu | Gln | Lys | Asp | Phe | Gly | Leu | Arg | Met | |
| 385 | | | | | 390 | | | | | 395 | | | | | 400 | |
| aaa | gct | tgt | cgt | gta | ctt | gta | aat | aca | cca | tca | gcg | gtt | gga | ggt | att | 1248 |
| Lys | Ala | Cys | Arg | Val | Leu | Val | Asn | Thr | Pro | Ser | Ala | Val | Gly | Gly | Ile | |
| | | | 405 | | | | | 410 | | | | | 415 | | | |
| ggt | gat | atg | tat | aac | gaa | ttg | att | ccg | tct | tta | aca | tta | ggt | tgt | ggt | 1296 |
| Gly | Asp | Met | Tyr | Asn | Glu | Leu | Ile | Pro | Ser | Leu | Thr | Leu | Gly | Cys | Gly | |
| | | | | 420 | | | | | 425 | | | | | 430 | | |
| tcg | tac | ggt | aga | aac | tca | att | tca | cat | aat | gtt | agt | gcg | aca | gat | tta | 1344 |
| Ser | Tyr | Gly | Arg | Asn | Ser | Ile | Ser | His | Asn | Val | Ser | Ala | Thr | Asp | Leu | |
| | | | 435 | | | | | 440 | | | | | 445 | | | |
| tta | aac | att | aaa | acg | att | gct | aaa | cga | cgt | aat | aat | act | caa | att | ttc | 1392 |
| Leu | Asn | Ile | Lys | Thr | Ile | Ala | Lys | Arg | Arg | Asn | Asn | Thr | Gln | Ile | Phe | |
| | 450 | | | | | 455 | | | | | 460 | | | | | |
| aag | gtg | cct | gct | caa | att | tat | ttt | gaa | gaa | aat | gca | atc | atg | agt | cta | 1440 |
| Lys | Val | Pro | Ala | Gln | Ile | Tyr | Phe | Glu | Glu | Asn | Ala | Ile | Met | Ser | Leu | |
| 465 | | | | | 470 | | | | | 475 | | | | | 480 | |
| aca | aca | atg | gac | aag | att | gaa | aaa | gtg | atg | att | gtc | tgt | gac | cct | ggt | 1488 |
| Thr | Thr | Met | Asp | Lys | Ile | Glu | Lys | Val | Met | Ile | Val | Cys | Asp | Pro | Gly | |
| | | | | 485 | | | | | 490 | | | | | 495 | | |
| atg | gta | gaa | ttc | ggt | tat | aca | aaa | aca | gtt | gag | aat | gta | tta | aga | caa | 1536 |
| Met | Val | Glu | Phe | Gly | Tyr | Thr | Lys | Thr | Val | Glu | Asn | Val | Leu | Arg | Gln | |

|  |  |
|---|---|
| aga acg gaa cag cct caa att aaa ata ttt agc gaa gtc gaa ccg aac<br>Arg Thr Glu Gln Pro Gln Ile Lys Ile Phe Ser Glu Val Glu Pro Asn<br>    515                      520                          525 | 1584 |
| cca tca act aat aca gta tat aaa ggt ctg gaa atg atg gtt gat ttc<br>Pro Ser Thr Asn Thr Val Tyr Lys Gly Leu Glu Met Met Val Asp Phe<br>530                      535                      540 | 1632 |
| caa cca gat aca atc att gca ctt ggt ggt ggt tca gcg atg gat gct<br>Gln Pro Asp Thr Ile Ile Ala Leu Gly Gly Gly Ser Ala Met Asp Ala<br>545                      550                      555                      560 | 1680 |
| gca aaa gca atg tgg atg ttc ttt gaa cac cct gag aca tca ttc ttc<br>Ala Lys Ala Met Trp Met Phe Phe Glu His Pro Glu Thr Ser Phe Phe<br>                      565                      570                      575 | 1728 |
| ggt gct aaa caa aag ttc cta gac atc ggt aaa cgt act tat aaa ata<br>Gly Ala Lys Gln Lys Phe Leu Asp Ile Gly Lys Arg Thr Tyr Lys Ile<br>        580                      585                          590 | 1776 |
| ggc atg cct gaa aat gcg acg ttc att tgt atc cct acg aca tca ggt<br>Gly Met Pro Glu Asn Ala Thr Phe Ile Cys Ile Pro Thr Thr Ser Gly<br>              595                      600                      605 | 1824 |
| aca ggt tca gaa gta aca cca ttt gca gtt atc aca gat agt gaa aca<br>Thr Gly Ser Glu Val Thr Pro Phe Ala Val Ile Thr Asp Ser Glu Thr<br>610                      615                      620 | 1872 |
| aat gta aaa tat ccg ttg gct gat ttt gct tta aca cct gac gtt gca<br>Asn Val Lys Tyr Pro Leu Ala Asp Phe Ala Leu Thr Pro Asp Val Ala<br>625                      630                      635                      640 | 1920 |
| att att gac cct caa ttt gtg atg agt gtg cca aaa agc gtt aca gca<br>Ile Ile Asp Pro Gln Phe Val Met Ser Val Pro Lys Ser Val Thr Ala<br>                      645                      650                      655 | 1968 |
| gat aca gga atg gat gta cta acg cat gca atg gaa tca tat gta tct<br>Asp Thr Gly Met Asp Val Leu Thr His Ala Met Glu Ser Tyr Val Ser<br>                      660                      665                      670 | 2016 |
| gta atg gct tca gac tat aca aga ggt ttg agt cta caa gcg att aaa<br>Val Met Ala Ser Asp Tyr Thr Arg Gly Leu Ser Leu Gln Ala Ile Lys<br>        675                      680                          685 | 2064 |
| ttg acg ttc gaa tat tta aaa tca tct gtt gaa aag ggt gat aaa gtt<br>Leu Thr Phe Glu Tyr Leu Lys Ser Ser Val Glu Lys Gly Asp Lys Val<br>690                      695                      700 | 2112 |
| tca aga gag aaa atg cat aac gca tca act ttg gct ggt atg gca ttt<br>Ser Arg Glu Lys Met His Asn Ala Ser Thr Leu Ala Gly Met Ala Phe<br>705                      710                      715                      720 | 2160 |
| gca aat gca ttc tta ggc att gca cac tca att gca cat aaa att ggt<br>Ala Asn Ala Phe Leu Gly Ile Ala His Ser Ile Ala His Lys Ile Gly<br>                      725                      730                      735 | 2208 |
| ggc gaa tat ggt att ccg cat ggt aga gcg aat gcg ata tta cta ccg<br>Gly Glu Tyr Gly Ile Pro His Gly Arg Ala Asn Ala Ile Leu Leu Pro<br>        740                      745                          750 | 2256 |
| cat att atc cgt tat aat gcc aaa gac ccg caa aaa cat gca tta ttc<br>His Ile Ile Arg Tyr Asn Ala Lys Asp Pro Gln Lys His Ala Leu Phe<br>              755                      760                      765 | 2304 |
| cct aaa tat gag ttc ttc aga gca gat aca gat tat gca gat att gcc<br>Pro Lys Tyr Glu Phe Phe Arg Ala Asp Thr Asp Tyr Ala Asp Ile Ala<br>770                      775                      780 | 2352 |
| aaa ttc tta gga tta aaa ggg aat acg aca gaa gca ctc gta gaa tca<br>Lys Phe Leu Gly Leu Lys Gly Asn Thr Thr Glu Ala Leu Val Glu Ser<br>785                      790                      795                      800 | 2400 |
| tta gct aaa gct gtc tac gaa tta ggt caa tca gtc gga att gaa atg<br>Leu Ala Lys Ala Val Tyr Glu Leu Gly Gln Ser Val Gly Ile Glu Met<br>                      805                      810                      815 | 2448 |
| aat ttg aaa tca caa ggt gtg tct gaa gaa gaa tta aat gaa tca att | 2496 |

```
Asn Leu Lys Ser Gln Gly Val Ser Glu Glu Leu Asn Glu Ser Ile
            820                 825                 830 gat aga atg gca gag ctc gca ttt gaa gat caa tgt aca act gct aat    2544
Asp Arg Met Ala Glu Leu Ala Phe Glu Asp Gln Cys Thr Thr Ala Asn
        835                 840                 845 cct aaa gaa gca cta atc agt gaa atc aaa gat atc att caa aca tca    2592
Pro Lys Glu Ala Leu Ile Ser Glu Ile Lys Asp Ile Ile Gln Thr Ser
850                 855                 860 tat gat tat aag caa taa                                            2610
Tyr Asp Tyr Lys Gln
865

<210> SEQ ID NO 28
<211> LENGTH: 869
<212> TYPE: PRT
<213> ORGANISM: Staphylococcus aureus

<400> SEQUENCE: 28

Met Leu Thr Ile Pro Glu Lys Glu Asn Arg Gly Ser Lys Gln Glu
1               5                   10                  15

Val Ala Ile Met Ile Asp Ala Leu Ala Asp Lys Gly Lys Lys Ala Leu
            20                  25                  30

Glu Ala Leu Ser Lys Lys Ser Gln Glu Ile Asp His Ile Val His
        35                  40                  45

Gln Met Ser Leu Ala Ala Val Asp Gln His Met Val Leu Ala Lys Leu
    50                  55                  60

Ala His Glu Glu Thr Gly Arg Gly Ile Tyr Glu Asp Lys Ala Ile Lys
65                  70                  75                  80

Asn Leu Tyr Ala Ser Glu Tyr Ile Trp Asn Ser Ile Lys Asp Asn Lys
                85                  90                  95

Thr Val Gly Ile Ile Gly Glu Asp Lys Glu Lys Gly Leu Thr Tyr Val
            100                 105                 110

Ala Glu Pro Ile Gly Val Ile Cys Gly Val Thr Pro Thr Thr Asn Pro
        115                 120                 125

Thr Ser Thr Thr Ile Phe Lys Ala Met Ile Ala Ile Lys Thr Gly Asn
    130                 135                 140

Pro Ile Ile Phe Ala Phe His Pro Ser Ala Gln Glu Ser Ser Lys Arg
145                 150                 155                 160

Ala Ala Glu Val Val Leu Glu Ala Ala Met Lys Ala Gly Ala Pro Lys
                165                 170                 175

Asp Ile Ile Gln Trp Ile Glu Val Pro Ser Ile Glu Ala Thr Lys Gln
            180                 185                 190

Leu Met Asn His Lys Gly Ile Ala Leu Val Leu Ala Thr Gly Gly Ser
        195                 200                 205

Gly Met Val Lys Ser Ala Tyr Ser Thr Gly Lys Pro Ala Leu Gly Val
    210                 215                 220

Gly Pro Gly Asn Val Pro Ser Tyr Ile Glu Lys Thr Ala His Ile Lys
225                 230                 235                 240

Arg Ala Val Asn Asp Ile Ile Gly Ser Lys Thr Phe Asp Asn Gly Met
                245                 250                 255

Ile Cys Ala Ser Glu Gln Val Val Ile Asp Lys Glu Ile Tyr Lys
            260                 265                 270

Asp Val Thr Asn Glu Phe Lys Ala His Gln Ala Tyr Phe Val Lys Lys
        275                 280                 285

Asp Glu Leu Gln Arg Leu Glu Asn Ala Ile Met Asn Glu Gln Lys Thr
    290                 295                 300
```

```
Gly Ile Lys Pro Asp Ile Val Gly Lys Ser Ala Val Glu Ile Ala Glu
305                 310                 315                 320

Leu Ala Gly Ile Pro Val Pro Glu Asn Thr Lys Leu Ile Ile Ala Glu
            325                 330                 335

Ile Ser Gly Val Gly Ser Asp Tyr Pro Leu Ser Arg Glu Lys Leu Ser
                340                 345                 350

Pro Val Leu Ala Leu Val Lys Ala Gln Ser Thr Lys Gln Ala Phe Gln
                355                 360                 365

Ile Cys Glu Asp Thr Leu His Phe Gly Gly Leu Gly His Thr Ala Val
370                 375                 380

Ile His Thr Glu Asp Glu Thr Leu Gln Lys Asp Phe Gly Leu Arg Met
385                 390                 395                 400

Lys Ala Cys Arg Val Leu Val Asn Thr Pro Ser Ala Val Gly Gly Ile
                405                 410                 415

Gly Asp Met Tyr Asn Glu Leu Ile Pro Ser Leu Thr Leu Gly Cys Gly
                420                 425                 430

Ser Tyr Gly Arg Asn Ser Ile Ser His Asn Val Ser Ala Thr Asp Leu
                435                 440                 445

Leu Asn Ile Lys Thr Ile Ala Lys Arg Asn Asn Thr Gln Ile Phe
450                 455                 460

Lys Val Pro Ala Gln Ile Tyr Phe Glu Glu Asn Ala Ile Met Ser Leu
465                 470                 475                 480

Thr Thr Met Asp Lys Ile Glu Lys Val Met Ile Val Cys Asp Pro Gly
                485                 490                 495

Met Val Glu Phe Gly Tyr Thr Lys Thr Val Glu Asn Val Leu Arg Gln
                500                 505                 510

Arg Thr Glu Gln Pro Gln Ile Lys Ile Phe Ser Glu Val Glu Pro Asn
                515                 520                 525

Pro Ser Thr Asn Thr Val Tyr Lys Gly Leu Glu Met Met Val Asp Phe
530                 535                 540

Gln Pro Asp Thr Ile Ile Ala Leu Gly Gly Gly Ser Ala Met Asp Ala
545                 550                 555                 560

Ala Lys Ala Met Trp Met Phe Phe Glu His Pro Glu Thr Ser Phe Phe
                565                 570                 575

Gly Ala Lys Gln Lys Phe Leu Asp Ile Gly Lys Arg Thr Tyr Lys Ile
                580                 585                 590

Gly Met Pro Glu Asn Ala Thr Phe Ile Cys Ile Pro Thr Thr Ser Gly
                595                 600                 605

Thr Gly Ser Glu Val Thr Pro Phe Ala Val Ile Thr Asp Ser Glu Thr
                610                 615                 620

Asn Val Lys Tyr Pro Leu Ala Asp Phe Ala Leu Thr Pro Asp Val Ala
625                 630                 635                 640

Ile Ile Asp Pro Gln Phe Val Met Ser Val Pro Lys Ser Val Thr Ala
                645                 650                 655

Asp Thr Gly Met Asp Val Leu Thr His Ala Met Glu Ser Tyr Val Ser
                660                 665                 670

Val Met Ala Ser Asp Tyr Thr Arg Gly Leu Ser Leu Gln Ala Ile Lys
                675                 680                 685

Leu Thr Phe Glu Tyr Leu Lys Ser Ser Val Glu Lys Gly Asp Lys Val
                690                 695                 700

Ser Arg Glu Lys Met His Asn Ala Ser Thr Leu Ala Gly Met Ala Phe
705                 710                 715                 720
```

```
Ala Asn Ala Phe Leu Gly Ile Ala His Ser Ile Ala His Lys Ile Gly
                725                 730                 735

Gly Glu Tyr Gly Ile Pro His Gly Arg Ala Asn Ala Ile Leu Leu Pro
            740                 745                 750

His Ile Ile Arg Tyr Asn Ala Lys Asp Pro Gln Lys His Ala Leu Phe
        755                 760                 765

Pro Lys Tyr Glu Phe Phe Arg Ala Asp Thr Asp Tyr Ala Asp Ile Ala
    770                 775                 780

Lys Phe Leu Gly Leu Lys Gly Asn Thr Thr Glu Ala Leu Val Glu Ser
785                 790                 795                 800

Leu Ala Lys Ala Val Tyr Glu Leu Gly Gln Ser Val Gly Ile Glu Met
                805                 810                 815

Asn Leu Lys Ser Gln Gly Val Ser Glu Glu Leu Asn Glu Ser Ile
            820                 825                 830

Asp Arg Met Ala Glu Leu Ala Phe Glu Asp Gln Cys Thr Thr Ala Asn
        835                 840                 845

Pro Lys Glu Ala Leu Ile Ser Glu Ile Lys Asp Ile Ile Gln Thr Ser
    850                 855                 860

Tyr Asp Tyr Lys Gln
865

<210> SEQ ID NO 29
<211> LENGTH: 2607
<212> TYPE: DNA
<213> ORGANISM: Artificial
<220> FEATURE:
<223> OTHER INFORMATION: optimised sequence

<400> SEQUENCE: 29
atgttgacca ttccagaaaa ggaaaacaga ggttccaagg aacaagaagt tgccatcatg      60
attgatgctt tagctgacaa aggtaagaag gctttggaag ctttgtccaa gaagtctcaa     120
gaagaaattg accacattgt ccaccaaatg tccttggctg ctgttgacca acacatggtt     180
ttggccaagt tggctcatga agaaaccggt agaggtatct acgaagacaa ggctatcaag     240
aacttatacg cctctgaata catctggaac tccatcaagg acaacaagac tgttggtatc     300
attggtgaag acaaagaaaa gggtttgacc tacgttgctg aaccaattgg tgtcatctgt     360
ggtgtcactc caaccaccaa cccaacttct accaccatct tcaaggctat gattgccatc     420
aagactggta acccaattat tttcgctttc cacccatctg ctcaagaatc ttccaagaga     480
gctgctgaag ttgttttgga agctgccatg aaggctggtg ctccaaagga tatcatccaa     540
tggattgaag ttccatccat gaagctacc aagcaattga tgaaccacaa gggtattgct     600
ttagtcttgg ctaccggtgg ttctggtatg gttaagtctg cttactccac tggtaaacca     660
gctttgggtg ttggtccagg taacgttcca tcttacatcg aaaagactgc tcatatcaag     720
cgtgctgtca cgatatcat cggttccaag actttcgata tggtatgat ctgtgcttct     780 gaacaagttg ttgtcattga caggaaatc tacaaggatc accaatga attcaaggct     840 caccaagctt acttcgtcaa gaaggacgaa ttacaaagat agaaaacgc catcatgaac     900 gaacaaaaga ctggtatcaa gccagatatc gttggtaagt ctgctgttga aattgctgaa     960
ttggccggta tcccagttcc agaaaacacc aaattgatca ttgctgaaat ctccggtgtc    1020
ggttctgact acccattgtc cagagaaaag ttgtctccag ttttggcttt agtcaaggct    1080
caatctacca gcaagctttt ccaaatctgt gaagacactt tgcacttcgg tggtttaggt    1140
cacactgctg ttatccacac tgaagacgaa actttgcaaa aggatttcgg tctaagaatg    1200
```

```
aaggcttgtc gtgttttggt caacactcca tctgctgttg gtggtatcgg tgacatgtac   1260
aacgaattga ttccatcctt gactttgggt tgtggttctt acggtagaaa ctccatctcc   1320
cacaacgtct ctgctaccga tttgttgaac atcaagacca ttgccaagag aagaaacaac   1380
actcaaatct tcaaggttcc agctcaaatc tatttcgaag aaaacgctat catgtccttg   1440
accaccatgg acaagattga aaaggtcatg atcgtttgtg acccaggtat ggttgaattt   1500
ggttacacca aaaccgtcga aaacgtctta cgtcaaagaa ctgaacaacc tcaaatcaag   1560
atcttctctg aagttgaacc aaatccatcc accaacactg tctacaaggg tttggaaatg   1620
atggtcgatt ccaaccaga caccatcatt gctttgggtg gtggttctgc catggatgct   1680
gccaaggcta tgtggatgtt cttcgaacat ccagaaactt ctttcttcgg tgccaagcaa   1740
aaattcttgg acattggtaa agaacctac aagattggta tgccagaaaa cgccactttc   1800
atctgtattc caaccacttc tggtactggt tctgaagtca ctccatttgc tgttatcact   1860
gactctgaaa ccaacgtcaa atacccattg gctgatttcg ctttgactcc agatgtcgcc   1920
atcattgacc ctcaatttgt catgtccgtc ccaaaatctg tcactgctga taccggtatg   1980
gacgttttga ctcacgctat ggaatcttac gtttctgtca tggcctccga ttacaccaga   2040
ggtttgtccc tacaagctat caaattgacc tttgaatact gaaatcttc cgttgaaaaa   2100 ggtgacaagg tttccagaga aaagatgcac aacgcttcta ctttggccgg tatggccttt   2160
gctaacgctt tcttgggtat tgctcactcc attgctcaca aaattggtgg tgaatacggt   2220
attccacatg gtagagctaa cgccatcttg ttgcctcaca tcatcagata caacgccaag   2280
gaccctcaaa agcacgcttt gttcccaaag tacgaattct tcagagctga caccgattac   2340
gctgatatcg ccaagttctt aggttttgaaa ggtaacacca ctgaagcttt ggttgaatct   2400
ttggccaagg ctgtctacga attaggtcaa tctgttggta ttgaaatgaa cttgaaatct   2460
caaggtgtct ctgaagaaga attgaacgaa tccattgaca gaatggctga attggctttc   2520
gaagaccaat gtaccactgc caacccaaag gaagctttga tttctgaaat caaggatatc   2580
atccaaactt cttacgacta caagcag                                      2607
```

<210> SEQ ID NO 30
<211> LENGTH: 392
<212> TYPE: PRT
<213> ORGANISM: Clostridium acetobutylicum

<400> SEQUENCE: 30

```
Met Lys Glu Val Val Ile Ala Ser Ala Val Arg Thr Ala Ile Gly Ser
1               5                   10                  15

Tyr Gly Lys Ser Leu Lys Asp Val Pro Ala Val Asp Leu Gly Ala Thr
            20                  25                  30

Ala Ile Lys Glu Ala Val Lys Lys Ala Gly Ile Lys Pro Glu Asp Val
        35                  40                  45

Asn Glu Val Ile Leu Gly Asn Val Leu Gln Ala Gly Leu Gly Gln Asn
    50                  55                  60

Pro Ala Arg Gln Ala Ser Phe Lys Ala Gly Leu Pro Val Glu Ile Pro
65                  70                  75                  80

Ala Met Thr Ile Asn Lys Val Cys Gly Ser Gly Leu Arg Thr Val Ser
            85                  90                  95

Leu Ala Ala Gln Ile Ile Lys Ala Gly Asp Ala Asp Val Ile Ile Ala
        100                 105                 110

Gly Gly Met Glu Asn Met Ser Arg Ala Pro Tyr Leu Ala Asn Asn Ala
```

```
            115                 120                 125
Arg Trp Gly Tyr Arg Met Gly Asn Ala Lys Phe Val Asp Glu Met Ile
        130                 135                 140

Thr Asp Gly Leu Trp Asp Ala Phe Asn Asp Tyr His Met Gly Ile Thr
145                 150                 155                 160

Ala Glu Asn Ile Ala Glu Arg Trp Asn Ile Ser Arg Glu Glu Gln Asp
                165                 170                 175

Glu Phe Ala Leu Ala Ser Gln Lys Lys Ala Glu Ala Ile Lys Ser
            180                 185                 190

Gly Gln Phe Lys Asp Glu Ile Val Pro Val Ile Lys Gly Arg Lys
        195                 200                 205

Gly Glu Thr Val Val Asp Thr Asp Glu His Pro Arg Phe Gly Ser Thr
        210                 215                 220

Ile Glu Gly Leu Ala Lys Leu Lys Pro Ala Phe Lys Lys Asp Gly Thr
225                 230                 235                 240

Val Thr Ala Gly Asn Ala Ser Gly Leu Asn Asp Cys Ala Ala Val Leu
                245                 250                 255

Val Ile Met Ser Ala Glu Lys Ala Lys Glu Leu Gly Val Lys Pro Leu
            260                 265                 270

Ala Lys Ile Val Ser Tyr Gly Ser Ala Gly Val Asp Pro Ala Ile Met
        275                 280                 285

Gly Tyr Gly Pro Phe Tyr Ala Thr Lys Ala Ala Ile Glu Lys Ala Gly
        290                 295                 300

Trp Thr Val Asp Glu Leu Asp Leu Ile Glu Ser Asn Glu Ala Phe Ala
305                 310                 315                 320

Ala Gln Ser Leu Ala Val Ala Lys Asp Leu Lys Phe Asp Met Asn Lys
                325                 330                 335

Val Asn Val Asn Gly Gly Ala Ile Ala Leu Gly His Pro Ile Gly Ala
            340                 345                 350

Ser Gly Ala Arg Ile Leu Val Thr Leu Val His Ala Met Gln Lys Arg
        355                 360                 365

Asp Ala Lys Lys Gly Leu Ala Thr Leu Cys Ile Gly Gly Gly Gln Gly
        370                 375                 380

Thr Ala Ile Leu Leu Glu Lys Cys
385                 390

<210> SEQ ID NO 31
<211> LENGTH: 282
<212> TYPE: PRT
<213> ORGANISM: Clostridium acetobutylicum

<400> SEQUENCE: 31

Met Lys Lys Val Cys Val Ile Gly Ala Gly Thr Met Gly Ser Gly Ile
1               5                   10                  15

Ala Gln Ala Phe Ala Ala Lys Gly Phe Glu Val Val Leu Arg Asp Ile
            20                  25                  30

Lys Asp Glu Phe Val Asp Arg Gly Leu Asp Phe Ile Asn Lys Asn Leu
        35                  40                  45

Ser Lys Leu Val Lys Lys Gly Lys Ile Glu Glu Ala Thr Lys Val Glu
    50                  55                  60

Ile Leu Thr Arg Ile Ser Gly Thr Val Asp Leu Asn Met Ala Ala Asp
65                  70                  75                  80

Cys Asp Leu Val Ile Glu Ala Ala Val Glu Arg Met Asp Ile Lys Lys
                85                  90                  95
```

```
Gln Ile Phe Ala Asp Leu Asp Asn Ile Cys Lys Pro Glu Thr Ile Leu
                100                 105                 110
Ala Ser Asn Thr Ser Ser Leu Ser Ile Thr Glu Val Ala Ser Ala Thr
            115                 120                 125
Lys Arg Pro Asp Lys Val Ile Gly Met His Phe Phe Asn Pro Ala Pro
130                 135                 140
Val Met Lys Leu Val Glu Val Ile Arg Gly Ile Ala Thr Ser Gln Glu
145                 150                 155                 160
Thr Phe Asp Ala Val Lys Glu Thr Ser Ile Ala Ile Gly Lys Asp Pro
                165                 170                 175
Val Glu Val Ala Glu Ala Pro Gly Phe Val Val Asn Arg Ile Leu Ile
            180                 185                 190
Pro Met Ile Asn Glu Ala Val Gly Ile Leu Ala Glu Gly Ile Ala Ser
        195                 200                 205
Val Glu Asp Ile Asp Lys Ala Met Lys Leu Gly Ala Asn His Pro Met
    210                 215                 220
Gly Pro Leu Glu Leu Gly Asp Phe Ile Gly Leu Asp Ile Cys Leu Ala
225                 230                 235                 240
Ile Met Asp Val Leu Tyr Ser Glu Thr Gly Asp Ser Lys Tyr Arg Pro
                245                 250                 255
His Thr Leu Leu Lys Lys Tyr Val Arg Ala Gly Trp Leu Gly Arg Lys
            260                 265                 270
Ser Gly Lys Gly Phe Tyr Asp Tyr Ser Lys
        275                 280

<210> SEQ ID NO 32
<211> LENGTH: 261
<212> TYPE: PRT
<213> ORGANISM: Clostridium acetobutylicum

<400> SEQUENCE: 32

Met Glu Leu Asn Asn Val Ile Leu Glu Lys Glu Gly Lys Val Ala Val
1               5                   10                  15
Val Thr Ile Asn Arg Pro Lys Ala Leu Asn Ala Leu Asn Ser Asp Thr
            20                  25                  30
Leu Lys Glu Met Asp Tyr Val Ile Gly Glu Ile Glu Asn Asp Ser Glu
        35                  40                  45
Val Leu Ala Val Ile Leu Thr Gly Ala Gly Glu Lys Ser Phe Val Ala
    50                  55                  60
Gly Ala Asp Ile Ser Glu Met Lys Glu Met Asn Thr Ile Glu Gly Arg
65                  70                  75                  80
Lys Phe Gly Ile Leu Gly Asn Lys Val Phe Arg Arg Leu Glu Leu Leu
                85                  90                  95
Glu Lys Pro Val Ile Ala Ala Val Asn Gly Phe Ala Leu Gly Gly Gly
            100                 105                 110
Cys Glu Ile Ala Met Ser Cys Asp Ile Arg Ile Ala Ser Ser Asn Ala
        115                 120                 125
Arg Phe Gly Gln Pro Glu Val Gly Leu Gly Ile Thr Pro Gly Phe Gly
    130                 135                 140
Gly Thr Gln Arg Leu Ser Arg Leu Val Gly Met Gly Met Ala Lys Gln
145                 150                 155                 160
Leu Ile Phe Thr Ala Gln Asn Ile Lys Ala Asp Glu Ala Leu Arg Ile
                165                 170                 175
Gly Leu Val Asn Lys Val Val Glu Pro Ser Glu Leu Met Asn Thr Ala
            180                 185                 190
```

Lys Glu Ile Ala Asn Lys Ile Val Ser Asn Ala Pro Val Ala Val Lys
            195                 200                 205

Leu Ser Lys Gln Ala Ile Asn Arg Gly Met Gln Cys Asp Ile Asp Thr
        210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260

<210> SEQ ID NO 33
<211> LENGTH: 379
<212> TYPE: PRT
<213> ORGANISM: Clostridium acetobutylicum

<400> SEQUENCE: 33

Met Asp Phe Asn Leu Thr Arg Glu Gln Glu Leu Val Arg Gln Met Val
1               5                   10                  15

Arg Glu Phe Ala Glu Asn Glu Val Lys Pro Ile Ala Ala Glu Ile Asp
            20                  25                  30

Glu Thr Glu Arg Phe Pro Met Glu Asn Val Lys Lys Met Gly Gln Tyr
        35                  40                  45

Gly Met Met Gly Ile Pro Phe Ser Lys Glu Tyr Gly Gly Ala Gly Gly
    50                  55                  60

Asp Val Leu Ser Tyr Ile Ile Ala Val Glu Glu Leu Ser Lys Val Cys
65                  70                  75                  80

Gly Thr Thr Gly Val Ile Leu Ser Ala His Thr Ser Leu Cys Ala Ser
                85                  90                  95

Leu Ile Asn Glu His Gly Thr Glu Glu Gln Lys Gln Lys Tyr Leu Val
            100                 105                 110

Pro Leu Ala Lys Gly Glu Lys Ile Gly Ala Tyr Gly Leu Thr Glu Pro
        115                 120                 125

Asn Ala Gly Thr Asp Ser Gly Ala Gln Gln Thr Val Ala Val Leu Glu
    130                 135                 140

Gly Asp His Tyr Val Ile Asn Gly Ser Lys Ile Phe Ile Thr Asn Gly
145                 150                 155                 160

Gly Val Ala Asp Thr Phe Val Ile Phe Ala Met Thr Asp Arg Thr Lys
                165                 170                 175

Gly Thr Lys Gly Ile Ser Ala Phe Ile Ile Glu Lys Gly Phe Lys Gly
            180                 185                 190

Phe Ser Ile Gly Lys Val Glu Gln Lys Leu Gly Ile Arg Ala Ser Ser
        195                 200                 205

Thr Thr Glu Leu Val Phe Glu Asp Met Ile Val Pro Val Glu Asn Met
    210                 215                 220

Ile Gly Lys Glu Gly Lys Gly Phe Pro Ile Ala Met Lys Thr Leu Asp
225                 230                 235                 240

Gly Gly Arg Ile Gly Ile Ala Ala Gln Ala Leu Gly Ile Ala Glu Gly
                245                 250                 255

Ala Phe Asn Glu Ala Arg Ala Tyr Met Lys Glu Arg Lys Gln Phe Gly
            260                 265                 270

Arg Ser Leu Asp Lys Phe Gln Gly Leu Ala Trp Met Met Ala Asp Met
        275                 280                 285

Asp Val Ala Ile Glu Ser Ala Arg Tyr Leu Val Tyr Lys Ala Ala Tyr

```
            290                 295                 300

Leu Lys Gln Ala Gly Leu Pro Tyr Thr Val Asp Ala Arg Ala Lys
305                 310                 315                 320

Leu His Ala Ala Asn Val Ala Met Asp Val Thr Lys Ala Val Gln
                325                 330                 335

Leu Phe Gly Gly Tyr Gly Tyr Thr Lys Asp Tyr Pro Val Glu Arg Met
            340                 345                 350

Met Arg Asp Ala Lys Ile Thr Glu Ile Tyr Glu Gly Thr Ser Glu Val
            355                 360                 365

Gln Lys Leu Val Ile Ser Gly Lys Ile Phe Arg
            370                 375

<210> SEQ ID NO 34
<211> LENGTH: 858
<212> TYPE: PRT
<213> ORGANISM: Clostridium acetobutylicum

<400> SEQUENCE: 34

Met Lys Val Thr Asn Gln Lys Glu Leu Lys Gln Lys Leu Asn Glu Leu
1               5                   10                  15

Arg Glu Ala Gln Lys Lys Phe Ala Thr Tyr Thr Gln Glu Gln Val Asp
            20                  25                  30

Lys Ile Phe Lys Gln Cys Ala Ile Ala Ala Lys Glu Arg Ile Asn
        35                  40                  45

Leu Ala Lys Leu Ala Val Glu Glu Thr Gly Ile Gly Leu Val Glu Asp
    50                  55                  60

Lys Ile Ile Lys Asn His Phe Ala Ala Glu Tyr Ile Tyr Asn Lys Tyr
65                  70                  75                  80

Lys Asn Glu Lys Thr Cys Gly Ile Ile Asp His Asp Asp Ser Leu Gly
                85                  90                  95

Ile Thr Lys Val Ala Glu Pro Ile Gly Ile Val Ala Ala Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Phe Phe Ser Pro His Pro Arg Ala Lys Lys
130                 135                 140

Ser Thr Ile Ala Ala Ala Lys Leu Ile Leu Asp Ala Ala Val Lys Ala
145                 150                 155                 160

Gly Ala Pro Lys Asn Ile Ile Gly Trp Ile Asp Glu Pro Ser Ile Glu
                165                 170                 175

Leu Ser Gln Asp Leu Met Ser Glu Ala Asp Ile Ile Leu Ala Thr Gly
            180                 185                 190

Gly Pro Ser Met Val Lys Ala Ala Tyr Ser Ser Gly Lys Pro Ala Ile
        195                 200                 205

Gly Val Gly Ala Gly Asn Thr Pro Ala Ile Ile Asp Glu Ser Ala Asp
    210                 215                 220

Ile Asp Met Ala Val Ser Ser Ile Ile Leu Ser Lys Thr Tyr Asp Asn
225                 230                 235                 240

Gly Val Ile Cys Ala Ser Glu Gln Ser Ile Leu Val Met Asn Ser Ile
                245                 250                 255

Tyr Glu Lys Val Lys Glu Glu Phe Val Lys Arg Gly Ser Tyr Ile Leu
            260                 265                 270

Asn Gln Asn Glu Ile Ala Lys Ile Lys Glu Thr Met Phe Lys Asn Gly
        275                 280                 285
```

-continued

Ala Ile Asn Ala Asp Ile Val Gly Lys Ser Ala Tyr Ile Ile Ala Lys
    290                 295                 300

Met Ala Gly Ile Glu Val Pro Gln Thr Thr Lys Ile Leu Ile Gly Glu
305                 310                 315                 320

Val Gln Ser Val Glu Lys Ser Glu Leu Phe Ser His Glu Lys Leu Ser
                325                 330                 335

Pro Val Leu Ala Met Tyr Lys Val Lys Asp Phe Asp Glu Ala Leu Lys
            340                 345                 350

Lys Ala Gln Arg Leu Ile Glu Leu Gly Gly Ser Gly His Thr Ser Ser
        355                 360                 365

Leu Tyr Ile Asp Ser Gln Asn Asn Lys Asp Lys Val Lys Glu Phe Gly
    370                 375                 380

Leu Ala Met Lys Thr Ser Arg Thr Phe Ile Asn Met Pro Ser Ser Gln
385                 390                 395                 400

Gly Ala Ser Gly Asp Leu Tyr Asn Phe Ala Ile Ala Pro Ser Phe Thr
                405                 410                 415

Leu Gly Cys Gly Thr Trp Gly Gly Asn Ser Val Ser Gln Asn Val Glu
            420                 425                 430

Pro Lys His Leu Leu Asn Ile Lys Ser Val Ala Glu Arg Arg Glu Asn
        435                 440                 445

Met Leu Trp Phe Lys Val Pro Gln Lys Ile Tyr Phe Lys Tyr Gly Cys
    450                 455                 460

Leu Arg Phe Ala Leu Lys Glu Leu Lys Asp Met Asn Lys Lys Arg Ala
465                 470                 475                 480

Phe Ile Val Thr Asp Lys Asp Leu Phe Lys Leu Gly Tyr Val Asn Lys
                485                 490                 495

Ile Thr Lys Val Leu Asp Glu Ile Asp Ile Lys Tyr Ser Ile Phe Thr
            500                 505                 510

Asp Ile Lys Ser Asp Pro Thr Ile Asp Ser Val Lys Lys Gly Ala Lys
        515                 520                 525

Glu Met Leu Asn Phe Glu Pro Asp Thr Ile Ile Ser Ile Gly Gly Gly
    530                 535                 540

Ser Pro Met Asp Ala Ala Lys Val Met His Leu Leu Tyr Glu Tyr Pro
545                 550                 555                 560

Glu Ala Glu Ile Glu Asn Leu Ala Ile Asn Phe Met Asp Ile Arg Lys
                565                 570                 575

Arg Ile Cys Asn Phe Pro Lys Leu Gly Thr Lys Ala Ile Ser Val Ala
            580                 585                 590

Ile Pro Thr Thr Ala Gly Thr Gly Ser Glu Ala Thr Pro Phe Ala Val
        595                 600                 605

Ile Thr Asn Asp Glu Thr Gly Met Lys Tyr Pro Leu Thr Ser Tyr Glu
    610                 615                 620

Leu Thr Pro Asn Met Ala Ile Ile Asp Thr Glu Leu Met Leu Asn Met
625                 630                 635                 640

Pro Arg Lys Leu Thr Ala Thr Gly Ile Asp Ala Leu Val His Ala
                645                 650                 655

Ile Glu Ala Tyr Val Ser Val Met Ala Thr Asp Tyr Thr Asp Glu Leu
            660                 665                 670

Ala Leu Arg Ala Ile Lys Met Ile Phe Lys Tyr Leu Pro Arg Ala Tyr
        675                 680                 685

Lys Asn Gly Thr Asn Asp Ile Glu Ala Arg Glu Lys Met Ala His Ala
    690                 695                 700

Ser Asn Ile Ala Gly Met Ala Phe Ala Asn Ala Phe Leu Gly Val Cys

```
                705                 710                 715                 720
His Ser Met Ala His Lys Leu Gly Ala Met His His Val Pro His Gly
                    725                 730                 735

Ile Ala Cys Ala Val Leu Ile Glu Glu Val Ile Lys Tyr Asn Ala Thr
                    740                 745                 750

Asp Cys Pro Thr Lys Gln Thr Ala Phe Pro Gln Tyr Lys Ser Pro Asn
                    755                 760                 765

Ala Lys Arg Lys Tyr Ala Glu Ile Ala Glu Tyr Leu Asn Leu Lys Gly
            770                 775                 780

Thr Ser Asp Thr Glu Lys Val Thr Ala Leu Ile Glu Ala Ile Ser Lys
785                 790                 795                 800

Leu Lys Ile Asp Leu Ser Ile Pro Gln Asn Ile Ser Ala Ala Gly Ile
                    805                 810                 815

Asn Lys Lys Asp Phe Tyr Asn Thr Leu Asp Lys Met Ser Glu Leu Ala
                    820                 825                 830

Phe Asp Asp Gln Cys Thr Thr Ala Asn Pro Arg Tyr Pro Leu Ile Ser
            835                 840                 845

Glu Leu Lys Asp Ile Tyr Ile Lys Ser Phe
            850                 855

<210> SEQ ID NO 35
<211> LENGTH: 862
<212> TYPE: PRT
<213> ORGANISM: Clostridium acetobutylicum

<400> SEQUENCE: 35

Met Lys Val Thr Thr Val Lys Glu Leu Asp Glu Lys Leu Lys Val Ile
1               5                   10                  15

Lys Glu Ala Gln Lys Lys Phe Ser Cys Tyr Ser Gln Glu Met Val Asp
            20                  25                  30

Glu Ile Phe Arg Asn Ala Ala Met Ala Ala Ile Asp Ala Arg Ile Glu
        35                  40                  45

Leu Ala Lys Ala Ala Val Leu Glu Thr Gly Met Gly Leu Val Glu Asp
    50                  55                  60

Lys Val Ile Lys Asn His Phe Ala Gly Glu Tyr Ile Tyr Asn Lys Tyr
65                  70                  75                  80

Lys Asp Glu Lys Thr Cys Gly Ile Ile Glu Arg Asn Glu Pro Tyr Gly
                85                  90                  95

Ile Thr Lys Ile Ala Glu Pro Ile Gly Val Val Ala Ala Ile Ile Pro
            100                 105                 110

Val Thr Asn Pro Thr Ser Thr Thr Ile Phe Lys Ser Leu Ile Ser Leu
        115                 120                 125

Lys Thr Arg Asn Gly Ile Phe Phe Ser Pro His Pro Arg Ala Lys Lys
    130                 135                 140

Ser Thr Ile Leu Ala Ala Lys Thr Ile Leu Asp Ala Ala Val Lys Ser
145                 150                 155                 160

Gly Ala Pro Glu Asn Ile Ile Gly Trp Ile Asp Glu Pro Ser Ile Glu
                165                 170                 175

Leu Thr Gln Tyr Leu Met Gln Lys Ala Asp Ile Thr Leu Ala Thr Gly
            180                 185                 190

Gly Pro Ser Leu Val Lys Ser Ala Tyr Ser Ser Gly Lys Pro Ala Ile
        195                 200                 205

Gly Val Gly Pro Gly Asn Thr Pro Val Ile Ile Asp Glu Ser Ala His
    210                 215                 220
```

-continued

```
Ile Lys Met Ala Val Ser Ser Ile Ile Leu Ser Lys Thr Tyr Asp Asn
225                 230                 235                 240

Gly Val Ile Cys Ala Ser Glu Gln Ser Val Ile Val Leu Lys Ser Ile
            245                 250                 255

Tyr Asn Lys Val Lys Asp Glu Phe Gln Glu Arg Gly Ala Tyr Ile Ile
        260                 265                 270

Lys Lys Asn Glu Leu Asp Lys Val Arg Glu Val Ile Phe Lys Asp Gly
    275                 280                 285

Ser Val Asn Pro Lys Ile Val Gly Gln Ser Ala Tyr Thr Ile Ala Ala
290                 295                 300

Met Ala Gly Ile Lys Val Pro Lys Thr Thr Arg Ile Leu Ile Gly Glu
305                 310                 315                 320

Val Thr Ser Leu Gly Glu Glu Pro Phe Ala His Glu Lys Leu Ser
            325                 330                 335

Pro Val Leu Ala Met Tyr Glu Ala Asp Asn Phe Asp Asp Ala Leu Lys
            340                 345                 350

Lys Ala Val Thr Leu Ile Asn Leu Gly Leu Gly His Thr Ser Gly
        355                 360                 365

Ile Tyr Ala Asp Glu Ile Lys Ala Arg Asp Lys Ile Asp Arg Phe Ser
370                 375                 380

Ser Ala Met Lys Thr Val Arg Thr Phe Val Asn Ile Pro Thr Ser Gln
385                 390                 395                 400

Gly Ala Ser Gly Asp Leu Tyr Asn Phe Arg Ile Pro Pro Ser Phe Thr
            405                 410                 415

Leu Gly Cys Gly Phe Trp Gly Gly Asn Ser Val Ser Glu Asn Val Gly
            420                 425                 430

Pro Lys His Leu Leu Asn Ile Lys Thr Val Ala Glu Arg Arg Glu Asn
            435                 440                 445

Met Leu Trp Phe Arg Val Pro His Lys Val Tyr Phe Lys Phe Gly Cys
    450                 455                 460

Leu Gln Phe Ala Leu Lys Asp Leu Lys Asp Leu Lys Lys Lys Arg Ala
465                 470                 475                 480

Phe Ile Val Thr Asp Ser Asp Pro Tyr Asn Leu Asn Tyr Val Asp Ser
            485                 490                 495

Ile Ile Lys Ile Leu Glu His Leu Asp Ile Asp Phe Lys Val Phe Asn
            500                 505                 510

Lys Val Gly Arg Glu Ala Asp Leu Lys Thr Ile Lys Lys Ala Thr Glu
        515                 520                 525

Glu Met Ser Ser Phe Met Pro Asp Thr Ile Ile Ala Leu Gly Gly Thr
    530                 535                 540

Pro Glu Met Ser Ser Ala Lys Leu Met Trp Val Leu Tyr Glu His Pro
545                 550                 555                 560

Glu Val Lys Phe Glu Asp Leu Ala Ile Lys Phe Met Asp Ile Arg Lys
            565                 570                 575

Arg Ile Tyr Thr Phe Pro Lys Leu Gly Lys Lys Ala Met Leu Val Ala
        580                 585                 590

Ile Thr Thr Ser Ala Gly Ser Gly Ser Glu Val Thr Pro Phe Ala Leu
    595                 600                 605

Val Thr Asp Asn Asn Thr Gly Asn Lys Tyr Met Leu Ala Asp Tyr Glu
        610                 615                 620

Met Thr Pro Asn Met Ala Ile Val Asp Ala Glu Leu Met Met Lys Met
625                 630                 635                 640

Pro Lys Gly Leu Thr Ala Tyr Ser Gly Ile Asp Ala Leu Val Asn Ser
```

```
                    645                 650                 655
Ile Glu Ala Tyr Thr Ser Val Tyr Ala Ser Glu Tyr Thr Asn Gly Leu
                660                 665                 670

Ala Leu Glu Ala Ile Arg Leu Ile Phe Lys Tyr Leu Pro Glu Ala Tyr
            675                 680                 685

Lys Asn Gly Arg Thr Asn Glu Lys Ala Arg Glu Lys Met Ala His Ala
        690                 695                 700

Ser Thr Met Ala Gly Met Ala Ser Ala Asn Ala Phe Leu Gly Leu Cys
705                 710                 715                 720

His Ser Met Ala Ile Lys Leu Ser Ser Glu His Asn Ile Pro Ser Gly
                725                 730                 735

Ile Ala Asn Ala Leu Leu Ile Glu Glu Val Ile Lys Phe Asn Ala Val
            740                 745                 750

Asp Asn Pro Val Lys Gln Ala Pro Cys Pro Gln Tyr Lys Tyr Pro Asn
        755                 760                 765

Thr Ile Phe Arg Tyr Ala Arg Ile Ala Asp Tyr Ile Lys Leu Gly Gly
    770                 775                 780

Asn Thr Asp Glu Glu Lys Val Asp Leu Leu Ile Asn Lys Ile His Glu
785                 790                 795                 800

Leu Lys Lys Ala Leu Asn Ile Pro Thr Ser Ile Lys Asp Ala Gly Val
                805                 810                 815

Leu Glu Glu Asn Phe Tyr Ser Ser Leu Asp Arg Ile Ser Glu Leu Ala
            820                 825                 830

Leu Asp Asp Gln Cys Thr Gly Ala Asn Pro Arg Phe Pro Leu Thr Ser
        835                 840                 845

Glu Ile Lys Glu Met Tyr Ile Asn Cys Phe Lys Lys Gln Pro
    850                 855                 860

<210> SEQ ID NO 36
<211> LENGTH: 389
<212> TYPE: PRT
<213> ORGANISM: Clostridium acetobutylicum

<400> SEQUENCE: 36

Met Leu Ser Phe Asp Tyr Ser Ile Pro Thr Lys Val Phe Phe Gly Lys
1               5                   10                  15

Gly Lys Ile Asp Val Ile Gly Glu Glu Ile Lys Lys Tyr Gly Ser Arg
            20                  25                  30

Val Leu Ile Val Tyr Gly Gly Gly Ser Ile Lys Arg Asn Gly Ile Tyr
        35                  40                  45

Asp Arg Ala Thr Ala Ile Leu Lys Glu Asn Asn Ile Ala Phe Tyr Glu
    50                  55                  60

Leu Ser Gly Val Glu Pro Asn Pro Arg Ile Thr Thr Val Lys Lys Gly
65                  70                  75                  80

Ile Glu Ile Cys Arg Glu Asn Asn Val Asp Leu Val Leu Ala Ile Gly
                85                  90                  95

Gly Gly Ser Ala Ile Asp Cys Ser Lys Val Ile Ala Ala Gly Val Tyr
            100                 105                 110

Tyr Asp Gly Asp Thr Trp Asp Met Val Lys Asp Pro Ser Lys Ile Thr
        115                 120                 125

Lys Val Leu Pro Ile Ala Ser Ile Leu Thr Leu Ser Ala Thr Gly Ser
    130                 135                 140

Glu Met Asp Gln Ile Ala Val Ile Ser Asn Met Glu Thr Asn Glu Lys
145                 150                 155                 160
```

```
Leu Gly Val Gly His Asp Asp Met Arg Pro Lys Phe Ser Val Leu Asp
            165                 170                 175

Pro Thr Tyr Thr Phe Thr Val Pro Lys Asn Gln Thr Ala Ala Gly Thr
            180                 185                 190

Ala Asp Ile Met Ser His Thr Phe Glu Ser Tyr Phe Ser Gly Val Glu
            195                 200                 205

Gly Ala Tyr Val Gln Asp Gly Ile Ala Glu Ala Ile Leu Arg Thr Cys
    210                 215                 220

Ile Lys Tyr Gly Lys Ile Ala Met Glu Lys Thr Asp Asp Tyr Glu Ala
225                 230                 235                 240

Arg Ala Asn Leu Met Trp Ala Ser Ser Leu Ala Ile Asn Gly Leu Leu
                245                 250                 255

Ser Leu Gly Lys Asp Arg Lys Trp Ser Cys His Pro Met Glu His Glu
            260                 265                 270

Leu Ser Ala Tyr Tyr Asp Ile Thr His Gly Val Gly Leu Ala Ile Leu
            275                 280                 285

Thr Pro Asn Trp Met Glu Tyr Ile Leu Asn Asp Asp Thr Leu His Lys
            290                 295                 300

Phe Val Ser Tyr Gly Ile Asn Val Trp Gly Ile Asp Lys Asn Lys Asp
305                 310                 315                 320

Asn Tyr Glu Ile Ala Arg Glu Ala Ile Lys Asn Thr Arg Glu Tyr Phe
                325                 330                 335

Asn Ser Leu Gly Ile Pro Ser Lys Leu Arg Glu Val Gly Ile Gly Lys
            340                 345                 350

Asp Lys Leu Glu Leu Met Ala Lys Gln Ala Val Arg Asn Ser Gly Gly
            355                 360                 365

Thr Ile Gly Ser Leu Arg Pro Ile Asn Ala Glu Asp Val Leu Glu Ile
            370                 375                 380

Phe Lys Lys Ser Tyr
385

<210> SEQ ID NO 37
<211> LENGTH: 390
<212> TYPE: PRT
<213> ORGANISM: Clostridium acetobutylicum

<400> SEQUENCE: 37

Met Val Asp Phe Glu Tyr Ser Ile Pro Thr Arg Ile Phe Phe Gly Lys
1               5                   10                  15

Asp Lys Ile Asn Val Leu Gly Arg Glu Leu Lys Lys Tyr Gly Ser Lys
            20                  25                  30

Val Leu Ile Val Tyr Gly Gly Gly Ser Ile Lys Arg Asn Gly Ile Tyr
        35                  40                  45

Asp Lys Ala Val Ser Ile Leu Glu Lys Asn Ser Ile Lys Phe Tyr Glu
    50                  55                  60

Leu Ala Gly Val Glu Pro Asn Pro Arg Val Thr Thr Val Glu Lys Gly
65                  70                  75                  80

Val Lys Ile Cys Arg Glu Asn Gly Val Glu Val Val Leu Ala Ile Gly
                85                  90                  95

Gly Gly Ser Ala Ile Asp Cys Ala Lys Val Ile Ala Ala Ala Cys Glu
            100                 105                 110

Tyr Asp Gly Asn Pro Trp Asp Ile Val Leu Asp Gly Ser Lys Ile Lys
        115                 120                 125

Arg Val Leu Pro Ile Ala Ser Ile Leu Thr Ile Ala Ala Thr Gly Ser
    130                 135                 140
```

Glu Met Asp Thr Trp Ala Val Ile Asn Asn Met Asp Thr Asn Glu Lys
145                 150                 155                 160

Leu Ile Ala Ala His Pro Asp Met Ala Pro Lys Phe Ser Ile Leu Asp
            165                 170                 175

Pro Thr Tyr Thr Tyr Thr Val Pro Thr Asn Gln Thr Ala Ala Gly Thr
        180                 185                 190

Ala Asp Ile Met Ser His Ile Phe Glu Val Tyr Phe Ser Asn Thr Lys
        195                 200                 205

Thr Ala Tyr Leu Gln Asp Arg Met Ala Glu Ala Leu Leu Arg Thr Cys
    210                 215                 220

Ile Lys Tyr Gly Gly Ile Ala Leu Glu Lys Pro Asp Asp Tyr Glu Ala
225                 230                 235                 240

Arg Ala Asn Leu Met Trp Ala Ser Ser Leu Ala Ile Asn Gly Leu Leu
                245                 250                 255

Thr Tyr Gly Lys Asp Thr Asn Trp Ser Val His Leu Met Glu His Glu
            260                 265                 270

Leu Ser Ala Tyr Tyr Asp Ile Thr His Gly Val Gly Leu Ala Ile Leu
        275                 280                 285

Thr Pro Asn Trp Met Glu Tyr Ile Leu Asn Asn Asp Thr Val Tyr Lys
    290                 295                 300

Phe Val Glu Tyr Gly Val Asn Val Trp Gly Ile Asp Lys Glu Lys Asn
305                 310                 315                 320

His Tyr Asp Ile Ala His Gln Ala Ile Gln Lys Thr Arg Asp Tyr Phe
                325                 330                 335

Val Asn Val Leu Gly Leu Pro Ser Arg Leu Arg Asp Val Gly Ile Glu
            340                 345                 350

Glu Glu Lys Leu Asp Ile Met Ala Lys Glu Ser Val Lys Leu Thr Gly
        355                 360                 365

Gly Thr Ile Gly Asn Leu Arg Pro Val Asn Ala Ser Glu Val Leu Gln
    370                 375                 380

Ile Phe Lys Lys Ser Val
385                 390

<210> SEQ ID NO 38
<211> LENGTH: 336
<212> TYPE: PRT
<213> ORGANISM: Clostridium acetobutylicum

<400> SEQUENCE: 38

Met Asn Lys Ala Asp Tyr Lys Gly Val Trp Val Phe Ala Glu Gln Arg
1               5                   10                  15

Asp Gly Glu Leu Gln Lys Val Ser Leu Glu Leu Leu Gly Lys Gly Lys
            20                  25                  30

Glu Met Ala Glu Lys Leu Gly Val Glu Leu Thr Ala Val Leu Leu Gly
        35                  40                  45

His Asn Thr Glu Lys Met Ser Lys Asp Leu Leu Ser His Gly Ala Asp
    50                  55                  60

Lys Val Leu Ala Ala Asp Asn Glu Leu Leu Ala His Phe Ser Thr Asp
65                  70                  75                  80

Gly Tyr Ala Lys Val Ile Cys Asp Leu Val Asn Glu Arg Lys Pro Glu
                85                  90                  95

Ile Leu Phe Ile Gly Ala Thr Phe Ile Gly Arg Asp Leu Gly Pro Arg
            100                 105                 110

Ile Ala Ala Arg Leu Ser Thr Gly Leu Thr Ala Asp Cys Thr Ser Leu

```
              115                 120                 125
Asp Ile Asp Val Glu Asn Arg Asp Leu Leu Ala Thr Arg Pro Ala Phe
    130                 135                 140

Gly Gly Asn Leu Ile Ala Thr Ile Val Cys Ser Asp His Arg Pro Gln
145                 150                 155                 160

Met Ala Thr Val Arg Pro Gly Val Phe Glu Lys Leu Pro Val Asn Asp
                165                 170                 175

Ala Asn Val Ser Asp Asp Lys Ile Glu Lys Val Ala Ile Lys Leu Thr
            180                 185                 190

Ala Ser Asp Ile Arg Thr Lys Val Ser Lys Val Val Lys Leu Ala Lys
        195                 200                 205

Asp Ile Ala Asp Ile Gly Glu Ala Lys Val Leu Val Ala Gly Gly Arg
    210                 215                 220

Gly Val Gly Ser Lys Glu Asn Phe Glu Lys Leu Glu Glu Leu Ala Ser
225                 230                 235                 240

Leu Leu Gly Gly Thr Ile Ala Ala Ser Arg Ala Ala Ile Glu Lys Glu
                245                 250                 255

Trp Val Asp Lys Asp Leu Gln Val Gly Gln Thr Gly Lys Thr Val Arg
            260                 265                 270

Pro Thr Leu Tyr Ile Ala Cys Gly Ile Ser Gly Ala Ile Gln His Leu
        275                 280                 285

Ala Gly Met Gln Asp Ser Asp Tyr Ile Ile Ala Ile Asn Lys Asp Val
    290                 295                 300

Glu Ala Pro Ile Met Lys Val Ala Asp Leu Ala Ile Val Gly Asp Val
305                 310                 315                 320

Asn Lys Val Val Pro Glu Leu Ile Ala Gln Val Lys Ala Ala Asn Asn
                325                 330                 335

<210> SEQ ID NO 39
<211> LENGTH: 259
<212> TYPE: PRT
<213> ORGANISM: Clostridium acetobutylicum

<400> SEQUENCE: 39

Met Asn Ile Val Val Cys Leu Lys Gln Val Pro Asp Thr Ala Glu Val
1               5                   10                  15

Arg Ile Asp Pro Val Lys Gly Thr Leu Ile Arg Glu Gly Val Pro Ser
                20                  25                  30

Ile Ile Asn Pro Asp Asp Lys Asn Ala Leu Glu Glu Ala Leu Val Leu
            35                  40                  45

Lys Asp Asn Tyr Gly Ala His Val Thr Val Ile Ser Met Gly Pro Pro
50                  55                  60

Gln Ala Lys Asn Ala Leu Val Glu Ala Leu Ala Met Gly Ala Asp Glu
65                  70                  75                  80

Ala Val Leu Leu Thr Asp Arg Ala Phe Gly Gly Ala Asp Thr Leu Ala
                85                  90                  95

Thr Ser His Thr Ile Ala Ala Gly Ile Lys Lys Leu Lys Tyr Asp Ile
            100                 105                 110

Val Phe Ala Gly Arg Gln Ala Ile Asp Gly Asp Thr Ala Gln Val Gly
        115                 120                 125

Pro Glu Ile Ala Glu His Leu Gly Ile Pro Gln Val Thr Tyr Val Glu
    130                 135                 140

Lys Val Glu Val Asp Gly Asp Thr Leu Lys Ile Arg Lys Ala Trp Glu
145                 150                 155                 160
```

Asp Gly Tyr Glu Val Val Glu Val Lys Thr Pro Val Leu Leu Thr Ala
              165                 170                 175

Ile Lys Glu Leu Asn Val Pro Arg Tyr Met Ser Val Glu Lys Ile Phe
        180                 185                 190

Gly Ala Phe Asp Lys Glu Val Lys Met Trp Thr Ala Asp Asp Ile Asp
        195                 200                 205

Val Asp Lys Ala Asn Leu Gly Leu Lys Gly Ser Pro Thr Lys Val Lys
        210                 215                 220

Lys Ser Ser Thr Lys Glu Val Lys Gly Gln Gly Glu Val Ile Asp Lys
225                 230                 235                 240

Pro Val Lys Glu Ala Ala Ala Tyr Val Val Ser Lys Leu Lys Glu Glu
                245                 250                 255

His Tyr Ile

<210> SEQ ID NO 40
<211> LENGTH: 5976
<212> TYPE: DNA
<213> ORGANISM: Artificial
<220> FEATURE:
<223> OTHER INFORMATION: plasmid YEplac112PtdhTadh

<400> SEQUENCE: 40
gcccggggga tccactagtt ctagaatccg tcgaaactaa gttctggtgt tttaaaacta      60
aaaaaaagac taactataaa agtagaattt aagaagttta agaaatagat ttacagaatt     120
acaatcaata cctaccgtct ttatatactt attagtcaag taggggaata atttcaggga     180
actggtttca accttttttt tcagcttttt ccaaatcaga gagagcagaa ggtaatagaa     240
ggtgtaagaa aatgagatag atacatgcgt gggtcaattg ccttgtgtca tcatttactc     300
caggcaggtt gcatcactcc attgaggttg tgcccgtttt ttgcctgttt gtgcccctgt     360
tctctgtagt tgcgctaaga gaatggacct atgaactgat ggttggtgaa gaaaacaata     420
ttttggtgct gggattcttt tttttttctgg atgccagctt aaaaagcggg ctccattata     480
tttagtggat gccaggaata aactgttcac ccagacacct acgatgttat atattctgtg     540
taacccgccc cctatttttgg gcatgtacgg gttacagcag aattaaaagg ctaatttttt     600
gactaaataa agttaggaaa atcactacta ttaattattt acgtattctt tgaaatggcg     660
agtattgata atgataaact gagctcgaat tcactggccg tcgttttaca acgtcgtgac     720
tgggaaaacc ctggcgttac ccaacttaat cgccttgcag cacatccccc tttcgccagc     780
tggcgtaata gcgaagaggc ccgcaccgat cgcccttccc aacagttgcg cagcctgaat     840
ggcgaatggc gcctgatgcg gtattttctc cttacgcatc tgtgcggtat ttcacaccgc     900
atatatcgga tcgtacttgt tacccatcat tgaattttga acatccgaac ctgggagttt     960
tccctgaaac agatagtata tttgaacctg tataataata tatagtctag cgctttacgg    1020
aagacaatgt atgtatttcg gttcctggag aaactattgc atctattgca taggtaatct    1080
tgcacgtcgc atccccggtt catttctgc gtttccatct tgcacttcaa tagcatatct    1140
ttgttaacga agcatctgtg cttcattttg tagaacaaaa atgcaacgcg agagcgctaa    1200
tttttcaaac aaagaatctg agctgcattt ttacagaaca gaaatgcaac gcgaaagcgc    1260
tattttacca cgaagaatc tgtgcttcat ttttgtaaaa caaaaatgca acgcgagagc    1320 gctaatttt caaacaaaga atctgagctg cattttttaca gaacagaaat gcaacgcgag    1380
agcgctattt taccaacaaa gaatctatac ttcttttttg ttctacaaaa atgcatcccg    1440
agagcgctat ttttctaaca aagcatctta gattactttt tttctccttt gtgcgctcta    1500

```
taatgcagtc tcttgataac ttttttgcact gtaggtccgt taaggttaga agaaggctac    1560
tttggtgtct attttctctt ccataaaaaa agcctgactc cacttcccgc gtttactgat    1620
tactagcgaa gctgcgggtg cattttttca agataaaggc atccccgatt atattctata    1680
ccgatgtgga ttgcgcatac tttgtgaaca gaaagtgata gcgttgatga ttcttcattg    1740
gtcagaaaat tatgaacggt ttcttctatt ttgtctctat atactacgta taggaaatgt    1800
ttacattttc gtattgtttt cgattcactc tatgaatagt tcttactaca attttttgt     1860 ctaaagagta atactagaga taaacataaa aaatgtagag gtcgagttta gatgcaagtt    1920
caaggagcga aaggtggatg ggtaggttat atagggatat agcacagaga tatatagcaa    1980
agagatactt ttgagcaatg tttgtggaag cggtattcgc aatattttag tagctcgtta    2040
cagtccggtg cgttttggt tttttgaaag tgcgtcttca gagcgctttt ggttttcaaa     2100
agcgctctga agttcctata ctttctagct agagaatagg aacttcggaa taggaacttc    2160
aaagcgtttc cgaaaacgag cgcttccgaa aatgcaacgc gagctgcgca catacagctc    2220
actgttcacg tcgcacctat atctgcgtgt tgcctgtata tatatataca tgagaagaac    2280
ggcatagtgc gtgtttatgc ttaaatgcgt acttatatgc gtctatttat gtaggatgaa    2340
aggtagtcta gtacctcctg tgatattatc ccattccatg cggggtatcg tatgcttcct    2400
tcagcactac cctttagctg ttctatatgc tgccactcct caattggatt agtctcatcc    2460
ttcaatgcta tcatttcctt tgatattgga tcgatccgat gataagctgt caaacatgag    2520
aattgatctt ttatgcttgc ttttcaaaag gcttgcaggc aagtgcacaa acaatactta    2580
aataaatact actcagtaat aacctatttc ttagcatttt tgacgaaatt tgctattttg    2640
ttagagtctt ttacaccatt tgtctccaca cctccgctta catcaacacc aataacgcca    2700
tttaatctaa gcgcatcacc aacatttttct ggcgtcagtc caccagctaa cataaaatgt    2760
aagctctcgg ggctctcttg ccttccaacc cagtcagaaa tcgagttcca atccaaaagt    2820
tcacctgtcc cacctgcttc tgaatcaaac aagggaataa acgaatgagg tttctgtgaa    2880
gctgcactga gtagtatgtt gcagtctttt ggaaatacga gtcttttaat aactggcaaa    2940
ccgaggaact cttggtattc ttgccacgac tcatctccat gcagttggac gatatcaatg    3000
ccgtaatcat tgaccagagc caaaacatcc tccttaggtt gattacgaaa cacgccaacc    3060
aagtatttcg gagtgcctga actattttta tatgctttta caagacttga aatttttcctt   3120 gcaataaccg ggtcaattgt tctctttcta ttgggcacac atataatacc cagcaagtca    3180
gcatcggaat ctagtgcaca ttctgcggcc tctgtgctct gcaagccgca aacttttcacc   3240 aatggaccag aactacctgt gaaattaata acagacatac tccaagctgc ctttgtgtgc    3300
ttaatcacgt atactcacgt gctcaatagt caccaatgcc ctccctcttg gccctctcct    3360
tttctttttt cgaccgaatt aattcttgaa gacgaaaggg cctcgtgata cgcctatttt    3420
tataggttaa tgtcatgata ataatggttt cttagacgtc aggtggcact tttcggggaa    3480
atgtgcgcgg aaccctatt tgtttatttt tctaaataca ttcaaatatg tatccgctca    3540
tgagacaata accctgataa atgcttcaat aatattgaaa aaggaagagt atgagtattc    3600
aacatttccg tgtcgccctt attccctttt ttgcggcatt tgccttcct gtttttgctc     3660 acccagaaac gctggtgaaa gtaaaagatg ctgaagatca gttgggtgca cgagtgggtt    3720
acatcgaact ggatctcaac agcggtaaga tccttgagag ttttcgcccc gaagaacgtt    3780
ttccaatgat gagcactttt aaagttctgc tatgtggcgc ggtattatcc cgtattgacg    3840
```

```
ccgggcaaga gcaactcggt cgccgcatac actattctca gaatgacttg gttgagtact      3900
caccagtcac agaaaagcat cttacggatg gcatgacagt aagagaatta tgcagtgctg      3960
ccataaccat gagtgataac actgcggcca acttacttct gacaacgatc ggaggaccga      4020
aggagctaac cgcttttttg cacaacatgg ggatcatgt aactcgcctt gatcgttggg       4080
aaccggagct gaatgaagcc ataccaaacg acgagcgtga caccacgatg cctgtagcaa      4140
tggcaacaac gttgcgcaaa ctattaactg gcgaactact tactctagct tcccggcaac      4200
aattaataga ctggatggag gcggataaag ttgcaggacc acttctgcgc tcggcccttc      4260
cggctggctg gtttattgct gataaatctg gagccggtga gcgtgggtct cgcggtatca      4320
ttgcagcact ggggccagat ggtaagccct cccgtatcgt agttatctac acgacgggga     4380
gtcaggcaac tatggatgaa cgaaatagac agatcgctga gataggtgcc tcactgatta     4440
agcattggta actgtcagac caagtttact catatatact ttagattgat ttaaaacttc     4500
attttttaatt taaaaggatc taggtgaaga tccttttttga taatctcatg accaaaatcc    4560
cttaacgtga gttttcgttc cactgagcgt cagaccccgt agaaaagatc aaaggatctt     4620
cttgagatcc ttttttttctg cgcgtaatct gctgcttgca acaaaaaaa ccaccgctac     4680
cagcggtggt ttgtttgccg gatcaagagc taccaactct ttttccgaag gtaactggct     4740
tcagcagagc gcagatacca atactgtcc ttctagtgta gccgtagtta ggccaccact      4800
tcaagaactc tgtagcaccg cctacatacc tcgctctgct aatcctgtta ccagtggctg     4860
ctgccagtgg cgataagtcg tgtcttaccg ggttggactc aagacgatag ttaccggata    4920
aggcgcagcg gtcgggctga acgggggggtt cgtgcacaca gcccagcttg gagcgaacga   4980
cctacaccga actgagatac ctacagcgtg agctatgaga aagcgccacg cttcccgaag    5040
ggagaaaggc ggacaggtat ccggtaagcg gcagggtcgg aacaggagag cgcacgaggg    5100
agcttccagg gggaaacgcc tggtatcttt atagtcctgt cgggtttcgc cacctctgac    5160
ttgagcgtcg atttttgtga tgctcgtcag ggggggcggag cctatggaaa aacgccagca   5220
acgcggcctt tttacggttc ctggcctttt gctggccttt tgctcacatg ttctttcctg    5280
cgttatcccc tgattctgtg gataaccgta ttaccgcctt tgagtgagct gataccgctc    5340
gccgcagccg aacgaccgag cgcagcgagt cagtgagcga ggaagcggaa gagcgcccaa    5400
tacgcaaacc gcctctcccc gcgcgttggc cgattcatta atgcagctgg cacgacaggt    5460
ttcccgactg gaaagcgggc agtgagcgca acgcaattaa tgtgagttag ctcactcatt    5520
aggcaccccca ggctttacac tttatgcttc cggctcgtat gttgtgtgga attgtgagcg   5580
gataacaatt tcacacagga aacagctatg accatgatta cgccaagctt aggcctgtgt    5640
ggaagaacga ttcaacagg tgttgtcctc tgaggacata aaatacacac cgagattcat     5700
caactcattg ctggagttag catatctaca attgggtgaa atggggagcg atttgcaggc    5760
atttgctcgg catgccggta gaggtgtggt caataagagc gacctcatgc tatacctgag    5820
aaagcaacct gacctacagg aaagagttac tcaagaataa gaattttcgt tttaaaacct   5880
aagagtcact ttaaaatttg tatacactta tttttttttat aacttattta ataataaaaa   5940
tcataaatca taagaaattc gctcgagtcg actgca                                5976
```

<210> SEQ ID NO 41
<211> LENGTH: 13286
<212> TYPE: DNA
<213> ORGANISM: Artificial
<220> FEATURE:
<223> OTHER INFORMATION: pBOL34

<400> SEQUENCE: 41

```
aagcttgcat gcctgcaggt cgacggcgcg ccgggcccgt ttaaacggcc ggccaaggtg      60
agacgcgcat aaccgctaga gtactttgaa gaggaaacag caatagggtt gctaccagta     120
taaatagaca ggtacataca acactggaaa tggttgtctg tttgagtacg ctttcaattc     180
atttgggtgt gcactttatt atgttacaat atggaaggga actttacact tctcctatgc     240
acatatatta attaaagtcc aatgctagta gagaaggggg gtaacacccc tccgcgctct     300
tttccgattt ttttctaaac cgtggaatat ttcggatatc cttttgttgt ttccgggtgt     360
acaatatgga cttcctcttt tctggcaacc aaacccatac atcgggattc ctataatacc     420
ttcgttggtc tccctaacat gtaggtggcg gaggggagat atacaataga acagatacca     480
gacaagacat aatgggctaa acaagactac accaattaca ctgcctcatt gatggtggta     540
cataacgaac taatactgta gccctagact tgatagccat catcatatcg aagtttcact     600
acccttttc catttgccat ctattgaagt aataataggc gcatgcaact tctttctttt     660
tttttctttt tctctctccc ccgttgttgt ctcaccatat ccgcaatgac aaaaaaatga     720
tggaagacac taaaggaaaa aattaacgac aaagacagca ccaacagatg tcgttgttcc     780
agagctgatg aggggtatct cgaagcacac gaaacttttt ccttccttca ttcacgcaca     840
ctactctcta atgagcaacg gtatacggcc ttccttccag ttacttgaat ttgaaataaa     900
aaaaagtttg ctgtcttgct atcaagtata aatagacctg caattattaa tcttttgttt     960
cctcgtcatt gttctcgttc cctttcttcc ttgtttcttt ttctgcacaa tatttcaagc    1020
tataccaagc atacaatcaa ctatctcata tacaatgaag gaagttgtta ttgcttctgc    1080
tgtcagaact gccattggtt cttacggtaa gtctttgaag gacgtcccag ctgtcgactt    1140
gggtgctacc gccatcaagg aagctgtcaa gaaggctggt atcaagccag aagatgttaa    1200
cgaagttatc ttaggtaacg ttttgcaagc tggtttaggt caaaacccag ctcgtcaagc    1260
ttcttcaag gctggtttgc cagttgaaat tccagccatg accatcaaca aggtttgtgg    1320
ttctggtttg agaactgttt ctttggctgc tcaaatcatc aaggctggtg acgctgatgt    1380
catcattgct ggtggtatgg aaaacatgtc cagagctcca tacttggcta acaatgctag    1440
atgggggttac agaatgggta acgccaagtt cgtcgatgaa atgatcactg acggtttatg    1500
ggacgctttc aacgactacc acatgggtat cactgctgaa acattgctg aaagatggaa    1560
catctccaga gaagaacaag atgaatttgc tttggcttct caaaagaagg ctgaagaagc    1620
catcaaatct ggtcaattca aggacgaaat tgtcccagtt gtcatcaagg gtagaaaggg    1680
tgaaaccgtt gtcgacaccg atgaacaccc aagattcggt tccaccattg aaggtttggc    1740
caagttgaaa ccagctttca gaaggatgg taccgtcact gctggtaacg cttccggttt    1800
gaacgactgt gctgctgttt tggttatcat gtctgctgaa aaggccaagg aattgggtgt    1860
caagccattg gccaagattg tctcctacgg ttctgctggt gttgacccag ccatcatggg    1920
ttacggtcct ttctacgcta ccaaggctgc tatcgaaaag gctggttgga ccgttgacga    1980
attggatttg attgaatcca acgaagcttt cgctgctcaa tctttggctg ttgccaagga    2040
cttgaaattc gacatgaaca aggtcaacgt taacggtggt gccattgctt gggtcaccc    2100
aattggtgct tccggtgcca gaatcttggt tactttagtc cacgctatgc aaaagcgtga    2160
tgccaagaag ggtttggcta ctctctatgt at cggtggtggt caaggtactg ccatcttatt    2220
ggaaaagtgt taggcccggg cataaagcaa tcttgatgag gataatgatt ttttttgaa    2280
```

```
tatacataaa tactaccgtt tttctgctag attttgtgaa gacgtaaata agtacatatt    2340 acttttttaag ccaagacaag attaagcatt aactttaccc tttctcttc taagtttcaa    2400 tactagttat cactgtttaa agttatggc gagaacgtcg gcggttaaaa tatattaccc     2460
tgaacgtggt gaattgaagt tctaggatgg tttaaagatt tttccttttt gggaaataag   2520
taaacaatat attgctgcct tgcaaaacg cacatacccca caatatgtga ctattggcaa   2580
agaacgcatt atcctttgaa gaggtggata ctgatactaa gagagtctct attccggctc   2640 cactttttagt ccagagatta cttgtcttct tacgtatcag aacaagaaag catttccaaa 2700
gtaattgcat ttgcccttga gcagtatata tatactaaga agtttaaaca tttaaacgtg  2760
tgtgtgcatt atatatatta aaaattaaga attagactaa ataaagtgtt tctaaaaaaa 2820
tattaaagtt gaaatgtgcg tgttgtgaat tgtgctctat tagaataatt atgacttgtg  2880
tgcgtttcat attttaaaat aggaaataac caagaaagaa aaagtaccat ccagagaaac  2940
caattatatc aaatcaaata aaacaaccag cttcggtgtg tgtgtgtgtg tgaagctaag  3000
agttgatgcc atttaatcta aaaattttaa ggtgtgtgtg tggataaaat attagaatga  3060
caattcgaga tgaaatttta agcaaactct agtaggaaat aagcggctta ttcttgttgg  3120
ctcctaattc ttttttagtgt atcagttccc attgataaaa aaattaaaat taaaattaga  3180
aaaattaaac cagaaaaatc aagttgatta aaatgtgaca aaaattatga ttaaatgcta  3240
cttcaacagg agcccgggcc tatttggagt agtcgtagaa acccttacca gacttttctac 3300 ctaaccaacc agctctaacg tacttcttca ataaagtgtg aggtctgtac ttagagtcac  3360
cggtttcaga gtataagaca tccatgatgg ccaaacagat atccaaaccg atgaagtcac  3420
ctaattccaa tggacccatt gggtggttag cacccaattt catggccttg tcgatatctt   3480
caacagaagc aataccttca gccaaaatac cgacagcttc gttgatcatt ggaatcaaga  3540
ttctgttgac aacgaaacct ggagcttcag caacttcaac tgggtcctta ccaatggcaa  3600
tggaagtttc cttgacagca tcgaaagttt cttgagaggt ggcaatacct ctgatgactt  3660
cgaccaactt catgactgga gctgggttga agaagtgcat accgataacc ttgtctggtc   3720
tcttggtagc agaagcaact tcagtgatgg acaaagaaga agtgttggaa gccaaaatgg   3780
tttctggctt acagatgttg tccaaatcag caaagatttg cttcttgatg tccattcttt  3840
caacggcagc ttcaatgacc aaatcacagt cagcagccat gttcaagtca acagtaccgg   3900
agattctggt caagatttcg accttggtag cttcttcaat cttacccttc ttgaccaact   3960
tggacaagtt cttgttgatg aaatccaaac cacggtcaac gaattcgtcc ttgatatctc   4020
tcaaaacaac ttcgaaaccc ttggcagcga agcttgagc aataccagaa cccatggtac    4080
cggcaccaat gacacaaacc ttcttcattt tgatttagtg tttgtgtgtt gataagcagt   4140
tgcttggttt tttatgaaaa atagctagaa ggaataaggg attacaagag agatgttaca  4200
agaaagaagt aaaataaatt tgattaatat tgccattatc aaaagctatt tatatgttga  4260
aatcgtggag atcatgtgtg ccagaaaagg ccacagtttc cggggagagg cataccttga  4320
ggtggctagg aatcacggag acctcttgac ttgcagggta ggctagctag aattaagtga  4380
ggtgacaagg tttccataca gttttgacct tgagacgttg ctacttacga tttgcagtat  4440
gcaagtctca tgctgcaaac aaaagaggac cgctcaggta atcgctcaat tagtggacgt  4500
tatcaggggc gggagaggcg aaagtggttt ttggtggtgt aagtaaaggt cgtccaaata  4560
tgcaggtgtt tgggtgctat cctagtggaa gctcggatca gtagataacc cgcctagaag   4620
cggtattttt ctttttttttt cttccttctt tttcgtcatt atttcaaacg cttttgcgtc  4680
```

```
aagtaatgaa tatctggcgg ttccgcggta atgcgacaat ttgtgatatg cactcttaaa   4740
accccgccac gatgatcgca cgtgccggca tttatagacg acttttctgg ttgtcccgct   4800
tcacggcaca tgcatgcatc aatgaccgaa ttcaggttgc tactaaccat tgtgttgtgt   4860
tattgctgtg catgaggtgc tcaagtgccc gcggcatctg actagtggta actctagacg   4920
gcttcgatgc agagagttcc tcaaaatttt tcttttcaat tgtttgcctg gtttccgcgg   4980
cgtatatcag ttttttggcga tatggtaacg cgatactcta cggcaccttc acggtagatg   5040
tcttttttaa aagtgactgt taattccagg attgaaagga agtgtcgaat agtatagtat   5100
gctttctagg ccggccgttt aaatgggccc gcggcccgtt taaacggccg gcccttccct   5160
tttacagtgc ttcggaaaag cacagcgttg tccaagggaa caattttttct tcaagttaat   5220
gcataagaaa tatcttttttt tatgtttagc taagtaaaag cagcttggag taaaaaaaaa   5280
aatgagtaaa tttctcgatg gattagtttc tcacaggtaa cataacaaaa accaagaaaa   5340
gcccgcttct gaaaactaca gttgacttgt atgctaaagg ccagactaa tgggaggaga   5400
aaagaaacg aatgtatatg ctcatttaca ctctatatca ccatatggag gataagttgg   5460
gctgagcttc tgatccaatt tattctatcc attagttgct gatatgtccc accagccaac   5520
acttgatagt atctactcgc cattcacttc cagcagcgcc agtagggttg ttgagcttag   5580
taaaaatgtg cgcaccacaa gcctacatga ctccacgtca catgaaacca caccgtgggg   5640
ccttgttgcg ctaggaatag gatatgcgac gaagacgctt ctgcttagta accacaccac   5700
attttcaggg ggtcgatctg cttgcttcct ttactgtcac gagcggccca taatcgcgct   5760
tttttttttaa aaggcgcgag acagcaaaca ggaagctcgg gtttcaacct tcggagtggt   5820
cgcagatctg gagactggat ctttacaata cagtaaggca agccaccatc tgcttcttag   5880
gtgcatgcga cggtatccac gtgcagaaca acatagtctg aagaaggggg ggaggagcat   5940
gttcattctc tgtagcagta agagcttggt gataatgacc aaaactggag tctcgaaatc   6000
atataaatag acaatatatt ttcacacaat gagatttgta gtacagttct attctctctc   6060
ttgcataaat aagaaattca tcaagaactt ggtttgatat ttcaccaaca cacacaaaaa   6120
acagtacttc actaaattta cacacaaaac aaaatggaat tgaacaacgt tatcttggaa   6180
aaggaaggta aggttgccgt tgtcaccatc aacagaccaa aggctttgaa tgctttgaac   6240
tctgacactt tgaaggaaat ggactacgtc attggtgaaa ttgaaaacga ttctgaagtt   6300
ttggctgtca tcttgaccgg tgccggtgaa aagtctttcg ttgctggtgc tgatatctct   6360
gaaatgaagg aaatgaacac cattgaaggt agaaagttcg gtatcttagg taacaaggtt   6420
ttcagaagat tggaattgtt ggaaaagcca gtcattgctg ctgtcaacgg tttcgctttg   6480
ggtggtggtt gtgaaattgc catgtcctgt gacatcagaa ttgcttcttc taacgctcgt   6540
ttcggtcaac cagaagtcgg tctaggtatc actccaggtt tcggtggtac tcaaagatta   6600
tccagattgt tggtatggg tatggccaag caattgatct tcaccgctca aacatcaag   6660
gctgacgaag ctttgagaat tggtttagtc aacaaggttg ttgaaccatc tgaattgatg   6720
aacactgcca aggaaattgc taacaagatc gtctccaacg ctccagttgc tgtcaaattg   6780
tccaagcaag ccatcaacag aggtatgcaa tgtgatatcg acaccgcttt ggcctttgaa   6840
tctgaagctt tcggtgaatg tttctccact gaagaccaaa aggatgctat gaccgctttc   6900
atcgaaaaga gaaagattga aggtttcaag aacaggtgat gagcccgggc gcgaattcct   6960
tatgatttat gatttttatt attaaataag ttataaaaaa aataagtgta tacaaatttt   7020
```

```
aaagtgactc ttaggtttta aaacgaaaat tcttattctt gagtaactct ttcctgtagg    7080
tcaggttgct ttctcaggta tagcatgagg tcgctcttat tgaccacacc tctaccggca    7140
tgccgagcaa atgcctgcaa atcgctcccc atttcaccca attgtagata tgctaactcc    7200
agcaatgagt tgatgaatct cggtgtgtat tttatgtcct cagaggacaa cacctgttgt    7260
aatcgttctt ccacacggat ccacagccta gccttcagtt gggctctatc ttcatcgtca    7320
ttcattgcat ctactagccc cttacctgag cttcaagacg ttatatcgct tttatgtatc    7380
atgatcttat cttgagatat gaatacataa atatatttac tcaagtgtat acgtgcatgc    7440
tttttttacg gtttaaacat ttaaatgggc cgctctagag gatccccggg taccgagctc    7500
gggcccagcg ctactagttc cggtaatttg aaaacaaacc cggtctcgaa gcggagatcc    7560
ggcgataatt accgcagaaa taaacccata cacgagacgt agaaccagcc gcacatggcc    7620
ggagaaactc ctgcgagaat tcgtaaact cgcgcgcatt gcatctgtat ttcctaatgc     7680
ggcacttcca ggcctcgaga cctctgacat gcttttgaca ggaatagaca ttttcagaat    7740
gttatccata tgcctttcgg gtttttttcc ttcctttttcc atcatgaaaa atctctcgag   7800
accgtttatc cattgctttt ttgttgtctt tttccctcgt tcacagaaag tctgaagaag    7860
ctatagtaga actatgagct ttttttgttt ctgttttcct tttttttttt tttacctctg    7920
tggaaattgt tactctcaca ctctttagtt cgtttgtttg ttttgtttat tccaattatg    7980
accggtgacg aaacgtggtc gatggtgggt accgcttatg ctcccctcca ttagtttcga    8040
ttatataaaa aggccaaata ttgtattatt ttcaaatgtc ctatcattat cgtctaacat    8100
ctaatttctc ttaaattttt tctctttctt tcctataaca ccaatagtga aaatcttttt    8160
ttcttctata tctacaaaaa ctttttttt ctatcaacct cgttgataaa ttttttcttt    8220
aacaatcgtt aataattaat taattggaaa ataaccattt tttctctctt ttatacacac    8280
attcaaaaga aagaaaaaaa atatacccca gctagttaaa gaaaatcatt gaaaagaata    8340
agaagataag aaagattttaa ttatcaaaca atatcaatat gcctcaatcc tgggaagaac    8400
tggccgctga taagcgcgcc cgcctcgcaa aaaccatccc tgatgaatgg aaagtccaga    8460
cgctgcctgc ggaagacagc gttattgatt tcccaaagaa atcggggatc ctttcagagg    8520
ccgaactgaa gatcacagag gcctccgctg cagatcttgt gtccaagctg gcggccggag    8580
agttgacctc ggtggaagtt acgctagcat tctgtaaacg ggcagcaatc gcccagcagt    8640
taacaaactg cgcccacgag ttcttccctg acgccgctct cgcgcaggca agggaactcg    8700
atgaatacta cgcaaagcac aagagacccg ttggtccact ccatggcctc cccatctctc    8760
tcaaagacca gcttcgagtc aagggctacg aaacatcaat gggctacatc tcatggctaa    8820
acaagtacga cgaaggggac tcggttctga caaccatgct ccgcaaagcc ggtgccgtct    8880
tctacgtcaa gacctctgtc ccgcagaccc tgatggtctg cgagacagtc aacaacatca    8940
tcgggcgcac cgtcaaccca cgcaacaaga actggtcgtg cggcggcagt tctggtggtg    9000
agggtgcgat cgttgggatt cgtggtggcg tcatcggtgt aggaacggat atcggtggct    9060
cgattcgagt gccggccgcg ttcaacttcc tgtacggtct aaggccgagt catgggcggc    9120
tgccgtatgc aaagatggcg aacagcatgg agggtcagga cacggtgcac agcgttgtcg    9180
ggccgattac gcactctgtt gaggacctcc gcctcttcac caaatccgtc ctcggtcagg    9240
agccatggaa atacgactcc aaggtcatcc ccatgccctg gcgccagtcc gagtcggaca    9300
ttattgcctc caagatcaag aacggcgggc tcaatatcgg ctactacaac ttcgacggca    9360
atgtccttcc acaccctcct atcctgcgcg gcgtggaaac caccgtcgcc gcactcgcca    9420
```

-continued

```
aagccggtca caccgtgacc ccgtggacgc catacaagca cgatttcggc cacgatctca   9480
tctcccatat ctacgcggct gacggcagcg ccgacgtaat gcgcgatatc agtgcatccg   9540
gcgagccggc gattccaaat atcaaagacc tactgaaccc gaacatcaaa gctgttaaca   9600
tgaacgagct ctgggacacg catctccaga agtggaatta ccagatggag taccttgaga   9660
aatggcggga ggctgaagaa aaggccggga aggaactgga cgccatcatc gcgccgatta   9720
cgcctaccgc tgcggtacgg catgaccagt tccggtacta tgggtatgcc tctgtgatca   9780
acctgctgga tttcacgagc gtggttgttc cggttacctt tgcggataag aacatcgata   9840
agaagaatga gagtttcaag gcggttagtg agcttgatgc cctcgtgcag gaagagtatg   9900
atccggaggc gtaccatggg gcaccggttg cagtgcaggt tatcggacgg agactcagtg   9960
aagagaggac gttggcgatt gcagaggaag tggggaagtt gctgggaaat gtggtgactc  10020
cataggtcga gaatttatac ttagataagt atgtacttac aggtatattt ctatgagata  10080
ctgatgtata catgcatgat aatatttaaa cggttattag tgccgattgt cttgtgcgat  10140
aatgacgttc ctatcaaagc aatacactta ccacctatta catgggccaa gaaaatattt  10200
tcgaacttgt ttagaatatt agcacagagt atatgatgat atccgttaga ttatgcatga  10260
ttcattccta caacttttc gtagcataag gattaattac ttggatgcca ataaaaaaaa  10320
aaaacatcga gaaatttca gcatgctcag aaacaattgc agtgtatcaa agtaaaaaaa  10380
agattttcgc tacatgttcc ttttgaagaa agaaaatcat ggaacattag atttacaaaa  10440
atttaaccac cgctgattaa cgattagacc gttaagcgca caacaggtta ttagtacaga  10500
gaaagcattc tgtggtgttg ccccggactt tcttttgcga cataggtaaa tcgaatacca  10560
tcatactatc ttttccaatg actccctaaa gaaagactct tcttcgatgt tgtatacgtt  10620
ggagcatagg gcaagaattg tggcttgaga tgaattcact ggccgtcgtt ttacaacgtc  10680
gtgactggga aaaccctggc gttacccaac ttaatcgcct tgcagcacat ccccctttcg  10740
ccagctggcg taatagcgaa gaggcccgca ccgatcgccc ttcccaacag ttgcgcagcc  10800
tgaatggcga atggcgcctg atgcggtatt ttctccttac gcatctgtgc ggtatttcac  10860
accgcatatg gtgcactctc agtacaatct gctctgatgc cgcatagtta agccagcccc  10920
gacacccgcc aacacccgct gacgcgccct gacgggcttg tctgctcccg gcatccgctt  10980
acagacaagc tgtgaccgtc tccgggagct gcatgtgtca gaggttttca ccgtcatcac  11040
cgaaacgcgc gagacgaaag ggcctcgtga tacgcctatt tttataggtt aatgtcatga  11100
taataatggt tcttagacg tcaggtggca cttttcgggg aaatgtgcgc ggaaccccta  11160
tttgtttatt tttctaaata cattcaaata tgtatccgct catgagacaa taaccctgat  11220
aaatgcttca ataatattga aaaggaaga gtatgagtat caacatttc cgtgtcgccc  11280
ttattccctt ttttgcggca ttttgccttc ctgtttttgc tcacccagaa acgctggtga  11340
aagtaaaaga tgctgaagat cagttgggtg cacgagtggg ttacatcgaa ctggatctca  11400
acagcggtaa gatccttgag agttttcgcc ccgaagaacg ttttccaatg atgagcactt  11460
ttaaagttct gctatgtggc gcggtattat cccgtattga cgccgggcaa gagcaactcg  11520
gtcgccgcat acactattct cagaatgact tggttgagta ctcaccagtc acagaaaagc  11580
atcttacgga tggcatgaca gtaagagaat tatgcagtgc tgccataacc atgagtgata  11640
acactgcggc caacttactt ctgacaacga tcggaggacc gaaggagcta accgcttttt  11700
tgcacaacat gggggatcat gtaactcgcc ttgatcgttg ggaaccggag ctgaatgaag  11760
```

-continued

```
ccataccaaa cgacgagcgt gacaccacga tgcctgtagc aatggcaaca acgttgcgca    11820
aactattaac tggcgaacta cttactctag cttcccggca acaattaata gactggatgg    11880
aggcggataa agttgcagga ccacttctgc gctcggccct tccggctggc tggtttattg    11940
ctgataaatc tggagccggt gagcgtgggt ctcgcggtat cattgcagca ctggggccag    12000
atggtaagcc ctcccgtatc gtagttatct acacgacggg gagtcaggca actatggatg    12060
aacgaaatag acagatcgct gagataggtg cctcactgat taagcattgg taactgtcag    12120
accaagttta ctcatatata ctttagattg atttaaaact tcattttta tttaaaagga    12180 tctaggtgaa gatccttttt gataatctca tgaccaaaat cccttaacgt gagttttcgt    12240
tccactgagc gtcagacccc gtagaaaaga tcaaaggatc ttcttgagat cctttttttc    12300
tgcgcgtaat ctgctgcttg caaacaaaaa aaccaccgct accagcggtg gtttgtttgc    12360
cggatcaaga gctaccaact ctttttccga aggtaactgg cttcagcaga gcgcagatac    12420
caaatactgt ccttctagtg tagccgtagt taggccacca cttcaagaac tctgtagcac    12480
cgcctacata cctcgctctg ctaatcctgt taccagtggc tgctgccagt ggcgataagt    12540
cgtgtcttac cgggttggac tcaagacgat agttaccgga taaggcgcag cggtcgggct    12600 gaacggggg ttcgtgcaca cagcccagct tggagcgaac gacctacacc gaactgagat    12660
acctacagcg tgagctatga gaaagcgcca cgcttcccga agggagaaag gcggacaggt    12720
atccggtaag cggcagggtc ggaacaggag agcgcacgag ggagcttcca ggggaaacg    12780 cctggtatct ttatagtcct gtcgggtttc gccacctctg acttgagcgt cgatttttgt    12840
gatgctcgtc aggggggcgg agcctatgga aaaacgccag caacgcggcc ttttacggt    12900 tcctggcctt ttgctggcct tttgctcaca tgttcttcc tgcgttatcc cctgattctg    12960
tggataaccg tattaccgcc tttgagtgag ctgataccgc tcgccgcagc cgaacgaccg    13020
agcgcagcga gtcagtgagc gaggaagcgg aagagcgccc aatacgcaaa ccgcctctcc    13080
ccgcgcgttg gccgattcat taatgcagct ggcacgacag gtttcccgac tggaaagcgg    13140
gcagtgagcg caacgcaatt aatgtgagtt agctcactca ttaggcaccc caggctttac    13200
actttatgct tccggctcgt atgttgtgtg gaattgtgag cggataacaa tttcacacag    13260
gaaacagcta tgaccatgat tacgcc                                         13286
```

<210> SEQ ID NO 42
<211> LENGTH: 16359
<212> TYPE: DNA
<213> ORGANISM: Artificial
<220> FEATURE:
<223> OTHER INFORMATION: pBOL36

<400> SEQUENCE: 42

```
aagcttgcat gcctgcaggt cgacggcgcg ccgggcccgt ttaaacaatg gcaaactgag      60
cacaacaata ccagtccgga tcaactggca ccatctctcc cgtagtctca tctaattttt    120
cttccggatg aggttccaga tataccgcaa cacctttatt atggtttccc tgagggaata    180
atagaatgtc ccattcgaaa tcaccaattc taaacctggg cgaattgtat tcgggtttg    240 ttaactcgtt ccagtcagga atgttccacg tgaagctatc ttccagcaaa gtctccactt    300
cttcatcaaa ttgtgggaga atactcccaa tgctcttatc tatgggactt ccgggaaaca    360
cagtaccgat acttcccaat tcgtcttcag agctcattgt ttgtttgaag agactaatca    420
aagaatcgtt ttctcaaaaa aattaatatc ttaactgata gtttgatcaa aggggcaaaa    480
cgtaggggca aacaaacgga aaaatcgttt ctcaaatttt ctgatgccaa gaactctaac    540
```

```
cagtcttatc taaaaattgc cttatgatcc gtctctccgg ttacagcctg tgtaactgat    600
taatcctgcc tttctaatca ccattctaat gttttaatta agggattttg tcttcattaa    660
cggctttcgc tcataaaaat gttatgacgt tttgcccgca ggcgggaaac catccacttc    720
acgagactga tctcctctgc cggaacaccg ggcatctcca acttataagt tggagaaata    780
agagaatttc agattgagag aatgaaaaaa aaaaaaaaa aaaggcaga ggagagcata    840 gaaatggggt tcactttttg gtaaagctat agcatgccta tcacatataa atagagtgcc    900
agtagcgact tttttcacac tcgaaatact cttactactg ctctcttgtt gtttttatca    960
cttcttgttt cttcttggta aatagaatat caagctacaa aaagcataca atcaactatc   1020
aactattaac tatatcgtaa tacacaggcc ggccaaaatg aaggccaaat caaggcggga   1080
agggacaacc aggacgtaaa gggtagcctc cccataacat aaactcaata aaatatatag   1140
tcttcaactt gaaaaggaa caagctcatg caaagaggtg gtacccgcac gccgaaatgc   1200
atgcaagtaa cctattcaaa gtaatatctc atacatgttt catgagggta acaacatgcg   1260
actgggtgag catatgttcc gctgatgtga tgtgcaagat aaacaagcaa gacagaaact   1320
aacttcttct tcatgtaata aacacacccc gcgtttattt acctatcttt aaacttcaac   1380
accttatatc ataactaata tttcttgaga taagcacact gcacccatac cttccttaaa   1440
aacgtagctt ccagtttttg gtggttctgg cttccttccc gattccgccc gctaaacgca   1500
taattttgtt gcctggtggc atttgcaaaa tgcataacct atgcatttaa aagattatgt   1560
atgctcttct gacttttcgt gtgatgaggc tcgtggaaaa aatgaataat ttatgaattt   1620
gagaacaatt ttgtgttgtt acggtatttt actatggaat aatcaatcaa ttgaggattt   1680
tatgcaaata tcgtttgaat attttttccga ccctttgagt acttttcttc ataattgcat   1740
aatattgtcc gctgcccgtt tttctgttag acggtgtctt gatctacttg ctatcgttca   1800
acaccacctt attttctaac tattttttt ttagctcatt tgaatcagct tatggtgatg   1860
gcacattttt gcataaacct agctgtcctc gttgaacata ggaaaaaaaa atatataaac   1920
aaggctcttt cactctcctt ggaatcagat ttgggtttgt tccctttatt ttcatatttc   1980
ttgtcatatt cttttctcaa ttattatctt ctactcataa cctcacgcaa aataacacag   2040
tcaaatcaat caaatgcgac ttcaacttga ccagagaaca agaattggtc agacaaatgg   2100
ttagagaatt tgctgaaaac gaagttaagc caattgctgc tgaaatcgat gaaactgaaa   2160
gattcccaat ggaaaacgtc aagaagatgg gtcaatacgg tatgatgggt attccattct   2220
ctaaggaata cggtggtgct ggtggtgacg tcttgtctta catcattgct gtcgaagaat   2280
tgtccaaggt ttgtggtacc actggtgtca tcttatctgc tcacacttct ctatgtgcct   2340
ccttgatcaa cgaacacggt actgaagaac aaaagcaaaa gtacttggtt ccattggcca   2400
agggtgaaaa gattggtgcc tacggtttga ctgaaccaaa cgctggtact gactctggtg   2460
ctcaacaaac tgttgccgtt ttggaaggtg accactacgt catcaacggt tccaagatct   2520
tcatcaccaa cggtggtgtt gctgacacct tgtcatctct cgctatgacc gatcgtacca   2580
agggtaccaa gggtatctct gctttcatta ttgaaaaggg tttcaagggt ttctccatcg   2640
gtaaggtcga acaaaagttg ggtatcagag cttcctctac cactgaattg gttttcgaag   2700
acatgattgt tccagttgaa aacatgatcg gtaaggaagg taagggtttc ccaattgcca   2760
tgaagacttt agatggtggt agaattggta ttgctgctca agctttgggt attgctgaag   2820
gtgccttcaa cgaagctaga gcttacatga aggaaagaaa gcaattcggt agatctttgg   2880
```

```
acaaattcca aggtttggct tggatgatgg ctgacatgga cgttgccatc gaatctgctc    2940
gttacttggt ctacaaggct gcttacttga agcaagctgg tttgccatac accgtcgatg    3000
ctgccagagc taagttgcac gctgccaacg ttgccatgga tgtcaccacc aaggctgtcc    3060
aattattcgg tggttacggt tacaccaagg actacccagt tgaaagaatg atgagagatg    3120
ctaagatcac tgaaatctac gaaggtactt ctgaagttca aaagttggtt atctccggta    3180
agatcttcag ataggcccgg gcataaagca atcttgatga ggataatgat tttttttttga   3240 atatacataa atactaccgt ttttctgcta gattttgtga agacgtaaat aagtacatat    3300 tacttttttaa gccaagacaa gattaagcat aactttacc cttttctctt ctaagtttca    3360
atactagtta tcactgttta aaagttatgg cgagaacgtc ggcggttaaa atatattacc    3420
ctgaacgtgg tgaattgaag ttctaggatg gtttaaagat ttttccttttt tgggaaataa   3480 gtaaacaata tattgctgcc tttgcaaaac gcacataccc acaatatgtg actattggca    3540
aagaacgcat tatcctttga agaggtggat actgatacta agagagtctc tattccggct    3600
ccacttttag tccagagatt acttgtcttc ttacgtatca gaacaagaaa gcatttccaa    3660
agtaattgca tttgcccttg agcagtatat atatactaag aagtttaaac atttaaacgg    3720
ccggcctaga aagcatacta tactattcga cacttccttt caatcctgga attaacagtc    3780
acttttaaaa aagacatcta ccgtgaaggt gccgtagagt atcgcgttac catatcgcca    3840
aaaactgata tacgccgcgg aaaccaggca aacaattgaa aagaaaaatt ttgaggaact    3900
ctctgcatcg aagccgtcta gagttaccac tagtcagatg ccgcgggcac ttgagcacct    3960
catgcacagc aataacacaa cacaatggtt agtagcaacc tgaattcggt cattgatgca    4020
tgcatgtgcc gtgaagcggg acaaccagaa aagtcgtcta taaatgccgg cacgtgcgat    4080
catcgtggcg gggttttaag agtgcatatc acaaattgtc gcattaccgc ggaaccgcca    4140
gatattcatt acttgacgca aaagcgtttg aaataatgac gaaaagaag gaagaaaaaa     4200 aaagaaaaat accgcttcta ggcgggttat ctactgatcc gagcttccac taggatagca    4260
cccaaacacc tgcatatttg gacgaccttt acttacacca ccaaaaacca ctttcgcctc    4320
tcccgcccct gataacgtcc actaattgag cgattacctg agcggtcctc ttttgtttgc    4380
agcatgagac ttgcatactg caaatcgtaa gtagcaacgt ctcaaggtca aaactgtatg    4440
gaaaccttgt cacctcactt aattctagct agcctaccct gcaagtcaag aggtctccgt    4500
gattcctagc cacctcaagg tatgcctctc cccggaaact gtggccttttt ctggcacaca    4560 tgatctccac gatttcaaca tataaatagc ttttgataat ggcaatatta atcaaattta    4620
ttttacttct ttcttgtaac atctctcttg taatccctta ttccttctag ctattttttca   4680 taaaaaacca agcaactgct tatcaacaca caaacactaa atcaaaatgg tcgatttcga    4740
atactctatc ccaaccagaa tcttcttcgg taaggacaag atcaacgttt tgggtagaga    4800
attgaagaaa tacggttcca aggttttgat tgtctacggt ggtggttcca tcaagagaaa    4860
cggtatctac gacaaggctg tctccatttt tggaaagaac tctatcaaat tctacgaatt    4920
ggctggtgtt gaaccaaacc caagagttac caccgtcgaa aagggtgtca agatctgtcg    4980
tgaaaacggt gttgaagttg ttttggccat cggtggtggt tctgccattg actgtgccaa    5040
ggtcattgct gctgcctgtg aatacgatgg taacccatgg acattgtct tggatggttc    5100 taagatcaag cgtgtcttac caattgcttc catcttgact atcgctgcta ctggttctga    5160
aatggacacc tgggctgtta tcaacaacat ggacactaac gaaaagttga ttgctgctca    5220
cccagatatg gccccaaagt tctctatttt ggacccaacc tacacttaca ctgttccaac    5280
```

```
caaccaaact gctgctggta ctgctgatat catgtctcac atctttgaag tttacttctc    5340
caacaccaag accgcttact tgcaagacag aatggctgaa gctctattaa gaacctgtat    5400
caagtacggt ggtattgctt tggaaaagcc agatgactac gaagccagag ctaacttgat    5460
gtgggcttcc tctttggcta tcaacggttt attgacttac ggtaaggaca ccaactggtc    5520
cgttcatttg atggaacacg aattgtctgc ttactacgat atcactcacg gtgtcggttt    5580
ggccatcttg actccaaact ggatggaata cattttgaac aacgacactg tctacaagtt    5640
cgtcgaatac ggtgttaacg tctggggtat tgacaaggaa aagaaccact acgacattgc    5700
tcaccaagcc atccaaaaga ccagagacta tttcgtcaac gttttgggtt taccatccag    5760
attaagagat gttggtattg aagaagaaaa attggatatc atggctaagg aatctgtcaa    5820
attgactggt ggtaccattg gtaacttgag acctgttaac gcttctgaag ttttgcaaat    5880
cttcaagaaa tctgtttagg cccgggctcc tgttgaagta gcatttaatc ataattttg    5940 tcacattta atcaacttga tttttctggt ttaattttc taattttaat tttaatttt    6000 ttatcaatgg gaactgatac actaaaaaga attaggagcc aacaagaata agccgcttat    6060
ttcctactag agtttgctta aaatttcatc tcgaattgtc attctaatat tttatccaca    6120 cacacaccctt aaaattttta gattaaatgg catcaactct tagcttcaca cacacacaca    6180
caccgaagct ggttgtttta tttgatttga tataattggt ttctctggat ggtacttttt    6240
ctttcttggt tatttcctat tttaaaatat gaaacgcaca caagtcataa ttattctaat    6300
agagcacaat tcacaacacg cacatttcaa ctttaatatt tttttagaaa cactttattt    6360
agtctaattc ttaattttta atatatataa tgcacacaca cgtttaaatg ggcccgcggc    6420
ccgtttaaac ggccggccct tccctttac agtgcttcgg aaaagcacag cgttgtccaa    6480
gggaacaatt tttcttcaag ttaatgcata agaaatatct tttttatgt ttagctaagt    6540 aaaagcagct tggagtaaaa aaaaaaatga gtaaatttct cgatggatta gtttctcaca    6600
ggtaacatag caaaaaccaa gaaaagcccg cttctgaaaa ctacagttga cttgtatgct    6660
aaagggccag actaatggga ggagaaaaag aaacgaatgt atatgctcat ttacactcta    6720
tatcaccata tggaggataa gttgggctga gcttctgatc caatttattc tatccattag    6780
ttgctgatat gtcccaccag ccaacacttg atagtatcta ctcgccattc acttccagca    6840
gcgccagtag ggttgttgag cttagtaaaa atgtgcgcac cacaagccta catgactcca    6900
cgtcacatga aaccacaccg tggggccttg ttgcgctagg aataggatat gcgacgaaga    6960
cgcttctgct tagtaaccac accacatttt caggggtgtcg atctgcttgc ttcctttact    7020
gtcacgagcg gcccataatc gcgctttttt tttaaaaggc gcgagacagc aaacaggaag    7080
ctcgggtttc aaccttcgga gtggtcgcag atctggagac tggatcttta caatacgtta    7140
aggcaagcca ccatctgctt cttaggtgca tgcgacggta tccacgtgca gaacaacata    7200
gtctgaagaa ggggggagg agcatgttca ttctctgtag cagtaagagc ttggtgataa    7260
tgaccaaaac tggagtctcg aaatcatata aatagacaat atattttcac acaatgagat    7320
ttgtagtaca gttctattct ctctcttgca taaataagaa attcatcaag aacttggttt    7380
gatatttcac caacacacac aaaaaacagt acttcactaa atttacacac aaaacaaaat    7440
gaaggttacc aaccaaaagg aattgaagca aaagttgaac gaattgagag aagctcaaaa    7500
gaagttcgct acctacactc aagaacaagt tgacaagatc ttcaagcaat gtgccattgc    7560
tgctgccaag gaacgtatca acttggccaa gttggctgtc gaagaaaccg gtattggttt    7620
```

```
ggttgaagac aagatcatca agaaccactt cgctgctgaa tacatctaca acaagtacaa  7680
gaacgaaaag acctgtggta tcatcgacca cgatgactct ttgggtatca ccaaggttgc  7740
tgaaccaatc ggtattgtcg ccgccattgt cccaaccact aacccaactt ccactgccat  7800
cttcaaatct ttgatctcct tgaagaccag aaacgctatc ttcttctccc cacacccaag  7860
agccaagaag tccaccattg ctgctgccaa attaatcttg gatgctgctg ttaaggctgg  7920
tgccccaaag aacattattg gttggatcga tgaaccttcc attgaattgt ctcaagactt  7980
gatgtctgaa gctgatatca tcttggctac cggtggtcca tccatggtca aggccgctta  8040
ctcttctggt aagccagcta ttggtgttgg tgctggtaac actccagcta tcatcgatga  8100
atctgctgac attgacatgg ctgtctcctc cattatcttg tccaagactt atgacaacgg  8160
tgtcatctgt gcctctgaac aatccatctt ggttatgaac tctatctacg aaaaggtcaa  8220
ggaagaattt gttaagagag gttcctacat cttaaaccaa aatgaaattg ccaagatcaa  8280
ggaaaccatg ttcaagaacg gtgccatcaa cgctgacatt gtcggtaaat ctgcttacat  8340
cattgccaag atggctggta ttgaagttcc acaaaccact aagattttga tcggtgaagt  8400
tcaatctgtc gaaaagtctg aattattctc tcacgaaaag ttgtctccag tcttggctat  8460
gtacaaggtc aaggatttcg acgaagcttt gaagaaggct caaagattaa ttgaattagg  8520
tggttctggt cacacctctt ctctatacat tgactctcaa aacaacaagg acaaggtcaa  8580
ggaattcggt ctagctatga agacttccag aactttcatc aacatgccat cttctcaagg  8640
tgcttctggt gatttgtaca actttgccat tgctccatct ttcactttag ttgtggtac   8700
ctggggtggt aactctgttt ctcaaaacgt tgaaccaaag catttgctaa acatcaagtc  8760
cgttgctgaa agaagagaaa acatgttgtg gttcaaggtt ccacaaaaga tctacttcaa  8820
atacggttgt ttgagatttg ctttgaagga attgaaagat atgaacaaga gcgtgctttt  8880
catcgttact gacaaggatt tgttcaaatt gggttacgtt aacaagatca ctaaggtttt  8940
ggatgaaatt gatatcaagt actccatctt cactgatatc aaatctgacc caaccattga  9000
ctccgtcaag aagggtgcta aggaaatgtt gaacttcgaa ccagatacca ttatctccat  9060
tggtggtggt tctccaatgg atgctgccaa ggttatgcat ttgttgtacg aatacccaga  9120
agctgaaatc gaaaacttgg ccatcaactt catggacatc agaaagagaa tctgtaactt  9180
cccaaagttg ggtaccaagg ccatttctgt tgccattcca accaccgctg gtaccggttc  9240
tgaagctact ccatttgctg tcatcaccaa cgacgaaacc ggtatgaagt acccattgac  9300
ctcttacgaa ttgactccaa acatggccat cattgacact gaattgatgt tgaacatgcc  9360
aagaaagttg actgctgcta ccggtattga cgctttagtc cacgctatcg aagcttacgt  9420
ctccgttatg gccactgact acactgacga attggctttg agagctatca agatgatctt  9480
caagtacttg ccaagagctt acaagaacgg tactaacgat atcgaagctc gtgaaaagat  9540
ggctcacgct tccaacattg ctggtatggc tttcgctaac gctttcttgg gtgtttgtca  9600
ctccatggcc cacaagttgg gtgctatgca ccacgttcct cacggtattg cttgtgctgt  9660
tttgattgaa gaagtcatca agtacaacgc tactgactgt ccaaccaagc aaactgcttt  9720
cccacaatac aagtctccaa acgccaagag aaagtacgct gaaattgctg aatacttgaa  9780
cttgaaaggt acttctgaca ctgaaaaggt cactgcttta atcgaagcta tctccaagtt  9840
gaagattgac ttatctattc ctcaaaacat ctctgctgct ggtattaaca agaaggactt  9900
ctacaacact ttagacaaga tgtccgaatt ggctttcgat gaccaatgta ccaccgctaa  9960
cccaagatac ccattgatct ctgaattgaa ggatatctac atcaagtcct tttaagcccg 10020
```

```
ggcgcggatc tcttatgtct ttacgattta tagttttcat tatcaagtat gcctatatta    10080
gtatatagca tctttagatg acagtgttcg aagtttcacg aataaaagat aatattctac    10140
tttttgctcc caccgcgttt gctagcacga gtgaacacca tccctcgcct gtgagttgta    10200
cccattcctc taaactgtag acatggtagc ttcagcagtg ttcgttatgt acggcatcct    10260
ccaacaaaca gtcggttata gtttgtcctg ctcctctgaa tcgtctccct cgatatttct    10320 catttttcctt cgcatgccag cattgaaatg atcgaagttc aatgatgaaa cggtaattct    10380
tctgtcattt actcatctca tctcatcaag ttatataatt ctatacggat gtaattttc     10440 acttttcgtc ttgacgtcca ccctataatt tcaattattg aaccctcaca aatgatgcac    10500
tgcaatgtac acaccctcat atagtttaaa catttaaatg ggccgctcta gaggatcccc    10560
gggtaccgag ctcgggccca cgcgctactag ttccggtaat ttgaaaacaa acccggtctc   10620
gaagcggaga tccggcgata attaccgcag aaataaaccc atacacgaga cgtagaacca    10680
gccgcacatg gccggagaaa ctcctgcgag aatttcgtaa actcgcgcgc attgcatctg    10740
tatttcctaa tgcggcactt ccaggcctcg agacctctga catgcttttg acaggaatag    10800
acattttcag aatgttatcc atatgccttt cgggtttttt tccttccttt tccatcatga    10860
aaaatctctc gagaccgttt atccattgct ttttttgttgt ctttttccct cgttcacaga   10920
aagtctgaag aagctatagt agaactatga gcttttttg tttctgtttt ccttttttt     10980 tttttttacct ctgtggaaat tgttactctc acactcttta gttcgtttgt ttgttttgtt  11040
tattccaatt atgaccggtg acgaaacgtg gtcgatggtg ggtaccgctt atgctcccct    11100
ccattagttt cgattatata aaaaggccaa atattgtatt attttcaaat gtcctatcat    11160
tatcgtctaa catctaattt ctcttaaatt ttttctcttt ctttcctata acaccaatag    11220
tgaaaatctt tttttcttct atatctacaa aaactttttt tttctatcaa cctcgttgat   11280 aaatttttc tttaacaatc gttaataatt aattaattgg aaaataacca ttttttctct    11340
cttttataca cacattcaaa agaaagaaaa aaaatatacc ccagctagtt aaagaaaatc    11400
attgaaaaga ataagaagat aagaaagatt taattatcaa acaatatcaa tatgcctcaa    11460
tcctgggaag aactggccgc tgataagcgc gcccgcctcg caaaaaccat ccctgatgaa    11520
tggaaagtcc agacgctgcc tgcggaagac agcgttattg atttcccaaa gaaatcgggg    11580
atcctttcag aggccgaact gaagatcaca gaggcctccg ctgcagatct tgtgtccaag    11640
ctggcggccg gagagttgac ctcggtggaa gttacgctag cattctgtaa acgggcagca    11700
atcgcccagc agttaacaaa ctgcgcccac gagttcttcc ctgacgccgc tctcgcgcag    11760
gcaagggaac tcgatgaata ctacgcaaag cacaagagac ccgttggtcc actccatggc    11820
ctccccatct ctctcaaaga ccagcttcga gtcaagggct acgaaacatc aatgggctac    11880
atctcatggc taaacaagta cgacgaaggg gactcggttc tgacaaccat gctccgcaaa    11940
gccggtgccg tcttctacgt caagacctct gtcccgcaga ccctgatggt ctgcgagaca    12000
gtcaacaaca tcatcgggcg caccgtcaac ccacgcaaca gaactggtc gtgcggcggc     12060 agttctggtg gtgagggtgc gatcgttggg attcgtggtg gcgtcatcgg tgtaggaacg    12120
gatatcggtg gctcgattcg agtgccggcc gcgttcaact tcctgtacgg tctaaggccg    12180
agtcatgggc ggctgccgta tgcaaagatg gcgaacagca tggagggtca ggagacggtg    12240
cacagcgttg tcgggccgat tacgcactct gttgaggacc tccgcctctt caccaaatcc    12300
gtcctcggtc aggagccatg gaaatacgac tccaaggtca tccccatgcc ctggcgccag    12360
```

```
tccgagtcgg acattattgc ctccaagatc aagaacggcg ggctcaatat cggctactac   12420
aacttcgacg gcaatgtcct tccacaccct cctatcctgc gcggcgtgga aaccaccgtc   12480
gccgcactcg ccaaagccgg tcacaccgtg accccgtgga cgccatacaa gcacgatttc   12540
ggccacgatc tcatctccca tatctacgcg gctgacggca gcgccgacgt aatgcgcgat   12600
atcagtgcat ccggcgagcc ggcgattcca aatatcaaag acctactgaa cccgaacatc   12660
aaagctgtta acatgaacga gctctgggac acgcatctcc agaagtggaa ttaccagatg   12720
gagtaccttg agaaatggcg ggaggctgaa gaaaaggccg ggaaggaact ggacgccatc   12780
atcgcgccga ttacgcctac cgctgcggta cggcatgacc agttccggta ctatgggtat   12840
gcctctgtga tcaacctgct ggatttcacg agcgtggttg ttccggttac ctttgcggat   12900
aagaacatcg ataagaagaa tgagagtttc aaggcggtta gtgagcttga tgccctcgtg   12960
caggaagagt atgatccgga ggcgtaccat ggggcaccgg ttgcagtgca ggttatcgga   13020
cggagactca gtgaagagag gacgttggcg attgcagagg aagtggggaa gttgctggga   13080
aatgtggtga ctccataggt cgagaattta tacttagata agtatgtact acaggtata   13140 tttctatgag atactgatgt atacatgcat gataatattt aaacggttat tagtgccgat   13200
tgtcttgtgc gataatgacg ttcctatcaa agcaatacac ttaccaccta ttacatgggc   13260
caagaaaata ttttcgaact tgtttagaat attagcacag agtatatgat gatatccgtt   13320
agattatgca tgattcattc ctacaacttt ttcgtagcat aaggattaat tacttggatg   13380
ccaataaaaa aaaaaaacat cgagaaaatt tcagcatgct cagaaacaat tgcagtgtat   13440
caaagtaaaa aaaagatttt cgctacatgt tccttttgaa gaaagaaaat catggaacat   13500
tagatttaca aaaatttaac caccgctgat taacgattag accgttaagc gcacaacagg   13560
ttattagtac agaaaagca ttctgtggtg ttgccccgga cttcttttg cgacataggt   13620 aaatcgaata ccatcatact atcttttcca atgactccct aaagaaagac tcttcttcga   13680
tgttgtatac gttggagcat agggcaagaa ttgtggcttg agatgaattc actgccgtc   13740 gttttacaac gtcgtgactg ggaaaaccct ggcgttaccc aacttaatcg ccttgcagca   13800 catcccctt tcgccagctg gcgtaatagc gaagaggccc gcaccgatcg cccttcccaa   13860
cagttgcgca gcctgaatgg cgaatggcgc ctgatgcggt attttctcct tacgcatctg   13920
tgcggtattt cacaccgcat atggtgcact ctcagtacaa tctgctctga tgccgcatag   13980
ttaagccagc cccgacaccc gccaacaccc gctgacgcgc cctgacgggc ttgtctgctc   14040
ccggcatccg cttacagaca agctgtgacc gtctccggga gctgcatgtg tcagaggttt   14100
tcaccgtcat caccgaaacg cgcgagacga aagggcctcg tgatacgcct atttttatag   14160
gttaatgtca tgataataat ggtttcttag acgtcaggtg gcacttttcg gggaaatgtg   14220
cgcggaaccc ctatttgttt attttttctaa atacattcaa atatgtatcc gctcatgaga   14280 caataacccct gataaatgct tcaataatat tgaaaaagga agagtatgag tattcaacat   14340
ttccgtgtcg cccttattcc cttttttgcg gcattttgcc ttcctgtttt tgctcaccca   14400
gaaacgctgg tgaaagtaaa agatgctgaa gatcagttgg gtgcacgagt gggttacatc   14460
gaactggatc tcaacagcgg taagatcctt gagagttttc gccccgaaga acgttttcca   14520
atgatgagca cttttaaagt tctgctatgt ggcgcggtat tatcccgtat tgacgccggg   14580
caagagcaac tcggtcgccg catacactat tctcagaatg acttggttga gtactcacca   14640
gtcacagaaa agcatcttac ggatggcatg acagtaagag aattatgcag tgctgccata   14700
accatgagtg ataacactgc ggccaactta cttctgacaa cgatcggagg accgaaggag   14760
```

```
ctaaccgctt ttttgcacaa catgggggat catgtaactc gccttgatcg ttgggaaccg    14820
gagctgaatg aagccatacc aaacgacgag cgtgacacca cgatgcctgt agcaatggca    14880
acaacgttgc gcaaactatt aactggcgaa ctacttactc tagcttcccg gcaacaatta    14940
atagactgga tggaggcgga taaagttgca ggaccacttc tgcgctcggc ccttccggct    15000
ggctggttta ttgctgataa atctggagcc ggtgagcgtg gtctcgcgg tatcattgca     15060 gcactggggc cagatggtaa gccctcccgt atcgtagtta tctacacgac ggggagtcag    15120
gcaactatgg atgaacgaaa tagacagatc gctgagatag gtgcctcact gattaagcat    15180
tggtaactgt cagaccaagt ttactcatat atactttaga ttgatttaaa acttcatttt    15240
taatttaaaa ggatctaggt gaagatcctt tttgataatc tcatgaccaa atcccttaa     15300 cgtgagtttt cgttccactg agcgtcagac cccgtagaaa agatcaaagg atcttcttga    15360
gatccttttt ttctgcgcgt aatctgctgc ttgcaaacaa aaaaaccacc gctaccagcg    15420
gtggtttgtt tgccggatca agagctacca actctttttc cgaaggtaac tggcttcagc    15480
agagcgcaga taccaaatac tgtccttcta gtgtagccgt agttaggcca ccacttcaag    15540
aactctgtag caccgcctac atacctcgct ctgctaatcc tgttaccagt ggctgctgcc    15600
agtggcgata agtcgtgtct taccgggttg gactcaagac gatagttacc ggataaggcg    15660
cagcggtcgg gctgaacggg gggttcgtgc acacagccca gcttggagcg aacgacctac    15720
accgaactga gatacctaca gcgtgagcta tgagaaagcg ccacgcttcc gaagggaga    15780 aaggcggaca ggtatccggt aagcggcagg gtcggaacag gagagcgcac gagggagctt    15840 ccaggggaa acgcctggta tctttatagt cctgtcgggt ttcgccacct ctgacttgag     15900
cgtcgatttt tgtgatgctc gtcagggggg cggagcctat ggaaaaacgc cagcaacgcg    15960
gcctttttac ggttcctggc cttttgctgg ccttttgctc acatgttctt tcctgcgtta    16020
tcccctgatt ctgtggataa ccgtattacc gcctttgagt gagctgatac cgctcgccgc    16080
agccgaacga ccgagcgcag cgagtcagtg agcgaggaag cggaagagcg cccaatacgc    16140
aaaccgcctc tccccgcgcg ttggccgatt cattaatgca gctggcacga caggtttccc    16200
gactggaaag cgggcagtga gcgcaacgca attaatgtga gttagctcac tcattaggca    16260
ccccaggctt tacactttat gcttccggct cgtatgttgt gtggaattgt gagcggataa    16320
caatttcaca caggaaacag ctatgaccat gattacgcc                           16359
```

<210> SEQ ID NO 43
<211> LENGTH: 8684
<212> TYPE: DNA
<213> ORGANISM: Artificial
<220> FEATURE:
<223> OTHER INFORMATION: pBOL113

<400> SEQUENCE: 43

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataccac agcttttcaa ttcaattcat catttttttt ttattctttt ttttgatttc     240
ggtttctttg aaattttttt gattcggtaa tctccgaaca gaaggaagaa cgaaggaagg     300
agcacagact tagattggta tatatacgca tatgtagtgt tgaagaaaca tgaaattgcc     360
cagtattctt aacccaactg cacagaacaa aaacctgcag gaaacgaaga taatcatgt      420
```

```
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa ttttttactc ttcgaagaca gaaaatttgc tgacattggt aatacagtca    720
aattgcagta ctctgcgggt gtatacgaaa tagcagaatg gcagacatt acgaatgcac     780 acggtgtggt gggcccaggt attgttagcg gtttgaagca ggcggcagaa gaagtaacaa    840
aggaacctag aggcctttg atgttagcag aattgtcatg caagggctcc ctatctactg     900
gagaatatac taagggtact gttgacattg cgaagagcga caaagatttt gttatcggct    960
ttattgctca aagagacatg ggtggaagag atgaaggtta cgattggttg attatgacac    1020
ccggtgtggg tttagatgac aagggagacg cattgggtca acagtataga accgtggatg    1080
atgtggtctc tacaggatct gacattatta ttgttggaag aggactattt gcaaagggaa    1140
gggatgctaa ggtagagggt gaacgttaca gaaaagcagg ctgggaagca tatttgagaa    1200
gatgcggcca gcaaaactaa aaaactgtat tataagtaaa tgcatgtata ctaaactcac    1260
aaattagagc ttcaatttaa ttatatcagt tattaccta tgcggtgtga aataccgcac      1320
agatgcgtaa ggagaaaata ccgcatcagg aaattgtaaa cgttaatatt ttgttaaaat    1380
tcgcgttaaa ttttgttaa atcagctcat tttttaacca ataggccgaa atcggcaaaa     1440
tcccttataa atcaaaagaa tagaccgaga tagggttgag tgttgttcca gtttggaaca    1500
agagtccact attaaagaac gtggactcca acgtcaaagg gcgaaaaacc gtctatcagg    1560
gcgatggccc actacgtgaa ccatcaccct aatcaagttt ttgggtcg aggtgccgta      1620 aagcactaaa tcggaaccct aaagggagcc cccgatttag agcttgacgg ggaaagccgg    1680
cgaacgtggc gagaaaggaa gggaagaaag cgaaaggagc gggcgctagg gcgctggcaa    1740
gtgtagcggt cacgctgcgc gtaaccacca cacccgccgc gcttaatgcg ccgctacagg    1800
gcgcgtcgcg ccattcgcca ttcaggctgc gcaactgttg ggaagggcga tcggtgcggg    1860
cctcttcgct attacgccag ctggcgaaag gggatgtgc tgcaaggcga ttaagttggg     1920
taacgccagg gttttcccag tcacgacgtt gtaaaacgac ggccagtgag cgcgcgtaat    1980
acgactcact atagggcgaa ttgggtaccg ggccccccct cgaggtcgac ggtatcgata    2040
agcttgatat cgaattcctg cagcccgggg gatccactag ttctagagcg gcccattaa     2100 acggccggcc ctagatcaga gggtggtaaa tgaagtgtaa tagtattcat ttttcttata    2160
aatcatccct tccgtgattt atacaaaaga agaggagaat atgctgaata cttggtatat    2220
tactctacat tatactctta tcttgacggg tattctgagc atcttactca gtttcaagat    2280 ctttaatgt ccaaaaacat ttgagccgat ctaaatactt ctgtgttttc attaatttat     2340
aaattgtact cttttaagac atggaaagta ccaacatcgg ttgaaacagt ttttcattta    2400
cttatggttt attggttttt ccagtgaatg attatttgtc gttaccctt cgtaaaagtt     2460 caaacacgtt tttaagtatt gtttagttgc tctttcgaca tatatgatta tccctgcgcg    2520
gctaaagtta aggatgcaaa aaacataaga caactgaagt taatttacgt caattaagtt    2580
ttccagggta atgatgtttt gggcttccac taattcaata agtatgtcat gaaatacgtt    2640
gtgaagagca tccagaaata tgaaaagaa acaacgaaac tgggtcggcc tgttgtttct    2700
tttctttacc acgtgatctg cggcatttac aggaagtcgc gcgttttgcg cagttgttgc    2760
aacgcagcta cggctaacaa agcctagtgg aactcgactg atgtgttagg gcctaaaact   2820
```

```
ggtggtgaca gctgaagtga actattcaat ccaatcatgt catggctgtc acaaagacct    2880
tgcggaccgc acgtacgaac acatacgtat gctaatatgt gttttgatag tacccagtga    2940
tcgcagacct gcaattttt  tgtaggtttg gaagaatata taaaggttgc actcattcaa    3000
gatagttttt ttcttgtgtg tctattcatt ttattattgt ttgtttaaat gttaaaaaaa    3060
ccaagaactt agtttcaaat taaattcatc acacaaacaa acaaaacaaa atgaacattg    3120
ttgtttgttt gaagcaagtt ccagacactg ctgaagtcag aattgaccca gtcaagggta    3180
ctttaatcag agaaggtgtt ccatctatca tcaacccaga cgacaagaac gctttggaag    3240
aagctttggt tttgaaggac aactacggtg ctcacgttac cgtcatttcc atgggtccac    3300
ctcaagccaa gaacgctttg gttgaagctt tggccatggg tgctgatgaa gctgtcttat    3360
tgactgacag agcttttcggt ggtgctgata ctttagctac ctctcacacc attgctgctg    3420
gtatcaagaa attgaaatac gatatcgtct ttgccggtcg tcaagccatc gatggtgata    3480
ccgctcaagt cggtccagaa attgctgaac atttgggtat tccacaagtc acctacgttg    3540
aaaaggttga agttgacggt gacactttga agatcagaaa ggcttgggaa gacggttacg    3600
aagttgttga agtcaagact ccagttctat tgactgccat caaggaattg aacgttccaa    3660
gatacatgtc cgttgaaaag atcttcggtg ctttcgacaa ggaagtcaag atgtggactg    3720
ctgatgatat cgatgtcgac aaggccaact gggtttgaa  aggttctcca accaaggtca    3780
agaaatcttc taccaaggaa gtcaagggtc aaggtgaagt cattgacaaa ccagtcaagg    3840
aagctgccgc ttacgttgtt tccaagttga aggaagaaca ctacatctaa agcccgggcg    3900
gagattgata agacttttct agttgcatat ctttatatt  taaatcttat ctattagtta    3960 atttttgta  atttatcctt atatatagtc tggttattct aaaatatcat ttcagtatct    4020
aaaaattccc ctcttttttc agttatatct taacaggcga cagtccaaat gttgatttat    4080
cccagtccga ttcatcaggg ttgtgaagca tttttgtcaat ggtcgaaatc acatcagtaa    4140
tagtgcctct tacttgcctc atagaatttc tttctcttaa cgtcaccgtt tggtcttta    4200 tagtttcgaa atctatggtg ataccaaatg gtgttcccaa ttcatcgtta cgggcgtatt    4260
ttttaccaat tgaagtattg gaatcgtcaa tttttaaagta tatctctctt ttacgtaaag    4320
cctgcgagat cctcttaagt atagcgggga agccatcgtt attcgatatt gtcgtaacaa    4380
atactttgat cggcgctatg tttaaatgtt taaacatgga cagatatgcg atgaaaacgc    4440
taagtgatac tccaaatggt gaaaggtacg atgcttggaa acaatacttg gaaatcaccg    4500
gaaacaccat atgcggcgaa aagccaatta gtgtgatact aagtgcttta tcgaaaatcc    4560
gtgatgccgg tccttcaggc atcaaatttc agtggcctaa ttattcacag agttctcatg    4620
tgacaagtat tgatgatagt agtgtcagtt atgcttcagg ttatgttact ataggataat    4680
gatcacggct aaaacggtcg aatgtaagca tatatctttc gattgtataa ttgttcccaa    4740
atactacagc atctcaagga aaaaaaaaca aaaacttcca aaaaaatcga atccctgagg    4800
aatctttaat acatttttcaa tctatttaag ttttataaac gtgtatatga gatgtcatga    4860
gcatgaatta ttaataataa aaactaaatc attaaagtaa cttaaggagt taaagcccgg    4920
gctttaattg ttagcagcct tgacttgagc aatcaattct ggaacaacct tgttgacatc    4980
accgacaatg gccaaatcag caaccttcat gattggagct tcgacatctt tgttgatggc    5040
aatgatgtag tcgagtcctt gcataccagc caagtgttgg atggcaccag agataccaca    5100
agcaatgtac aaagttggtc tgacggtctt accggtttga ccgacttgca agtccttgtc    5160
```

```
aacccattcc tttttcaatgg cagctctgga agcagcaatg gtaccaccca acaaagaagc    5220
taattcttcc aattttttcga agttttcctt ggaaccaaca ccacgaccac cagcaaccaa    5280
aaccttggct tcaccgatat cagcaatgtc cttggccaat ttgacaacct tggaaacctt    5340
ggttctgata tcagaagcag tcaatttgat ggcaacctttt tcgatcttgt catcagaaac    5400
gttagcatcg ttaactggca atttttcaaa gacacctggt ctgacggtgg ccatttgagg    5460
tctgtggtca gaacagacaa tggtagcaat caagttacca ccgaaagctg gtctggtagc    5520
caacaagtca cggttttcga catcgatatc caaagaggta cagtcagcag tcaaaccagt    5580
agacaatctg gcagcaattc ttggacccaa gtctctaccg atgaaagtag caccgatgaa    5640
taagatttct ggctttcttt cgttgaccaa gtcacagata accttggcgt aaccgtcagt    5700
ggagaaatga gctaataatt cgttgtcagc agccaaaacc ttgtcagcac cgtgggacaa    5760
caagtccttg gacatctttt cagtgttgtg acccaataag acagcagtca attcaacacc    5820 caattttttca gccatttcct taccctttacc tagcaattcc aaagaaacct tttgtaattc    5880
accatctctt tgttcagcga aacccagac acccttgtag tcagccttgt tcatgtttag    5940
ttaattatag ttcgttgacc gtatattcta aaaacaagta ctccttaaaa aaaaccttg    6000 aagggaataa acaagtagaa tagatagaga gaaaaataga aatgcaaga gaatttatat    6060 attagaaaga gagaaagaaa aatgaaaaaa aaaaatagg aaaagccaga aatagcacta    6120
gaaggagcga caccagaaaa gaaggtgatg gaaccaattt agctatatat agttaactac    6180
cggctcgatc atctctgcct ccagcatagt cgaagaagaa tttttttttt cttgaggctt    6240
ctgtcagcaa ctcgtatttt ttctttcttt tttggtgagc ctaaaaagtt cccacgttct    6300
cttgtacgac gccgtcacaa acaaccttat gggtaatttg tcgcggtctg ggtgtataaa    6360
tgtgtgggtg caggccggcc gtttaaacgg gccgccaccg cggtggagct ccagcttttg    6420 ttcccctttag tgagggttaa ttgcgcgctt ggcgtaatca tggtcatagc tgtttcctgt    6480
gtgaaattgt tatccgctca caattccaca caacatagga gccggaagca taaagtgtaa    6540
agcctggggt gcctaatgag tgaggtaact cacattaatt gcgttgcgct cactgcccgc    6600
tttccagtcg ggaaacctgt cgtgccagct gcattaatga atcggccaac gcgcggggag    6660
aggcggtttg cgtattgggc gctcttccgc ttcctcgctc actgactcgc tgcgctcggt    6720
cgttcggctg cggcgagcgg tatcagctca ctcaaaggcg gtaatacggt tatccacaga    6780
atcaggggat aacgcaggaa agaacatgtg agcaaaaggc cagcaaaagg ccaggaaccg    6840
taaaaaggcc gcgttgctgg cgtttttcca taggctccgc cccccctgacg agcatcacaa    6900 aaatcgacgc tcaagtcaga ggtggcgaaa cccgacagga ctataaagat accaggcgtt    6960
tccccctgga agctccctcg tgcgctctcc tgttccgacc ctgccgctta ccggatacct    7020
gtccgccttt ctcccttcgg gaagcgtggc gctttctcat agctcacgct gtaggtatct    7080
cagttcggtg taggtcgttc gctccaagct gggctgtgtg cacgaacccc ccgttcagcc    7140
cgaccgctgc gccttatccg gtaactatcg tcttgagtcc aacccggtaa gacacgactt    7200
atcgccactg gcagcagcca ctggtaacag gattagcaga gcgaggtatg taggcggtgc    7260
tacagagttc ttgaagtggt ggcctaacta cggctacact agaaggacag tatttggtat    7320
ctgcgctctg ctgaagccag ttaccttcgg aaaaagagtt ggtagctctt gatccggcaa    7380
acaaaccacc gctggtagcg gtggtttttt tgtttgcaag cagcagatta cgcgcagaaa    7440
aaaaggatct caagaagatc ctttgatctt ttctacgggg tctgacgctc agtggaacga    7500
aaactcacgt taagggattt tggtcatgag attatcaaaa aggatcttca cctagatcct    7560
```

```
tttaaattaa aaatgaagtt ttaaatcaat ctaaagtata tatgagtaaa cttggtctga   7620
cagttaccaa tgcttaatca gtgaggcacc tatctcagcg atctgtctat ttcgttcatc   7680
catagttgcc tgactcccg tcgtgtagat aactacgata cgggagggct taccatctgg    7740
ccccagtgct gcaatgatac cgcgagaccc acgctcaccg gctccagatt tatcagcaat   7800
aaaccagcca gccggaaggg ccgagcgcag aagtggtcct gcaactttat ccgcctccat   7860
ccagtctatt aattgttgcc gggaagctag agtaagtagt tcgccagtta atagtttgcg   7920
caacgttgtt gccattgcta caggcatcgt ggtgtcacgc tcgtcgtttg gtatggcttc   7980
attcagctcc ggttcccaac gatcaaggcg agttacatga tcccccatgt tgtgcaaaaa   8040
agcggttagc tccttcggtc ctccgatcgt tgtcagaagt aagttggccg cagtgttatc   8100
actcatggtt atggcagcac tgcataattc tcttactgtc atgccatccg taagatgctt   8160
ttctgtgact ggtgagtact caaccaagtc attctgagaa tagtgtatgc ggcgaccgag   8220
ttgctcttgc ccggcgtcaa tacgggataa taccgcgcca catagcagaa ctttaaaagt   8280
gctcatcatt ggaaaacgtt cttcggggcg aaaactctca aggatcttac cgctgttgag   8340
atccagttcg atgtaaccca ctcgtgcacc caactgatct tcagcatctt ttactttcac   8400
cagcgtttct gggtgagcaa aacaggaag gcaaaatgcc gcaaaaaagg gaataagggc    8460
gacacggaaa tgttgaatac tcatactctt ccttttcaa tattattgaa gcatttatca    8520
gggttattgt ctcatgagcg gatacatatt tgaatgtatt tagaaaaata aacaaatagg   8580
ggttccgcgc acatttcccc gaaaagtgcc acctgacgtc taagaaacca ttattatcat   8640
gacattaacc tataaaaata ggcgtatcac gaggcccttt cgtc                   8684
```

<210> SEQ ID NO 44
<211> LENGTH: 12314
<212> TYPE: DNA
<213> ORGANISM: Artificial
<220> FEATURE:
<223> OTHER INFORMATION: pBOL115

<400> SEQUENCE: 44

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accataccac agcttttcaa ttcaattcat catttttttt ttattctttt ttttgatttc   240
ggtttctttg aaattttttt gattcggtaa tctccgaaca gaaggaagaa cgaaggaagg   300
agcacagact tagattggta tatatacgca tatgtagtgt tgaagaaaca tgaaattgcc    360
cagtattctt aacccaactg cacagaacaa aaacctgcag gaaacgaaga taatcatgt     420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaacacatg     600
tggatatctt gactgatttt tccatggagg gcacagttaa gccgctaaag gcattatccg    660
ccaagtacaa ttttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
```

```
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattacccta tgcggtgtga aataccgcac   1320
agatgcgtaa ggagaaaata ccgcatcagg aaattgtaaa cgttaatatt ttgttaaaat   1380
tcgcgttaaa tttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact atagggcgaa ttgggtaccg gccccccct cgaggtcgac ggtatcgata   2040
agcttgatat cgaattcctg cagcccgggg gatccactag ttctagagcg cccatttaa   2100 acggccggcc ctagatcaga gggtggtaaa tgaagtgtaa tagtattcat ttttcttata   2160
aatcatccct tccgtgattt atacaaaaga agaggagaat atgctgaata cttggtatat   2220
tactctacat tatactctta tcttgacggg tattctgagc atcttactca gtttcaagat   2280
cttttaatgt ccaaaaacat ttgagccgat ctaaatactt ctgtgttttc attaatttat   2340
aaattgtact cttttaagac atggaaagta ccaacatcgg ttgaaacagt ttttcattta   2400
cttatggttt attggttttt ccagtgaatg attatttgtc gttaccctt cgtaaaagtt   2460 caaacacgtt tttaagtatt gtttagttgc tctttcgaca tatatgatta tccctgcgcg   2520
gctaaagtta aggatgcaaa aaacataaga caactgaagt taatttacgt caattaagtt   2580
ttccagggta atgatgtttt gggcttccac taattcaata agtatgtcat gaaatacgtt   2640
gtgaagagca tccagaaata atgaaaagaa acaacgaaac tgggtcggcc tgttgtttct   2700
tttctttacc acgtgatctg cggcatttac aggaagtcgc gcgttttgcg cagttgttgc   2760
aacgcagcta cggctaacaa agcctagtgg aactcgactg atgtgttagg gcctaaaact   2820
ggtggtgaca gctgaagtga actattcaat ccaatcatgt catggctgtc acaaagacct   2880
tgcggaccgc acgtacgaac acatacgtat gctaatatgt gttttgatag tacccagtga   2940
tcgcagacct gcaatttttt tgtaggtttg gaagaatata taaaggttgc actcattcaa   3000
gatagttttt ttcttgtgtg tctattcatt ttattattgt ttgtttaaat gttaaaaaaa   3060
ccaagaactt agtttcaaat taaattcatc acacaaacaa acaaaacaaa atgaacattg   3120
ttgtttgttt gaagcaagtt ccagacactg ctgaagtcag aattgaccca gtcaagggta   3180
ctttaatcag agaaggtgtt ccatctatca tcaacccaga cgacaagaac gctttggaag   3240
aagctttggt tttgaaggac aactacggtg ctcacgttac cgtcatttcc atgggtccac   3300
```

```
ctcaagccaa gaacgctttg gttgaagctt tggccatggg tgctgatgaa gctgtcttat    3360
tgactgacag agctttcggt ggtgctgata ctttagctac ctctcacacc attgctgctg    3420
gtatcaagaa attgaaatac gatatcgtct ttgccggtcg tcaagccatc gatggtgata    3480
ccgctcaagt cggtccagaa attgctgaac atttgggtat tccacaagtc acctacgttg    3540
aaaaggttga agttgacggt gacactttga agatcagaaa ggcttgggaa gacggttacg    3600
aagttgttga agtcaagact ccagttctat tgactgccat caaggaattg aacgttccaa    3660
gatacatgtc cgttgaaaag atcttcggtg ctttcgacaa ggaagtcaag atgtggactg    3720
ctgatgatat cgatgtcgac aaggccaact gggtttgaa aggttctcca accaaggtca    3780
agaaatcttc taccaaggaa gtcaagggtc aaggtgaagt cattgacaaa ccagtcaagg    3840
aagctgccgc ttacgttgtt tccaagttga aggaagaaca ctacatctaa agcccgggcg    3900
gagattgata agacttttct agttgcatat cttttatatt taaatcttat ctattagtta    3960
attttttgta atttatcctt atatatagtc tggttattct aaaatatcat ttcagtatct    4020
aaaaattccc ctctttttc agttatatct taacaggcga cagtccaaat gttgatttat    4080
cccagtccga ttcatcaggg ttgtgaagca ttttgtcaat ggtcgaaatc acatcagtaa    4140
tagtgcctct tacttgcctc atagaatttc tttctcttaa cgtcaccgtt tggtctttta    4200
tagtttcgaa atctatggtg ataccaaatg gtgttcccaa ttcatcgtta cgggcgtatt    4260
ttttaccaat tgaagtattg gaatcgtcaa ttttaaagta tatctctctt ttacgtaaag    4320
cctgcgagat cctcttaagt atagcgggga agccatcgtt attcgatatt gtcgtaacaa    4380
atactttgat cggcgctatg tttaaatgtt taaacatgga cagatatgcg atgaaaacgc    4440
taagtgatac tccaaatggt gaaaggtacg atgcttggaa acaatacttg gaaatcaccg    4500
gaaacaccat atgcggcgaa aagccaatta gtgtgatact aagtgcttta tcgaaaatcc    4560
gtgatgccgg tccttcaggc atcaaatttc agtggcctaa ttattcacag agttctcatg    4620
tgacaagtat tgatgatagt agtgtcagtt atgcttcagg ttatgttact ataggataat    4680
gatcacggct aaaacggtcg aatgtaagca tatatctttc gattgtataa ttgttcccaa    4740
atactacagc atctcaagga aaaaaaaaca aaaacttcca aaaaaatcga atccctgagg    4800
aatctttaat acattttcaa tctatttaag ttttataaac gtgtatatga gatgtcatga    4860
gcatgaatta ttaataataa aaactaaatc attaaagtaa cttaaggagt taaagcccgg    4920
gctttaattg ttagcagcct tgacttgagc aatcaattct ggaacaacct tgttgacatc    4980
accgacaatg gccaaatcag caaccttcat gattggagct cgacatcttt tgttgatggc    5040
aatgatgtag tcagagtctt gcataccagc caagtgttgg atggcaccag agataccaca    5100
agcaatgtac aaagttggtc tgacggtctt accggtttga ccgacttgca agtccttgtc    5160
aacccattcc tttcaatgg cagctctgga agcagcaatg gtaccaccca caaagaagc    5220 taattcttcc aatttttcga agttttcctt ggaaccaaca ccacgaccac cagcaaccaa    5280
aaccttggct tcaccgatat cagcaatgtc cttggccaat ttgacaacct tggaaacctt    5340
ggttctgata tcagaagcag tcaatttgat ggcaacctt tcgatcttgt catcagaaac    5400
gttagcatcg ttaactggca ttttcaaa gacacctggt ctgacggtgg ccatttgagg    5460
tctgtggtca gaacagacaa tggtagcaat caagttacca ccgaaagctg gtctggtagc    5520
caacaagtca cggttttcga catcgatatc caaagaggta cagtcagcag tcaaaccagt    5580
agacaatctg gcagcaattc ttggacccaa gtctctaccg atgaaagtag caccgatgaa    5640
```

```
taagatttct ggctttcttt cgttgaccaa gtcacagata accttggcgt aaccgtcagt      5700
ggagaaatga gctaataatt cgttgtcagc agccaaaacc ttgtcagcac cgtgggacaa      5760
caagtccttg gacatctttt cagtgttgtg acccaataag acagcagtca attcaacacc      5820
caattttcca gccatttcct taccettacc tagcaattcc aaagaaacct tttgtaattc      5880
accatctctt tgttcagcga aacccagac acccttgtag tcagccttgt tcatgtttag       5940
ttaattatag ttcgttgacc gtatattcta aaaacaagta ctccttaaaa aaaaaccttg      6000
aagggaataa acaagtagaa tagatagaga gaaaaataga aaatgcaaga gaatttatat     6060
attagaaaga gagaaagaaa aatggaaaaa aaaaatagg aaaagccaga aatagcacta      6120
gaaggagcga caccagaaaa gaaggtgatg gaaccaattt agctatatat agttaactac     6180
cggctcgatc atctctgcct ccagcatagt cgaagaagaa tttttttttt cttgaggctt      6240
ctgtcagcaa ctcgtatttt ttctttcttt tttggtgagc ctaaaaagtt cccacgttct      6300
cttgtacgac gccgtcacaa acaacctat gggtaatttg tcgcggtctg ggtgtataaa      6360
tgtgtgggtg caggccggcc gtttaaacgg gccgccaccg cggtggagcc tgtgtggaag     6420
aacgattaca acaggtgttg tcctctgagg acataaaata cacaccgaga ttcatcaact     6480
cattgctgga gttagcatat ctacaattgg gtgaaatggg gagcgatttg caggcatttg     6540
ctcggcatgc cggtagaggt gtggtcaata agagcgacct catgctatac ctgagaaagc     6600
aacctgacct acaggaaaga gttactcaag aataagaatt ttcgttttaa aacctaagag     6660
tcactttaaa atttgtatac acttatttt ttataactt atttaataat aaaaatcata      6720
aatcataaga aattcgctcg agtcgactgc agtttactgc ttgtagtcgt aagaagtttg     6780
gatgatatcc ttgatttcag aaatcaaagc ttcctttggg ttggcagtgg tacattggtc     6840
ttcgaaagcc aattcagcca ttctgtcaat ggattcgttc aattcttctt cagagacacc     6900
ttgagatttc aagttcattt caataccaac agattgacct aattcgtaga cagccttggc     6960
caaagattca accaaagctt cagtggtgtt acctttcaaa cctaagaact tggcgatatc     7020
agcgtaatcg gtgtcagctc tgaagaattc gtactttggg aacaaagcgt gcttttgagg     7080
gtccttggcg ttgtatctga tgatgtgagg caacaagatg gcgttagctc taccatgtgg    7140
aataccgtat tcaccaccaa ttttgtgagc aatggagtga gcaatacca agaaagcgtt     7200 agcaaaggcc ataccggcca agtagaagc gttgtgcatc ttttctctgg aaaccttgtc      7260 accttttca acggaagatt tcaagtattc aaaggtcaat ttgatagctt gtagggacaa      7320
acctctggtg taatcggagg ccatgacaga aacgtaagat tccatagcgt gagtcaaaac     7380
gtccataccg gtatcagcag tgacagattt tgggacggac atgacaaatt gagggtcaat     7440
gatggcgaca tctggagtca aagcgaaatc agccaatggg tatttgacgt tggtttcaga     7500
gtcagtgata acagcaaatg gagtgacttc agaaccagta ccagaagtgg ttggaataca    7560
gatgaaagtg gcgttttctg gcataccaat cttgtaggtt ctcttaccaa tgtccaagaa    7620
tttttgcttg gcaccgaaga aagaagtttc tggatgttcg aagaacatcc acatagcctt   7680
ggcagcatcc atggcagaac caccacccaa agcaatgatg gtgtctggtt ggaaatcgac     7740
catcatttcc aaacccttgt agacagtgtt ggtggatgga tttggttcaa cttcagagaa    7800
gatcttgatt tgaggttgtt cagttctttg acgtaagacg ttttcgacgg ttttggtgta   7860
accaaattca accatacctg ggtcacaaac gatcatgacc ttttcaatct tgtccatggt    7920
ggtcaaggac atgatagcgt tttcttcgaa atagatttga gctggaacct tgaagatttg    7980
agtgttgttt cttctcttgg caatggtctt gatgttcaac aaatcggtag cagagacgtt    8040
```

```
gtgggagatg gagtttctac cgtaagaacc acaacccaaa gtcaaggatg gaatcaattc    8100
gttgtacatg tcaccgatac caccaacagc agatggagtg ttgaccaaaa cacgacaagc    8160
cttcattctt agaccgaaat ccttttgcaa agtttcgtct tcagtgtgga taacagcagt    8220
gtgacctaaa ccaccgaagt gcaaagtgtc ttcacagatt tggaaagctt gcttggtaga    8280
ttgagccttg actaaagcca aaactggaga caacttttct ctggacaatg ggtagtcaga    8340
accgacaccg gagatttcag caatgatcaa tttggtgttt tctggaactg ggataccggc    8400
caattcagca atttcaacag cagacttacc aacgatatct ggcttgatac cagtcttttg    8460
ttcgttcatg atggcgtttt ctaatctttg taattcgtcc ttcttgacga agtaagcttg    8520
gtgagccttg aattcattgg tgacatcctt gtagatttcc ttgtcaatga caacaacttg    8580
ttcagaagca cagatcatac cattatcgaa agtcttggaa ccgatgatat cgttgacagc    8640
acgcttgata tgagcagtct tttcgatgta agatggaacg ttacctggac caacacccaa    8700
agctggttta ccagtggagt aagcagactt aaccatacca gaaccaccgg tagccaagac    8760
taaagcaata cccttgtggt tcatcaattg cttggtagct tcaatggatg gaacttcaat    8820
ccattggatg atatcctttg gagcaccagc cttcatggca gcttccaaaa caacttcagc    8880
agctctcttg gaagattctt gagcagatgg gtggaaagcg aaaataattg ggttaccagt    8940
cttgatggca atcatagcct tgaagatggt ggtagaagtt gggttggtgg ttggagtgac    9000
accacagatg acaccaattg gttcagcaac gtaggtcaaa cccttttctt tgtcttcacc    9060
aatgatacca acagtcttgt tgtccttgat ggagttccag atgtattcag aggcgtataa    9120
gttcttgata gccttgtctt cgtagatacc tctaccggtt tcttcatgag ccaacttggc    9180
caaaaccatg tgttggtcaa cagcagccaa ggacatttgg tggacaatgt ggtcaatttc    9240
ttcttgagac ttcttggaca aagcttccaa agccttctta cctttgtcag ctaaagcatc    9300
aatcatgatg gcaacttctt gttccttgga acctctgttt tccttttctg gaatggtcaa    9360
catttttttac tagttctaga atccgtcgaa actaagttct ggtgttttaa aactaaaaaa    9420
aagactaact ataaaagtag aatttaagaa gtttaagaaa tagatttaca gaattacaat    9480
caatacctac cgtctttata tacttattag tcaagtaggg gaataatttc agggaactgg    9540
tttcaaccTt tttttTcagc ttttTccaaa tcagagagag cagaaggtaa tagaaggtgt    9600
aagaaaatga gatagataca tgcgtgggtc aattgccttg tgtcatcatt tactccaggc    9660
aggttgcatc actccattga ggttgtgccc gttttttgcc tgtttgtgcc cctgttctct    9720
gtagttgcgc taagagaatg gacctatgaa ctgatggttg gtgaagaaaa caatattttg    9780
gtgctgggat tctttttttt tctggatgcc agcttaaaaa gcgggctcca ttatatttag    9840
tggatgccag gaataaactg ttcacccaga cacctcgat gttatatatt ctgtgtaacc     9900
cgcccctat tttgggcatg tacgggttac agcagaatta aaaggctaat ttttgactta    9960
aataaagtta ggaaaatcac tactattaat tatttacgta ttctttgaaa tggcgagtat   10020
tgataatgat aaactgagct ccagcttttg ttccctttag tgagggttaa ttgcgcgctt   10080
ggcgtaatca tggtcatagc tgtttcctgt gtgaaattgt tatccgctca caattccaca   10140
caacatagga gccggaagca taaagtgtaa agcctggggt gcctaatgag tgaggtaact   10200
cacattaatt gcgttgcgct cactgcccgc tttccagtcg ggaaacctgt cgtgccagct   10260
gcattaatga atcggccaac gcgcgggag aggcggtttg cgtattgggc gctcttccgc    10320
ttcctcgctc actgactcgc tgcgctcggt cgttcggctg cggcgagcgg tatcagctca   10380
```

```
ctcaaaggcg gtaatacggt tatccacaga atcaggggat aacgcaggaa agaacatgtg   10440
agcaaaaggc cagcaaaagg ccaggaaccg taaaaaggcc gcgttgctgg cgttttccca   10500
taggctccgc cccctgacg agcatcacaa aaatcgacgc tcaagtcaga ggtggcgaaa    10560
cccgacagga ctataaagat accaggcgtt tccccctgga agctccctcg tgcgctctcc   10620
tgttccgacc ctgccgctta ccggatacct gtccgccttt ctcccttcgg gaagcgtggc   10680
gctttctcat agctcacgct gtaggtatct cagttcggtg taggtcgttc gctccaagct   10740
gggctgtgtg cacgaacccc ccgttcagcc cgaccgctgc gccttatccg gtaactatcg   10800
tcttgagtcc aacccggtaa gacacgactt atcgccactg gcagcagcca ctggtaacag   10860
gattagcaga gcgaggtatg taggcggtgc tacagagttc ttgaagtggt ggcctaacta   10920
cggctacact agaaggacag tatttggtat ctgcgctctg ctgaagccag ttaccttcgg   10980
aaaaagagtt ggtagctctt gatccggcaa acaaaccacc gctggtagcg gtggtttttt   11040
tgtttgcaag cagcagatta cgcgcagaaa aaaaggatct caagaagatc ctttgatctt   11100
ttctacgggg tctgacgctc agtggaacga aaactcacgt taagggattt tggtcatgag   11160
attatcaaaa aggatcttca cctagatcct tttaaattaa aaatgaagtt ttaaatcaat   11220
ctaaagtata tatgagtaaa cttggtctga cagttaccaa tgcttaatca gtgaggcacc   11280
tatctcagcg atctgtctat ttcgttcatc catagttgcc tgactccccg tcgtgtagat   11340
aactacgata cgggagggct taccatctgg ccccagtgct gcaatgatac cgcgagaccc   11400
acgctcaccg gctccagatt tatcagcaat aaaccagcca gccggaaggg ccgagcgcag   11460
aagtggtcct gcaactttat ccgcctccat ccagtctatt aattgttgcc gggaagctag   11520
agtaagtagt tcgccagtta atagtttgcg caacgttgtt gccattgcta caggcatcgt   11580
ggtgtcacgc tcgtcgtttg gtatggcttc attcagctcc ggttcccaac gatcaaggcg   11640
agttacatga tcccccatgt tgtgcaaaaa agcggttagc tccttcggtc ctccgatcgt   11700
tgtcagaagt aagttggccg cagtgttatc actcatggtt atggcagcac tgcataattc   11760
tcttactgtc atgccatccg taagatgctt ttctgtgact ggtgagtact caaccaagtc   11820
attctgagaa tagtgtatgc ggcgaccgag ttgctcttgc ccggcgtcaa tacgggataa   11880
taccgcgcca catagcagaa ctttaaaagt gctcatcatt ggaaaacgtt cttcggggcg   11940
aaaactctca aggatcttac cgctgttgag atccagttcg atgtaaccca ctcgtgcacc   12000
caactgatct tcagcatctt ttactttcac cagcgtttct gggtgagcaa aaacaggaag   12060
gcaaaatgcc gcaaaaaagg gaataagggc gacacggaaa tgttgaatac tcatactctt   12120
cctttttcaa tattattgaa gcatttatca gggttattgt ctcatgagcg gatacatatt   12180
tgaatgtatt tagaaaaata aacaaatagg ggttccgcgc acatttcccc gaaaagtgcc   12240
acctgacgtc taagaaacca ttattatcat gacattaacc tataaaaata ggcgtatcac   12300
gaggcccttt cgtc                                                   12314

<210> SEQ ID NO 45
<211> LENGTH: 11180
<212> TYPE: DNA
<213> ORGANISM: Artificial
<220> FEATURE:
<223> OTHER INFORMATION: pBOL116

<400> SEQUENCE: 45
tcgcgcgttt cggtgatgac ggtgaaaacc tctgacacat gcagctcccg gagacggtca   60
cagcttgtct gtaagcggat gccgggagca gacaagcccg tcagggcgcg tcagcgggtg   120
```

```
ttggcgggtg tcggggctgg cttaactatg cggcatcaga gcagattgta ctgagagtgc    180
accataccac agcttttcaa ttcaattcat cattttttttt ttattctttt ttttgatttc   240
ggtttctttg aaattttttt gattcggtaa tctccgaaca gaaggaagaa cgaaggaagg    300
agcacagact tagattggta tatatacgca tatgtagtgt tgaagaaaca tgaaattgcc    360
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaaacacatg    600
tggatatctt gactgatttt tccatggagg gcacagttaa gccgctaaag gcattatccg    660
ccaagtacaa tttttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggcctttg atgttagcag aattgtcatg caagggctcc ctatctactg     900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactattt gcaaagggaa   1140
gggatgctaa ggtagaggt gaacgttaca gaaaagcagg ctgggaagca tatttgagaa     1200
gatgcggcca gcaaaactaa aaaactgtat tataagtaaa tgcatgtata ctaaactcac   1260
aaattagagc ttcaatttaa ttatatcagt tattaccta tgcggtgtga ataccgcac     1320
agatgcgtaa ggagaaaata ccgcatcagg aaattgtaaa cgttaatatt ttgttaaaat   1380
tcgcgttaaa ttttttgttaa atcagctcat tttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg gcgaaaaacc gtctatcagg   1560
gcgatggccc actacgtgaa ccatcaccct aatcaagttt tttggggtcg aggtgccgta   1620
aagcactaaa tcggaaccct aaagggagcc ccgatttag agcttgacgg ggaaagccgg     1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact ataggggcgaa ttgggtaccg ggccccccct cgaggtcgac ggtatcgata   2040
agcttgatat cgaattcctg cagcccgggg gatccactag ttctagagcg cccatttaa    2100
acggccggcc ctagatcaga gggtggtaaa tgaagtgtaa tagtattcat ttttcttata   2160
aatcatccct tccgtgattt atacaaaaga gagagaat atgctgaata cttggtatat     2220
tactctacat tatactctta tcttgacggg tattctgagc atcttactca gtttcaagat   2280
cttttaatgt ccaaaaacat ttgagccgat ctaaatactt ctgtgttttc attaatttat   2340
aaattgtact ctttaagac atggaaagta ccaacatcgg ttgaaacagt ttttcatta    2400
cttatggttt attggttttt ccagtgaatg attatttgtc gttaccctt cgtaaaagtt    2460
```

```
caaacacgtt tttaagtatt gtttagttgc tctttcgaca tatatgatta tccctgcgcg   2520
gctaaagtta aggatgcaaa aaacataaga caactgaagt taatttacgt caattaagtt   2580
ttccagggta atgatgtttt gggcttccac taattcaata agtatgtcat gaaatacgtt   2640
gtgaagagca tccagaaaata atgaaaagaa acaacgaaac tgggtcggcc tgttgtttct   2700
tttctttacc acgtgatctg cggcatttac aggaagtcgc gcgttttgcg cagttgttgc   2760
aacgcagcta cggctaacaa agcctagtgg aactcgactg atgtgttagg gcctaaaact   2820
ggtggtgaca gctgaagtga actattcaat ccaatcatgt catggctgtc acaaagacct   2880
tgcggaccgc acgtacgaac acatacgtat gctaatatgt gttttgatag tacccagtga   2940
tcgcagacct gcaattttt tgtaggtttg aagaatata taaaggttgc actcattcaa   3000
gatagttttt ttcttgtgtg tctattcatt ttattattgt ttgtttaaat gttaaaaaaa   3060
ccaagaactt agtttcaaat taaattcatc acacaaacaa acaaaacaaa atgaacattg   3120
ttgtttgttt gaagcaagtt ccagacactg ctgaagtcag aattgaccca gtcaagggta   3180
ctttaatcag agaaggtgtt ccatctatca tcaacccaga cgacaagaac gctttggaag   3240
aagctttggt tttgaaggac aactacggtc tcacgttac cgtcatttcc atgggtccac   3300
ctcaagccaa gaacgctttg gttgaagctt tggccatggg tgctgatgaa gctgtcttat   3360
tgactgacag agctttcggt ggtgctgata ctttagctac ctctcacacc attgctgctg   3420
gtatcaagaa attgaaatac gatatcgtct ttgccggtcg tcaagccatc gatggtgata   3480
ccgctcaagt cggtccagaa attgctgaac atttgggtat tccacaagtc acctacgttg   3540
aaaaggttga agttgacggt gacactttga agatcagaaa ggcttgggaa gacggttacg   3600
aagttgttga agtcaagact ccagttctat tgactgccat caaggaattg aacgttccaa   3660
gatacatgtc cgttgaaaag atcttcggtg ctttcgacaa ggaagtcaag atgtggactg   3720
ctgatgatat cgatgtcgac aaggccaact tgggtttgaa aggttctcca accaaggtca   3780
agaaatcttc taccaaggaa gtcaagggtc aaggtgaagt cattgacaaa ccagtcaagg   3840
aagctgccgc ttacgttgtt ccaagttga aggaagaaca ctacatctaa gcccgggcg   3900 gagattgata agacttttct agttgcatat cttttatatt taaatcttat ctattagtta   3960
attttttgta atttatcctt atatatagtc tggttattct aaaatatcat ttcagtatct   4020
aaaaattccc ctcttttttc agttatatct taacaggcga cagtccaaat gttgatttat   4080
cccagtccga ttcatcaggg ttgtgaagca ttttgtcaat ggtcgaaatc acatcagtaa   4140
tagtgcctct tacttgcctc atagaatttc tttctcttaa cgtcaccgtt tggtctttta   4200
tagtttcgaa atctatggtg ataccaaatg gtgttcccaa ttcatcgtta cgggcgtatt   4260
ttttaccaat tgaagtattg gaatcgtcaa ttttaaagta tatctctctt ttacgtaaag   4320
cctgcgagat cctcttaagt atagcgggga agccatcgtt attcgatatt gtcgtaacaa   4380
atactttgat cggcgctatg tttaaatgtt taaacatgga cagatatgcg atgaaaacgc   4440
taagtgatac tccaaatggt gaaaggtacg atgcttggaa acaatacttg gaaatcaccg   4500
gaaacaccat atgcggcgaa aagccaatta gtgtgatact aagtgcttta tcgaaaatcc   4560
gtgatgccgg tccttcaggc atcaaatttc agtggcctaa ttattcacag agttctcatg   4620
tgacaagtat tgatgatagt agtgtcagtt atgcttcagg ttatgttact ataggataat   4680
gatcacggct aaaacggtcg aatgtaagca tatatctttc gattgtataa ttgttcccaa   4740
atactacagc atctcaagga aaaaaaaaca aaaacttcca aaaaaatcga atccctgagg   4800
aatctttaat acattttcaa tctatttaag ttttataaac gtgtatatga gatgtcatga   4860
```

```
gcatgaatta ttaataataa aaactaaatc attaaagtaa cttaaggagt taaagcccgg   4920
gctttaattg ttagcagcct tgacttgagc aatcaattct ggaacaacct tgttgacatc   4980
accgacaatg gccaaatcag caaccttcat gattggagct tcgacatctt tgttgatggc   5040
aatgatgtag tcagagtctt gcataccagc caagtgttgg atggcaccag agataccaca   5100
agcaatgtac aaagttggtc tgacggtctt accggtttga ccgacttgca agtccttgtc   5160
aacccattcc ttttcaatgg cagctctgga agcagcaatg gtaccaccca acaaagaagc   5220
taattcttcc aattttcga gttttcctt ggaaccaaca ccacgaccac cagcaaccaa   5280
aaccttggct tcaccgatat cagcaatgtc cttggccaat tgacaacct tggaaacctt   5340 ggttctgata tcagaagcag tcaatttgat ggcaacctt tcgatcttgt catcagaaac   5400
gttagcatcg ttaactggca attttcaaa gacacctggt ctgacggtgg ccatttgagg   5460
tctgtggtca gaacagacaa tggtagcaat caagttacca ccgaaagctg gtctggtagc   5520
caacaagtca cggttttcga catcgatatc caaagaggta cagtcagcag tcaaaccagt   5580
agacaatctg gcagcaattc ttggacccaa gtctctaccg atgaaagtag caccgatgaa   5640
taagatttct ggctttcttt cgttgaccaa gtcacagata accttggcgt aaccgtcagt   5700
ggagaaatga gctaataatt cgttgtcagc agccaaaacc ttgtcagcac cgtgggacaa   5760
caagtccttg gacatctttt cagtgttgtg acccaataag acagcagtca attcaacacc   5820 caattttca gccatttcct taccttacc tagcaattcc aaagaaacct tttgtaattc   5880
accatctctt tgttcagcga aaacccagac acccttgtag tcagccttgt tcatgtttag   5940
ttaattatag ttcgttgacc gtatattcta aaaacaagta ctccttaaaa aaaaaccttg   6000
aagggaataa acaagtagaa tagatagaga gaaaaataga aatgcaaga gaatttatat   6060 attagaaaga gagaaagaaa aatggaaaaa aaaaaatagg aaaagccaga aatagcacta   6120
gaaggagcga caccgaaaaa gaaggtgatg gaaccaattt agctatatat agttaactac   6180
cggctcgatc atctctgcct ccagcatagt cgaagaagaa ttttttttt cttgaggctt   6240 ctgtcagcaa ctcgtatttt ttctttcttt tttggtgagc ctaaaaagtt cccacgttct   6300
cttgtacgac gccgtcacaa acaaccttat gggtaatttg tcgcggtctg ggtgtataaa   6360
tgtgtgggtg caggccggcc gtttaaacgg gccgccaccg cggtggagcc tgtgtggaag   6420
aacgattaca acaggtgttg tcctctgagg acataaaata cacaccgaga ttcatcaact   6480
cattgctgga gttagcatat ctacaattgg gtgaaatggg gagcgatttg caggcatttg   6540
ctcggcatgc cggtagaggt gtggtcaata agagcgacct catgctatac ctgagaaagc   6600
aacctgacct acaggaaaga gttactcaag aataagaatt ttcgttttaa aacctaagag   6660
tcactttaaa atttgtatac acttattttt tttataactt atttaataat aaaaatcata   6720
aatcataaga aattcgctcg agtcgactgc agtttacaag ttcaatttgg ccatgatggc   6780
cttaacaatg gcttgaacat cttcgttgtc ttctggttca gctggagcag aagaagaagc   6840
agcaccgaca ccgaaagctt ctctgatttc ttcgacggtg gtggtaccgt aagcaacctt   6900
tctgatgttg aacaagtttt ctggaccaac gttgtcagag gtggcagaac caccaacagc   6960
accacaacct aaagtcaaag atgggactaa gttggtagca ccaccgatac cacccaaaga   7020
acctggagag ttaaccaaaa ttctggaaac aggcttcttc aaagcaaatt ctctaatgat   7080
ttcttcgttt tgagagtgga tgatcaaagt gtgaccagaa ccttggttgt gcaataaagc   7140
caaagacttt tcacaagctt catgccagtc ttcgacggtg tagaaagcca agactggagc   7200
```

```
caattttttcc ttagcgtatg gattttttagg agaaacatcg gtttgttcgg atagtaagat    7260
aacagcatca gatggaatgg aaataccagc caatttggcc aaagcttgga catccttacc    7320
aacgatggct gggtttggag taccgttggc acgtaataga atcttaccaa ccttttcaga    7380
ttcttcagca ttcaagaagt aacccttttg tctcttgaat tcttcgatga tttcagcctt    7440
cttgacggtt tcagcaatga tggattgttc agaagcacag atgacaccgt tgtcgaaagt    7500
gtcagaaccg ataacctttc taacagcagt tggaatgtca gcagttcttt cgatgaaaca    7560
tggaccgtta cctggaccga caccgatggc tggagtacca gaggagtaag cagctctaac    7620 catacccttca ccaccggtag ccaagatcaa agcggtgtcc ttgttcttca tcaattcagc    7680
agtaccttca acggtcaaaa tggacataca ttggatcaaa ccatctggag caccagcttc    7740
aacagcagcc ttttgcatga tcttaacggt ttcagtgatg aacggacag cagttgggtg    7800 tggagagaag acaatggcgt taccagcctt caaagcaatc aagaccttga aaatggcagt    7860
ggaagttggg ttggtagatg gaatcaaacc agcaatgaca cctaatggga cagcaatgtc    7920
aatcaatttc ttttccttgt cttccttcaa gataccaacg gtcttcaaat ccttgatgta    7980
gttgtagaca acaatggagg agaatttgtt cttgatgacc ttgtcttccc atttaccgta    8040
accggtgtct tcgtaagcca atttggccaa tttgacagct tcaacttcag tagccttggc    8100
gatcttttcg atgaccttgt taacagcttc ttgggaaaag ttcttgaatt cagcttgagc    8160
cttcttggcc ttggcaatca aagttctaac ttccttggatg gattgcaaat ccttgtccat    8220
gatttccatt ttttactagt tctagaatcc gtcgaaacta agttctggtg tttttaaaact    8280 aaaaaaaaga ctaactataa aagtagaatt taagaagttt aagaaataga tttacagaat    8340
tacaatcaat acctaccgtc tttatatact tattagtcaa gtaggggaat aatttcaggg    8400
aactggtttc aacctttttt ttcagctttt tccaaatcag agagagcaga aggtaataga    8460
aggtgtaaga aaatgagata gatacatgcg tgggtcaatt gccttgtgtc atcatttact    8520
ccaggcaggt tgcatcactc cattgaggtt gtgcccgttt tttgcctgtt tgtgcccctg    8580
ttctctgtag ttgcgctaag agaatggacc tatgaactga tggttggtga agaaaacaat    8640
attttggtgc tgggattctt ttttttttctg gatgccagct taaaaagcgg gctccattat    8700
atttagtgga tgccaggaat aaactgttca cccagacacc tacgatgtta tatattctgt    8760
gtaacccgcc ccctattttg ggcatgtacg ggttacagca gaattaaaag gctaattttt    8820
tgactaaata aagttaggaa aatcactact attaattatt tacgtattct ttgaaatggc    8880
gagtattgat aatgataaac tgagctccag cttttgttcc ctttagtgag ggttaattgc    8940
gcgcttggcg taatcatggt catagctgtt tcctgtgtga aattgttatc cgctcacaat    9000
tccacacaac ataggagccg gaagcataaa gtgtaaagcc tggggtgcct aatgagtgag    9060
gtaactcaca ttaattgcgt tgcgctcact gcccgctttc cagtcgggaa acctgtcgtg    9120
ccagctgcat taatgaatcg gccaacgcgc ggggagaggc ggtttgcgta ttgggcgctc    9180
ttccgcttcc tcgctcactg actcgctgcg ctcggtcgtt cggctgcggc gagcggtatc    9240
agctcactca aaggcggtaa tacggttatc cacagaatca ggggataacg caggaaagaa    9300
catgtgagca aaaggccagc aaaaggccag gaaccgtaaa aaggccgcgt tgctggcgtt    9360
tttccatagg ctccgccccc ctgacgagca tcacaaaaat cgacgctcaa gtcagaggtg    9420
gcgaaacccg acaggactat aaagatacca ggcgtttccc cctggaagct ccctcgtgcg    9480
ctctcctgtt ccgaccctgc cgcttaccgg atacctgtcc gcctttctcc cttcgggaag    9540
cgtggcgctt tctcatagct cacgctgtag gtatctcagt tcggtgtagg tcgttcgctc    9600
```

```
caagctgggc tgtgtgcacg aaccccccgt tcagcccgac cgctgcgcct tatccggtaa    9660
ctatcgtctt gagtccaacc cggtaagaca cgacttatcg ccactggcag cagccactgg    9720
taacaggatt agcagagcga ggtatgtagg cggtgctaca gagttcttga agtggtggcc    9780
taactacggc tacactagaa ggacagtatt tggtatctgc gctctgctga agccagttac    9840
cttcggaaaa agagttggta gctcttgatc cggcaaacaa accaccgctg gtagcggtgg    9900
tttttttgtt tgcaagcagc agattacgcg cagaaaaaaa ggatctcaag aagatccttt    9960
gatcttttct acggggtctg acgctcagtg aacgaaaac tcacgttaag ggattttggt    10020
catgagatta tcaaaaagga tcttcaccta gatccttta aattaaaaat gaagttttaa    10080
atcaatctaa agtatatatg agtaaacttg gtctgacagt taccaatgct taatcagtga    10140
ggcacctatc tcagcgatct gtctatttcg ttcatccata gttgcctgac tccccgtcgt    10200
gtagataact acgatacggg agggcttacc atctggcccc agtgctgcaa tgataccgcg    10260
agacccacgc tcaccggctc cagatttatc agcaataaac cagccagccg aagggccga    10320 gcgcagaagt ggtcctgcaa ctttatccgc ctccatccag tctattaatt gttgccggga    10380
agctagagta gtagttcgc cagttaatag tttgcgcaac gttgttgcca ttgctacagg    10440
catcgtggtg tcacgctcgt cgtttggtat ggcttcattc agctccggtt cccaacgatc    10500
aaggcgagtt acatgatccc ccatgttgtg caaaaaagcg gttagctcct tcggtcctcc    10560
gatcgttgtc agaagtaagt tggccgcagt gttatcactc atggttatgg cagcactgca    10620
taattctctt actgtcatgc catccgtaag atgcttttct gtgactggtg agtactcaac    10680
caagtcattc tgagaatagt gtatgcggcg accgagttgc tcttgcccgg cgtcaatacg    10740
ggataatacc gcgccacata gcagaacttt aaaagtgctc atcattggaa acgttcttc    10800 ggggcgaaaa ctctcaagga tcttaccgct gttgagatcc agttcgatgt aacccactcg    10860
tgcacccaac tgatcttcag catcttttac tttcaccagc gtttctgggt gagcaaaaac    10920
aggaaggcaa aatgccgcaa aaaagggaat aagggcgaca cggaaatgtt gaatactcat    10980
actcttcctt tttcaatatt attgaagcat ttatcagggt tattgtctca tgagcggata    11040
catatttgaa tgtatttaga aaaataaaca ataggggtt ccgcgcacat ttccccgaaa    11100
agtgccacct gacgtctaag aaaccattat tatcatgaca ttaacctata aaaataggcg    11160
tatcacgagg ccctttcgtc                                                11180
```

<210> SEQ ID NO 46
<211> LENGTH: 11108
<212> TYPE: DNA
<213> ORGANISM: Artificial
<220> FEATURE:
<223> OTHER INFORMATION: pBOL118

<400> SEQUENCE: 46

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accataccac agcttttcaa ttcaattcat catttttttt ttattctttt ttttgatttc     240
ggtttctttg aaatttttt gattcggtaa tctccgaaca gaaggaagaa cgaaggaagg     300
agcacagact tagattggta tatatacgca tatgtagtgt tgaagaaaca tgaaattgcc     360
cagtattctt aacccaactg cacagaacaa aaacctgcag gaaacgaaga taaatcatgt     420
```

| | |
|---|---|
| cgaaagctac atataaggaa cgtgctgcta ctcatcctag tcctgttgct gccaagctat | 480 |
| ttaatatcat gcacgaaaag caaacaaact tgtgtgcttc attggatgtt cgtaccacca | 540 |
| aggaattact ggagttagtt gaagcattag gtcccaaaat ttgtttacta aaaacacatg | 600 |
| tggatatctt gactgatttt tccatggagg gcacagttaa accgctaaag cattatccg | 660 |
| ccaagtacaa ttttttactc ttcgaagaca gaaaatttgc tgacattggt aatacagtca | 720 |
| aattgcagta ctctgcgggt gtatacagaa tagcagaatg ggcagacatt acgaatgcac | 780 |
| acggtgtggt gggcccaggt attgttagcg gtttgaagca ggcggcagaa gaagtaacaa | 840 |
| aggaacctag aggcctttg atgttagcag aattgtcatg caagggctcc ctatctactg | 900 |
| gagaatatac taagggtact gttgacattg cgaagagcga caaagatttt gttatcggct | 960 |
| ttattgctca aagagacatg ggtggaagag atgaaggtta cgattggttg attatgacac | 1020 |
| ccggtgtggg tttagatgac aagggagacg cattgggtca acagtataga accgtggatg | 1080 |
| atgtggtctc tacaggatct gacattatta ttgttggaag aggactattt gcaaagggaa | 1140 |
| gggatgctaa ggtagagggt gaacgttaca gaaaagcagg ctgggaagca tatttgagaa | 1200 |
| gatgcggcca gcaaaactaa aaaactgtat tataagtaaa tgcatgtata ctaaactcac | 1260 |
| aaattagagc ttcaatttaa ttatatcagt tattacccta tgcggtgtga aataccgcac | 1320 |
| agatgcgtaa ggagaaaata ccgcatcagg aaattgtaaa cgttaatatt ttgttaaaat | 1380 |
| tcgcgttaaa ttttgttaa atcagctcat tttttaacca ataggccgaa atcggcaaaa | 1440 |
| tcccttataa atcaaaagaa tagaccgaga tagggttgag tgttgttcca gtttggaaca | 1500 |
| agagtccact attaaagaac gtggactcca acgtcaaagg gcgaaaaacc gtctatcagg | 1560 |
| gcgatggccc actacgtgaa ccatcaccct aatcaagttt tttggggtcg aggtgccgta | 1620 |
| aagcactaaa tcggaaccct aaagggagcc cccgatttag agcttgacgg ggaaagccgg | 1680 |
| cgaacgtggc gagaaaggaa gggaagaaag cgaaaggagc gggcgctagg gcgctggcaa | 1740 |
| gtgtagcggt cacgctgcgc gtaaccacca cacccgccgc gcttaatgcg ccgctacagg | 1800 |
| gcgcgtcgcg ccattcgcca ttcaggctgc gcaactgttg ggaagggcga tcggtgcggg | 1860 |
| cctcttcgct attacgccag ctggcgaaag ggggatgtgc tgcaaggcga ttaagttggg | 1920 |
| taacgccagg gttttcccag tcacgacgtt gtaaaacgac ggccagtgag cgcgcgtaat | 1980 |
| acgactcact ataggggcgaa ttgggtaccg ggccccccct cgaggtcgac ggtatcgata | 2040 |
| agcttgatat cgaattcctg cagcccgggg gatccactag ttctagagcg gcccatttaa | 2100 |
| acggccggcc ctagatcaga gggtggtaaa tgaagtgtaa tagtattcat ttttcttata | 2160 |
| aatcatccct tccgtgattt atacaaaaga agaggagaat atgctgaata cttggtatat | 2220 |
| tactctacat tatactctta tcttgacggg tattctgagc atcttactca gtttcaagat | 2280 |
| ctttaatgt ccaaaaacat ttgagccgat ctaaatactt ctgtgttttc attaatttat | 2340 |
| aaattgtact cttttaagac atggaaagta ccaacatcgg ttgaaacagt ttttcattta | 2400 |
| cttatggttt attggttttt ccagtgaatg attatttgtc gttacccttt cgtaaaagtt | 2460 |
| caaacacgtt tttaagtatt gtttagttgc tctttcgaca tatatgatta tccctgcgcg | 2520 |
| gctaaagtta aggatgcaaa aaacataaga caactgaagt taatttacgt caattaagtt | 2580 |
| ttccagggta atgatgtttt gggcttccac taattcaata agtatgtcat gaaatacgtt | 2640 |
| gtgaagagca tccagaaaata atgaaaagaa acaacgaaac tgggtcggcc tgttgtttct | 2700 |
| tttctttacc acgtgatctg cggcatttac aggaagtcgc gcgttttgcg cagttgttgc | 2760 |
| aacgcagcta cggctaacaa agcctagtgg aactcgactg atgtgttagg gcctaaaact | 2820 |

```
ggtggtgaca gctgaagtga actattcaat ccaatcatgt catggctgtc acaaagacct    2880
tgcggaccgc acgtacgaac acatacgtat gctaatatgt gttttgatag tacccagtga    2940
tcgcagacct gcaatttttt tgtaggtttg gaagaatata taaaggttgc actcattcaa    3000
gatagttttt ttcttgtgtg tctattcatt ttattattgt ttgtttaaat gttaaaaaaa    3060
ccaagaactt agtttcaaat taaattcatc acacaaacaa acaaaacaaa atgaacattg    3120
ttgtttgttt gaagcaagtt ccagacactg ctgaagtcag aattgaccca gtcaagggta    3180 cttta atcag agaaggtgtt ccatctatca tcaacccaga cgacaagaac gctttggaag    3240
aagctttggt tttgaaggac aactacggtg ctcacgttac cgtcatttcc atgggtccac    3300
ctcaagccaa gaacgctttg gttgaagctt tggccatggg tgctgatgaa gctgtcttat    3360
tgactgacag agctttcggt ggtgctgata ctttagctac ctctcacacc attgctgctg    3420
gtatcaagaa attgaaatac gatatcgtct ttgccggtcg tcaagccatc gatggtgata    3480
ccgctcaagt cggtccagaa attgctgaac atttgggtat tccacaagtc acctacgttg    3540
aaaaggttga agttgacggt gacactttga agatcagaaa ggcttgggaa gacggttacg    3600
aagttgttga agtcaagact ccagttctat tgactgccat caaggaattg aacgttccaa    3660
gatacatgtc cgttgaaaag atcttcggtg ctttcgacaa ggaagtcaag atgtggactg    3720
ctgatgatat cgatgtcgac aaggccaact tgggtttgaa aggttctcca accaaggtca    3780
agaaatcttc taccaaggaa gtcaagggtc aaggtgaagt cattgacaaa ccagtcaagg    3840
aagctgccgc ttacgttgtt tccaagttga aggaagaaca ctacatctaa agcccgggcg    3900
gagattgata agacttttct agttgcatat ctttttatatt taaatcttat ctattagtta    3960 atttttgta atttatcctt atatatagtc tggttattct aaaatatcat ttcagtatct    4020
aaaaattccc ctctttttttc agtatatct taacaggcga cagtccaaat gttgatttat    4080
cccagtccga ttcatcaggg ttgtgaagca ttttgtcaat ggtcgaaatc acatcagtaa    4140
tagtgcctct tacttgcctc atagaatttc tttctcttaa cgtcaccgtt tggtcttta    4200 tagtttcgaa atctatggtg ataccaaatg gtgttcccaa ttcatcgtta cgggcgtatt    4260
ttttaccaat tgaagtattg gaatcgtcaa ttttaaagta tatctctctt ttacgtaaag    4320
cctgcgagat cctcttaagt atagcgggga agccatcgtt attcgatatt gtcgtaacaa    4380
atactttgat cggcgctatg tttaaatgtt taaacatgga cagatatgcg atgaaaacgc    4440
taagtgatac tccaaatggt gaaaggtacg atgcttggaa acaatacttg gaaatcaccg    4500
gaaacaccat atgcggcgaa aagccaatta gtgtgatact aagtgcttta tcgaaaatcc    4560
gtgatgccgg tccttcaggc atcaaatttc agtggcctaa ttattcacag agttctcatg    4620
tgacaagtat tgatgatagt agtgtcagtt atgcttcagg ttatgttact ataggataat    4680
gatcacggct aaaacggtcg aatgtaagca tatatctttc gattgtataa ttgttcccaa    4740
atactacagc atctcaagga aaaaaaaaca aaaacttcca aaaaaatcga atccctgagg    4800
aatctttaat acatttttcaa tctatttaag ttttataaac gtgtatatga gatgtcatga    4860
gcatgaatta ttaataataa aaactaaatc attaaagtaa cttaaggagt taaagcccgg    4920
gctttaattg ttagcagcct tgacttgagc aatcaattct ggaacaacct tgttgacatc    4980
accgacaatg gccaaatcag caaccttcat gattggagct tcgacatctt tgttgatggc    5040
aatgatgtag tcgagtcttt gcataccagc caagtgttgg atggcaccag agataccaca    5100
agcaatgtac aaagttggtc tgacggtctt accggtttga ccgacttgca agtccttgtc    5160
```

```
aacccattcc tttttcaatgg cagctctgga agcagcaatg gtaccaccca acaaagaagc    5220
taattcttcc aattttttcga agttttcctt ggaaccaaca ccacgaccac cagcaaccaa    5280
aaccttggct tcaccgatat cagcaatgtc cttggccaat ttgacaacct tggaaacctt    5340
ggttctgata tcagaagcag tcaatttgat ggcaacctttt tcgatcttgt catcagaaac    5400
gttagcatcg ttaactggca atttttcaaa gacacctggt ctgacggtgg ccatttgagg    5460
tctgtggtca gaacagacaa tggtagcaat caagttacca ccgaaagctg gtctggtagc    5520
caacaagtca cggttttcga catcgatatc caaagaggta cagtcagcag tcaaaccagt    5580
agacaatctg gcagcaattc ttggacccaa gtctctaccg atgaaagtag caccgatgaa    5640
taagatttct ggctttctttt cgttgaccaa gtcacagata accttggcgt aaccgtcagt    5700
ggagaaatga gctaataatt cgttgtcagc agccaaaacc ttgtcagcac cgtgggacaa    5760
caagtccttg gacatctttt cagtgttgtg acccaataag acagcagtca attcaacacc    5820
caatttttca gccatttcct taccccttacc tagcaattcc aaagaaacct tttgtaattc    5880
accatctctt tgttcagcga aacccagac acccttgtag tcagccttgt tcatgtttag    5940
ttaattatag ttcgttgacc gtatattcta aaaacaagta ctccttaaaa aaaaaccttg    6000
aagggaataa acaagtagaa tagatagaga gaaaaataga aatgcaaga gaatttatat    6060 attagaaaga gagaaagaaa aatggaaaaa aaaaaatagg aaaagccaga aatagcacta    6120
gaaggagcga caccagaaaa gaaggtgatg gaaccaattt agctatatat agttaactac    6180
cggctcgatc atctctgcct ccagcatagt cgaagaagaa ttttttttt cttgaggctt    6240 ctgtcagcaa ctcgtatttt ttctttctttt tttggtgagc ctaaaagtt cccacgttct    6300 cttgtacgac gccgtcacaa acaaccttat gggtaatttg tcgcggtctg ggtgtataaa    6360
tgtgtgggtg caggccggcc gtttaaacgg gccgccaccg cggtggagcc tgtgtggaag    6420
aacgattaca acaggtgttg tcctctgagg acataaaata cacaccgaga ttcatcaact    6480
cattgctgga gttagcatat ctacaattgg gtgaaatggg gagcgatttg caggcatttg    6540
ctcggcatgc cggtagaggt gtggtcaata agagcgacct catgctatac ctgagaaagc    6600
aacctgacct acaggaaaga gttactcaag aataagaatt ttcgttttaa aacctaagag    6660
tcactttaaa atttgtatac acttatttttt tttataactt atttaataat aaaaatcata    6720
aatcataaga aattcgctcg agtcgactgc agtttaaaca attctgaaag catcgaccaa    6780
aacacaacga cgtaatctga cgaaagttct ggcagaagtg acaccttcac cagttgggt    6840 ggtgatggtc atggtggtcc aaccttcacc acccaaaccc aaaccagcga tacatggacc    6900
gttcttgaca aagatggaag tgtcaatggc gttagccatt tggttcatgt tttcgatgtt    6960
tctggagtgc atggcagcag tgtggtgaca accaccttcc aatttgacag ccaaagcaat    7020
agcgtcagca acgttagcaa cacggacaac tggtaagact ggcatcatca attcagtgac    7080
agcaaatggg tgttcagcgg tggttttcgac gaataataat ctggtttctt gtggaacctt    7140
caaaccgatg gcagcagcaa tcttaccagc atctctacca acccagtctc tggagacggt    7200
acccttacct cttttcatcga tgttcttcaa caaaactggt tgcaattgtt gagcttgttc    7260
agcagtcaac ttgacggcat gttgacccttc catcaatctc atcaattcgt cagcaacgga    7320
gtcaacaaca atcaaaacct tttcgtcagc acagatgatg ttgttgtcga aagaagcacc    7380
cttgacaatg gattgagcag ctctggccaa atcagcggtt tcatcgacaa caacaggagg    7440
gttaccagca ccagcagcaa tcaatctctt gttggtgtgc tttctggcag cttcaacaac    7500
agcttcacca ccagtgacga ctaatagacc gataccctggg aacttgaata atctttgagc    7560
```

```
agtttcgata tctgggttgg caacagtgac caacaagttt tctggaccac cagcagcaac      7620
aatggcttgg ttcaatagag tgatggctct ttgagaaacc ttcttggcag ctgggtgtgg      7680
agcgaagata acggagttac cagcagcaat caaagagatg gcgttgttga tgacagtagc      7740
agctgggttg gtagatgggg tgacggaagc aacaacaccc catggagcat tttcaatcaa      7800
agtcaaacca ttatcaccgg tcaagacttg tggagacaaa cattcgacac ctggagtacc      7860
tctagcttga gcaacgttct tagcgaattt gtcttcaact ctacccatac cggtttcgga      7920
gacagccaat tcagccaagt ctctggcatg cttttcacca gcttctctga tggcagcaat      7980
ggccaattgt ctcatggcaa cagatttcaa accttgttga gcaaccttgg cagcagcaac      8040
agcgtcgtcc aaagaagcga aaacacccat tcgtggaca gcagcagatg gagtgtcaga      8100
agattgcatt tcaacaaga cagccttgac aacttgttcg atatcttgtt ggttcatttt      8160
ttactagttc tagaatccgt cgaaactaag ttctggtgtt ttaaaactaa aaaaaagact      8220
aactataaaa gtagaattta agaagtttaa gaaatagatt tacagaatta caatcaatac      8280
ctaccgtctt tatatactta ttagtcaagt aggggaataa tttcagggaa ctggtttcaa      8340 ccttttttt cagcttttc caaatcagag agagcagaag gtaatagaag gtgtaagaaa      8400
atgagataga tacatgcgtg ggtcaattgc cttgtgtcat catttactcc aggcaggttg      8460
catcactcca ttgaggttgt gcccgttttt tgcctgtttg tgccctgtt ctctgtagtt      8520 gcgctaagag aatggaccta tgaactgatg gttggtgaag aaaacaatat tttggtgctg      8580
ggattctttt tttttctgga tgccagctta aaaagcgggc tccattatat ttagtggatg      8640
ccaggaataa actgttcacc cagacaccta cgatgttata tattctgtgt aacccgcccc      8700
ctattttggg catgtacggg ttacagcaga attaaaaggc taattttttg actaaataaa      8760
gttaggaaaa tcactactat taattattta cgtattcttt gaaatggcga gtattgataa      8820
tgataaactg agctccagct tttgttccct ttagtgaggg ttaattgcgc gcttggcgta      8880
atcatggtca tagctgtttc ctgtgtgaaa ttgttatccg ctcacaattc cacacaacat      8940
aggagccgga agcataaagt gtaaagcctg gggtgcctaa tgagtgaggt aactcacatt      9000
aattgcgttg cgctcactgc ccgctttcca gtcgggaaac ctgtcgtgcc agctgcatta      9060
atgaatcggc caacgcgcgg ggagaggcgg tttgcgtatt gggcgctctt ccgcttcctc      9120
gctcactgac tcgctgcgct cggtcgttcg gctgcggcga gcggtatcag ctcactcaaa      9180
ggcggtaata cggttatcca cagaatcagg ggataacgca ggaaagaaca tgtgagcaaa      9240
aggccagcaa aaggccagga accgtaaaaa ggccgcgttg ctggcgtttt tccataggct      9300
ccgcccccct gacgagcatc acaaaaatcg acgctcaagt cagaggtggc gaaacccgac      9360
aggactataa agataccagg cgtttccccc tggaagctcc ctcgtgcgct ctcctgttcc      9420
gaccctgccg cttaccggat acctgtccgc ctttctccct tcgggaagcg tggcgctttc      9480
tcatagctca cgctgtaggt atctcagttc ggtgtaggtc gttcgctcca agctgggctg      9540
tgtgcacgaa ccccccgttc agcccgaccg ctgcgcctta tccggtaact atcgtcttga      9600
gtccaacccg gtaagacacg acttatcgcc actggcagca gccactggta acaggattag      9660
cagagcgagg tatgtaggcg gtgctacaga gttcttgaag tggtggccta actacggcta      9720
cactagaagg acagtatttg gtatctgcgc tctgctgaag ccagttacct tcggaaaaag      9780
agttggtagc tcttgatccg gcaaacaaac caccgctggt agcggtggtt tttttgtttg      9840
caagcagcag attacgcgca gaaaaaaagg atctcaagaa gatcctttga tcttttctac      9900
```

| | |
|---|---|
| ggggtctgac gctcagtgga acgaaaactc acgttaaggg attttggtca tgagattatc | 9960 |
| aaaaaggatc ttcacctaga tccttttaaa ttaaaaatga agttttaaat caatctaaag | 10020 |
| tatatatgag taaacttggt ctgacagtta ccaatgctta atcagtgagg cacctatctc | 10080 |
| agcgatctgt ctatttcgtt catccatagt tgcctgactc cccgtcgtgt agataactac | 10140 |
| gatacgggag ggcttaccat ctggccccag tgctgcaatg ataccgcgag acccacgctc | 10200 |
| accggctcca gatttatcag caataaacca gccagccgga agggccgagc gcagaagtgg | 10260 |
| tcctgcaact ttatccgcct ccatccagtc tattaattgt tgccgggaag ctagagtaag | 10320 |
| tagttcgcca gttaatagtt tgcgcaacgt tgttgccatt gctacaggca tcgtggtgtc | 10380 |
| acgctcgtcg tttggtatgg cttcattcag ctccggttcc caacgatcaa ggcgagttac | 10440 |
| atgatccccc atgttgtgca aaaagcggt tagctccttc ggtcctccga tcgttgtcag | 10500 |
| aagtaagttg gccgcagtgt tatcactcat ggttatggca gcactgcata attctcttac | 10560 |
| tgtcatgcca tccgtaagat gcttttctgt gactggtgag tactcaacca agtcattctg | 10620 |
| agaatagtgt atgcggcgac cgagttgctc ttgcccggcg tcaatacggg ataataccgc | 10680 |
| gccacatagc agaactttaa aagtgctcat cattggaaaa cgttcttcgg ggcgaaaact | 10740 |
| ctcaaggatc ttaccgctgt tgagatccag ttcgatgtaa cccactcgtg cacccaactg | 10800 |
| atcttcagca tcttttactt tcaccagcgt ttctgggtga gcaaaaacag gaaggcaaaa | 10860 |
| tgccgcaaaa aagggaataa gggcgacacg gaaatgttga atactcatac tcttcctttt | 10920 |
| tcaatattat tgaagcattt atcagggtta ttgtctcatg agcggataca tatttgaatg | 10980 |
| tatttagaaa aataaacaaa tagggggttcc gcgcacattt ccccgaaaag tgccacctga | 11040 |
| cgtctaagaa accattatta tcatgacatt aacctataaa aataggcgta tcacgaggcc | 11100 |
| ctttcgtc | 11108 |

```
<210> SEQ ID NO 47
<211> LENGTH: 11114
<212> TYPE: DNA
<213> ORGANISM: Artificial
<220> FEATURE:
<223> OTHER INFORMATION: pBOL120

<400> SEQUENCE: 47
```

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accataccac agcttttcaa ttcaattcat cattttttt ttattctttt ttttgatttc | 240 |
| ggtttctttg aaattttttt gattcggtaa tctccgaaca gaaggaagaa cgaaggaagg | 300 |
| agcacagact tagattggta tatatacgca tatgtagtgt tgaagaaaca tgaaattgcc | 360 |
| cagtattctt aacccaactg cacagaacaa aaacctgcag gaaacgaaga taaatcatgt | 420 |
| cgaaagctac atataaggaa cgtgctgcta ctcatcctag tcctgttgct gccaagctat | 480 |
| ttaatatcat gcacgaaaag caaacaaact tgtgtgcttc attggatgtt cgtaccacca | 540 |
| aggaattact ggagttagtt gaagcattag gtcccaaaat tgttttacta aaaacacatg | 600 |
| tggatatctt gactgatttt tccatggagg gcacagttaa gccgctaaag gcattatccg | 660 |
| ccaagtacaa tttttactc ttcgaagaca gaaaatttgc tgacattggt aatacagtca | 720 |
| aattgcagta ctctgcgggt gtatacgaa tagcagaatg gcagacatt acgaatgcac | 780 |
| acggtgtggt gggcccaggt attgttagcg gtttgaagca ggcggcagaa gaagtaacaa | 840 |

```
aggaacctag aggcctttttg atgttagcag aattgtcatg caagggctcc ctatctactg    900
gagaatatac taagggtact gttgacattg cgaagagcga caaagatttt gttatcggct    960
ttattgctca aagagacatg ggtggaagag atgaaggtta cgattggttg attatgacac   1020
ccggtgtggg tttagatgac aagggagacg cattgggtca acagtataga accgtggatg   1080
atgtggtctc tacaggatct gacattatta ttgttggaag aggactatttt gcaaagggaa   1140 gggatgctaa ggtagagggt gaacgttaca gaaaagcagg ctgggaagca tatttgagaa   1200
gatgcggcca gcaaaactaa aaaactgtat tataagtaaa tgcatgtata ctaaactcac   1260
aaattagagc ttcaatttaa ttatatcagt tattaccca tgcggtgtga aataccgcac   1320
agatgcgtaa ggagaaaata ccgcatcagg aaattgtaaa cgttaatatt ttgttaaaat   1380
tcgcgttaaa ttttttgttaa atcagctcat ttttttaacca ataggccgaa atcggcaaaa   1440
tcccttataa atcaaaagaa tagaccgaga tagggttgag tgttgttcca gtttggaaca   1500
agagtccact attaaagaac gtggactcca acgtcaaagg cgaaaaaacc gtctatcagg   1560
gcgatggccc actacgtgaa ccatcaccct aatcaagttt tttggggtcg aggtgccgta   1620
aagcactaaa tcggaaccct aaagggagcc cccgatttag agcttgacgg ggaaagccgg   1680
cgaacgtggc gagaaaggaa gggaagaaag cgaaaggagc gggcgctagg gcgctggcaa   1740
gtgtagcggt cacgctgcgc gtaaccacca cacccgccgc gcttaatgcg ccgctacagg   1800
gcgcgtcgcg ccattcgcca ttcaggctgc gcaactgttg ggaagggcga tcggtgcggg   1860
cctcttcgct attacgccag ctggcgaaag ggggatgtgc tgcaaggcga ttaagttggg   1920
taacgccagg gttttcccag tcacgacgtt gtaaaacgac ggccagtgag cgcgcgtaat   1980
acgactcact atagggcgaa ttgggtaccg ggcccccccct cgaggtcgac ggtatcgata   2040
agcttgatat cgaattcctg cagcccgggg gatccactag ttctagagcg gcccattttaa   2100 acggccggcc ctagatcaga gggtggtaaa tgaagtgtaa tagtattcat ttttcttata   2160
aatcatccct tccgtgattt atacaaaaga agaggagaat atgctgaata cttggtatat   2220
tactctacat tatactctta tcttgacggg tattctgagc atcttactca gtttcaagat   2280
cttttaatgt ccaaaaacat ttgagccgat ctaaatactt ctgtgttttc attaatttat   2340
aaattgtact cttttaagac atggaaagta ccaacatcgg ttgaaacagt ttttcattta   2400
cttatggttt attggttttt ccagtgaatg attatttgtc gttacccttt cgtaaaagtt   2460
caaacacgtt tttaagtatt gtttagttgc tctttcgaca tatatgatta tccctgcgcg   2520
gctaaagtta aggatgcaaa aaacataaga caactgaagt taatttacgt caattaagtt   2580
ttccagggta atgatgtttt gggcttccac taattcaata agtatgtcat gaaatacgtt   2640
gtgaagagca tccagaaaata atgaaaagaa caacgaaac tgggtcggcc tgttgtttct   2700
tttctttacc acgtgatctg cggcatttac aggaagtcgc gcgttttgcg cagttgttgc   2760
aacgcagcta cggctaacaa agccagtggg aactcgactg atgtgttagg gcctaaaact   2820
ggtggtgaca gctgaagtga actattcaat ccaatcatgt catggctgtc acaaagacct   2880
tgcggaccgc acgtacgaac acatacgtat gctaatatgt gttttgatag tacccagtga   2940
tcgcagacct gcaatttttt tgtaggtttg gaagaatata taaaggttgc actcattcaa   3000
gatagttttt ttcttgtgtg tctattcatt ttattattgt ttgtttaaat gttaaaaaaa   3060
ccaagaactt agtttcaaat taaattcatc acacaaacaa acaaaacaaa atgaacattg   3120
ttgtttgttt gaagcaagtt ccagacactg ctgaagtcag aattgaccca gtcaagggta   3180
```

```
ctttaatcag agaaggtgtt ccatctatca tcaacccaga cgacaagaac gctttggaag      3240
aagctttggt tttgaaggac aactacggtg ctcacgttac cgtcatttcc atgggtccac      3300
ctcaagccaa gaacgctttg gttgaagctt tggccatggg tgctgatgaa gctgtcttat      3360
tgactgacag agctttcggt ggtgctgata ctttagctac ctctcacacc attgctgctg      3420
gtatcaagaa attgaaatac gatatcgtct ttgccggtcg tcaagccatc gatggtgata      3480
ccgctcaagt cggtccagaa attgctgaac atttgggtat tccacaagtc acctacgttg      3540
aaaaggttga agttgacggt gacactttga agatcagaaa ggcttgggaa gacggttacg      3600
aagttgttga agtcaagact ccagttctat tgactgccat caaggaattg aacgttccaa      3660
gatacatgtc cgttgaaaag atcttcggtg ctttcgacaa ggaagtcaag atgtggactg      3720
ctgatgatat cgatgtcgac aaggccaact tgggtttgaa aggttctcca accaaggtca      3780
agaaatcttc taccaaggaa gtcaagggtc aaggtgaagt cattgacaaa ccagtcaagg      3840
aagctgccgc ttacgttgtt tccaagttga aggaagaaca ctacatctaa agcccgggcg      3900
gagattgata agacttttct agttgcatat ctttttatatt taaatcttat ctattagtta      3960
atttttgta atttatcctt atatatagtc tggttattct aaaatatcat ttcagtatct      4020
aaaaattccc ctcttttttc agttatatct taacaggcga cagtccaaat gttgatttat      4080
cccagtccga ttcatcaggg ttgtgaagca ttttgtcaat ggtcgaaatc acatcagtaa      4140
tagtgcctct tacttgcctc atagaatttc tttctcttaa cgtcaccgtt tggtctttta      4200
tagtttcgaa atctatggtg ataccaaatg gtgttcccaa ttcatcgtta cgggcgtatt      4260
ttttaccaat tgaagtattg gaatcgtcaa ttttaaagta tatctctctt ttacgtaaag      4320
cctgcgagat cctcttaagt atagcgggga agccatcgtt attcgatatt gtcgtaacaa      4380
atactttgat cggcgctatg tttaaatgtt taaacatgga cagatatgcg atgaaaacgc      4440
taagtgatac tccaaatggt gaaaggtacg atgcttggaa acaatacttg gaaatcaccg      4500
gaaacaccat atgcggcgaa aagccaatta gtgtgatact aagtgcttta tcgaaaatcc      4560
gtgatgccgg tccttcaggc atcaaatttc agtggcctaa ttattcacag agttctcatg      4620
tgacaagtat tgatgatagt agtgtcagtt atgcttcagg ttatgttact ataggataat      4680
gatcacggct aaaacggtcg aatgtaagca tatatctttc gattgtataa ttgttcccaa      4740
atactacagc atctcaagga aaaaaaaaca aaaacttcca aaaaaatcga atccctgagg      4800
aatctttaat acattttcaa tctatttaag ttttataaac gtgtatatga gatgtcatga      4860
gcatgaatta ttaataataa aaactaaatc attaaagtaa cttaaggagt taaagcccgg      4920
gctttaattg ttagcagcct tgacttgagc aatcaattct ggaacaacct tgttgacatc      4980
accgacaatg ccaaatcag caaccttcat gattggagct tcgacatctt tgttgatggc      5040
aatgatgtag tcagagtctt gcataccagc caagtgttgg atggcaccag agataccaca      5100
agcaatgtac aaagttggtc tgacggtctt accggtttga ccgacttgca agtccttgtc      5160
aacccattcc ttttcaatgg cagctctgga agcagcaatg gtaccaccca caaagaagc       5220
taattcttcc aatttttcga gttttccttt ggaaccaaca ccacgaccac cagcaaccaa      5280
aaccttggct tcaccgatat cagcaatgtc cttggccaat tgacaacct tggaaaacctt      5340
ggttctgata tcagaagcag tcaatttgat ggcaaccttt tcgatcttgt catcagaaac      5400
gttagcatcg ttaactggca attttttcaaa gacacctggt ctgacggtgg ccatttgagg      5460
tctgtggtca gaacagacaa tggtagcaat caagttacca ccgaaagctg gtctggtagc      5520
caacaagtca cggttttcga catcgatatc caaagaggta cagtcagcag tcaaaccagt      5580
```

```
agacaatctg gcagcaattc ttggacccaa gtctctaccg atgaaagtag caccgatgaa    5640
taagatttct ggctttcttt cgttgaccaa gtcacagata accttggcgt aaccgtcagt    5700
ggagaaatga gctaataatt cgttgtcagc agccaaaacc ttgtcagcac cgtgggacaa    5760
caagtccttg gacatctttt cagtgttgtg acccaataag acagcagtca attcaacacc    5820 caattttca gccatttcct taccccttacc tagcaattcc aaagaaacct tttgtaattc    5880
accatctctt tgttcagcga aaacccagac acccttgtag tcagccttgt tcatgtttag    5940
ttaattatag ttcgttgacc gtatattcta aaaacaagta ctccttaaaa aaaaaccttg    6000
aagggaataa acaagtagaa tagatagaga gaaaaataga aatgcaaga gaatttatat    6060 attagaaaga gagaaagaaa aatggaaaaa aaaaaatagg aaaagccaga aatagcacta    6120
gaaggagcga caccgaaaaa gaaggtgatg gaaccaattt agctatatat agttaactac    6180
cggctcgatc atctctgcct ccagcatagt cgaagaagaa ttttttttttt cttgaggctt    6240 ctgtcagcaa ctcgtatttt ttctttcttt tttggtgagc ctaaaaagtt cccacgttct    6300
cttgtacgac gccgtcacaa acaaccttat gggtaatttg tcgcggtctg ggtgtataaa    6360
tgtgtgggtg caggccggcc gtttaaacgg gccgccaccg cggtggagcc tgtgtggaag    6420
aacgattaca acaggtgttg tcctctgagg acataaaata cacaccgaga ttcatcaact    6480
cattgctgga gttagcatat ctacaattgg gtgaaatggg gagcgatttg caggcatttg    6540
ctcggcatgc cggtagaggt gtggtcaata agagcgacct catgctatac ctgagaaagc    6600
aacctgacct acaggaaaga gttactcaag aataagaatt ttcgttttaa aacctaagag    6660
tcactttaaa atttgtatac acttattttt tttataactt atttaataat aaaaatcata    6720
aatcataaga aattcgctcg agtcgactgc agtttatcta atggagaaac catcagtcaa    6780
gacacatctt cttcttctag cgaagtgacg ggcagtggta gtaccttcac cagttggagt    6840
agcaatggtg aaagtggtgg aaccttcacc tctgaaacct aaaccagcga agatggacc    6900 gttcttgaca aagatggagg tttgcatgtc acgggcagcc ttgttcaatc tggagatgtt    6960
ttgagagtgc atggtagcag tgtgatgtag accttgttcc aattcaatgg caacttccaa    7020
agcttcatcg aagtctggaa ctctgacaac tggaacaatt ggcatcaaca attcaacagt    7080
agcgaatggg tgggactttt cagtttcgac aatgatcaat cttggggtga atcacaagc    7140 aataccagct tctttcaaga tttcagtggc agacttacca accaatttct tgttggtgac    7200
acccttgtca gtgacggcaa cctttttccaa ttttttggata tcagatgggt tagtgacgtg    7260
caaagcaccg ttcttttcca tttgaacaa caagaagtca gcaatggagt caacggcaac    7320
aacagacttt tcagcgatac acaagatatt atggtcaaag gaagcaccgt cgacaatgtc    7380
agcagcagcc ttttcaatgt tagcggtttc gtcaacgatg gatggagggt taccagcacc    7440
agcaccgata accttcttac cagattgcat agcttgcaag acaacacctg gaccaccagt    7500
gatgaccaac aatggaacct tgggtggtt catcattct tgagcagctt ggatagatgg    7560
cttggcaacg gtgacaatca agttgtcaat accacaagaa tctctgacga tagtgttcaa    7620
cttttcaatc aaccataaag agatgttctt ggcacctggg tgaggagagt agaaaacggc    7680
gttaccagca gccaacatac cgatggagtt acagatcaaa gtttcagttg ggttggtaga    7740
tggagcaaca gcaccgatga caccgtatgg agataattcg tataaagtca taccgttgtc    7800
accggtagca acttcagtgt acaagtcttc aacacctgga gtcttttcga tagctaaagt    7860
gttcttcaag atttttatcgg tgacattacc cataccggtt tcagcaacag ctctggtagc    7920
```

```
aatggtttcg atttctgggt ataaagcttc tctgatggcc ttgacaacgt ttcttctttc    7980
ttccaaagat ttttccttgt aacagttttg agcaatgacg gcagcttgga cagcttcatc    8040
gacggtatcg aaaacaccgg acttggcacc ttgggtggtg gtcttggttg gaacttcctt    8100
ttgttcagcc aattttttcca acaaaacctt cttgactaat tgttccaatt ccaaagattc   8160
cattttttac tagttctaga atccgtcgaa actaagttct ggtgttttaa aactaaaaaa   8220
aagactaact ataaaagtag aatttaagaa gtttaagaaa tagatttaca gaattacaat   8280
caatacctac cgtctttata tacttattag tcaagtaggg gaataatttc agggaactgg   8340
tttcaacctt ttttttcagc ttttttccaaa tcagagagag cagaaggtaa tagaaggtgt   8400
aagaaaatga gatagataca tgcgtgggtc aattgccttg tgtcatcatt tactccaggc   8460
aggttgcatc actccattga ggttgtgccc gttttttgcc tgtttgtgcc cctgttctct   8520
gtagttgcgc taagagaatg gacctatgaa ctgatggttg gtgaagaaaa caatattttg   8580
gtgctgggat tcttttttttt tctggatgcc agcttaaaaa gcgggctcca ttatatttag   8640
tggatgccag gaataaactg ttcacccaga cacctacgat gttatatatt ctgtgtaacc   8700
cgcccctat tttgggcatg tacgggttac agcagaatta aaaggctaat ttttgactaa   8760
aataagtta ggaaaatcac tactattaat tatttacgta ttctttgaaa tggcgagtat   8820
tgataatgat aaactgagct ccagcttttg ttcccttttag tgagggttaa ttgcgcgctt   8880
ggcgtaatca tggtcatagc tgtttcctgt gtgaaattgt tatccgctca caattccaca   8940
caacatagga gccggaagca taaagtgtaa agcctggggt gcctaatgag tgaggtaact   9000
cacattaatt gcgttgcgct cactgcccgc tttccagtcg ggaaacctgt cgtgccagct   9060
gcattaatga atcggccaac gcgcggggag aggcggtttg cgtattgggc gctcttccgc   9120
ttcctcgctc actgactcgc tgcgctcggt cgttcggctg cggcgagcgg tatcagctca   9180
ctcaaaggcg gtaatacggt tatccacaga atcagggat aacgcaggaa agaacatgtg   9240
agcaaaaggc cagcaaaagg ccaggaaccg taaaaaggcc gcgttgctgg cgtttttcca   9300
taggctccgc ccccctgacg agcatcacaa aaatcgacgc tcaagtcaga ggtggcgaaa   9360
cccgacagga ctataaagat accaggcgtt tccccctgga agctccctcg tgcgctctcc   9420
tgttccgacc ctgccgctta ccggatacct gtccgccttt ctcccttcgg gaagcgtggc   9480
gctttctcat agctcacgct gtaggtatct cagttcggtg taggtcgttc gctccaagct   9540
gggctgtgtg cacgaacccc ccgttcagcc cgaccgctgc gccttatccg gtaactatcg   9600
tcttgagtcc aacccggtaa gacacgactt atcgccactg gcagcagcca ctggtaacag   9660
gattagcaga gcgaggtatg taggcggtgc tacagagttc ttgaagtggt ggcctaacta   9720
cggctacact agaaggacag tatttggtat ctgcgctctg ctgaagccag ttaccttcgg   9780
aaaaagagtt ggtagctctt gatccggcaa acaaaccacc gctggtagcg gtggtttttt   9840
tgtttgcaag cagcagatta cgcgcagaaa aaaaggatct caagaagatc ctttgatctt   9900
ttctacgggg tctgacgctc agtggaacga aaactcacgt taagggattt tggtcatgag   9960
attatcaaaa aggatcttca cctagatcct tttaaattaa aaatgaagtt ttaaatcaat  10020
ctaaagtata tatgagtaaa cttggtctga cagttaccaa tgcttaatca gtgaggcacc  10080
tatctcagcg atctgtctat ttcgttcatc catagttgcc tgactccccg tcgtgtagat  10140
aactacgata cgggagggct taccatctgg ccccagtgct gcaatgatac cgcgagaccc  10200
acgctcaccg gctccagatt tatcagcaat aaaccagcca gccggaaggg ccgagcgcag  10260
aagtggtcct gcaactttat ccgcctccat ccagtctatt aattgttgcc gggaagctag  10320
```

```
agtaagtagt tcgccagtta atagtttgcg caacgttgtt gccattgcta caggcatcgt    10380
ggtgtcacgc tcgtcgtttg gtatggcttc attcagctcc ggttcccaac gatcaaggcg    10440
agttacatga tcccccatgt tgtgcaaaaa agcggttagc tccttcggtc ctccgatcgt    10500
tgtcagaagt aagttggccg cagtgttatc actcatggtt atggcagcac tgcataattc    10560
tcttactgtc atgccatccg taagatgctt ttctgtgact ggtgagtact caaccaagtc    10620
attctgagaa tagtgtatgc ggcgaccgag ttgctcttgc ccggcgtcaa tacgggataa    10680
taccgcgcca catagcagaa ctttaaaagt gctcatcatt ggaaaacgtt cttcggggcg    10740
aaaactctca aggatcttac cgctgttgag atccagttcg atgtaaccca ctcgtgcacc    10800
caactgatct tcagcatctt ttactttcac cagcgtttct gggtgagcaa aaacaggaag    10860
gcaaaatgcc gcaaaaaagg gaataagggc gacacggaaa tgttgaatac tcatactctt    10920 ccttttcaa tattattgaa gcatttatca gggttattgt ctcatgagcg gatacatatt    10980
tgaatgtatt tagaaaaata aacaaatagg ggttccgcgc acatttcccc gaaaagtgcc    11040
acctgacgtc taagaaacca ttattatcat gacattaacc tataaaaata ggcgtatcac    11100
gaggcccttt cgtc                                                      11114

<210> SEQ ID NO 48
<211> LENGTH: 2613
<212> TYPE: DNA
<213> ORGANISM: Entamoeba histolytica

<400> SEQUENCE: 48
atgtcaacac aacaaactat gactgtagat gaacatatta atcaacttgt tgctaaagca      60
caagttgcac ttaaagaata tcttaaacca gaatatacac aagaaaaaat agattatatt     120
gtaaagaaag catcagttgc agcacttgat caacattgtg cacttgcagc agctgcagtt     180
gaagaaacag gaagaggtat ttttgaagat aaagctacta aaaatatatt tgcatgtgaa     240
catgttacac atgaaatgag acatgctaaa acagttggta ttattaatgt agatccactt     300
tatggaatta cagaaattgc agaaccagtt ggagttgttt gtggagttac accagttact     360
aatccaacat caacagctat tttcaagtca cttatttcaa ttaaaacaag aaatccaatt     420
gtattttcat tccatccatc agcacttaaa tgttctatta tggcagctaa aattgttaga     480
gatgcagcta ttgcagcagg agcaccagaa aattgtattc aatggattga atttggagga     540
attgaagcat caaataaatt aatgaatcat ccaggagttg ctactattct gctacagga     600 ggaaatgcta tggttaaagc agcatattca tcaggaaaac cagcacttgg agtaggagca     660
ggaaatgtac caacatatat tgaaaaaaca tgtaatatta acaagcagc aaatgatgta     720 gttatgtcaa atcatttga taatggtatg atttgtgcat cagaacaagc agcaattatt     780
gataaagaaa tttatgatca agtagttgaa gaaatgaaaa cacttggagc atatttcatt     840
aatgaagaag aaaagctaa attagaaaag tttatgtttg gagttaatgc atattcagca     900
gatgttaata atgcaagact taatccaaaa tgtccaggta tgtcaccaca atggtttgct     960
gaacaagttg gaattaaagt tccagaagat tgtaatatta tttgtgcagt ttgtaaagaa    1020
gttggaccaa atgaaccatt aacaagagaa aaattatcac cagttcttgc tattcttaaa    1080
gcagaaaata cacaagatgg tattgataaa gctgaagcta tggttgaatt taatggtaga    1140
ggacattcag cagctattca ttcgaatgat aaagcagtag ttgaaaagta tgcacttaca    1200
atgaaagcat gcagaatttt acataataca ccatcatcac aaggaggaat tggatcaatt    1260
```

```
tataactata tttggccatc atttacactt ggatgtggat catatggagg aaattcggta    1320
tcagctaatg ttacatatca taatttatta aatattaaaa gacttgcaga tagaagaaac    1380
aaccttcaat ggttcagagt tccaccaaag attttctttg aaccacattc tattagatat    1440
cttgctgaac ttaaggaact tagtaaaata ttcattgttt cagatagaat gatgtataaa    1500
ttaggatatg tagatagagt tatggatgta ttgaaaagaa gaagtaatga agtagaaatt    1560
gaaattttca ttgatgtaga accagatcca tctattcaaa ccgttcaaaa aggacttgct    1620
gttatgaata catttggacc agataatatt attgctattg gaggaggatc agctatggat    1680
gcagctaaga ttatgtggtt actttatgaa catccagaag ccgatttctt tgcaatgaaa    1740
caaaaattca ttgatcttag aaagagagca tttaaattcc aacaatggg taagaaagct     1800 agattaattt gtattccaac aacatcagga actggatcag aagttacacc atttgcagtt    1860
atttcagatc atgaaacagg taagaaatat ccacttgctg attattcact tacaccatca    1920
gttgctattg ttgatccaat gtttactatg tcacttccaa agagagctat tgctgatact    1980
ggacttgatg tattggttca tgcaacagaa gcatatgttt cagttatggc taatgaatat    2040
actgatggac ttgctagaga agcagttaaa ttagtctttg aaaatcttct taaatcatat    2100
aatggagatt tagaagcaag agaaaagatg cacaatgctg caacaattgc aggtatggca    2160
tttgcatcag cattccttgg tatgaccat tccatggcac ataaagttgg agcagcattc      2220
catcttccac atggtagatg tgtagcagta ttattaccac atgtcattag atataatgga    2280
caaaaaccaa gaaagcttgc aatgtggcca aaatataatt tctataaggc agaccaaaga    2340
tatatggaac ttgcacaaat ggttggactt aaatgtaata caccagctga aggagttgaa    2400
gcatttgcta agcatgtga agaattaatg aaagccacag agactattac tggattcaag      2460
caagcaaata ttgatgaagc agcatggatg agtaaagtac cagaaatggc acttcttgca    2520
tttgaagatc aatgttcacc agctaatcca agagtcccaa tggttaagga tatggaaaag    2580
attctcaaag ctgcatatta tccaattgct tga                                 2613

<210> SEQ ID NO 49
<211> LENGTH: 2610
<212> TYPE: DNA
<213> ORGANISM: Artificial sequence
<220> FEATURE:
<223> OTHER INFORMATION: adh2 E. histolytica codon pair optimised

<400> SEQUENCE: 49
atgtccactc aacaaaccat gaccgttgat gaacacatta ccaattggt cagaaaggct       60 caagttgctt tgaaggaata cttgaaacca gaatacactc aagaaaagat cgattacatt     120
gtcaagaagg cttctgttgc tgctctagac aacactgtg ctttggctgc tgctgctgtc      180
gaagaaactg gtcgtggtat ctttgaagac aaagctacca gaacattttt cgcttgtgaa    240
cacgtcactc acgaaatgag acacgccaag accgttggta tcatcaacgt tgatccatta    300
tacggtatca ctgaaattgc tgaaccagtc ggtgttgtct gtggtgtcac cccagttacc    360
aacccaactt ctactgccat tttcaaatct ttgatttcca tcaagaccag aaacccaatt    420 gtttttctcct tccacccatc tgctttgaaa tgttccatca tggctgccaa gatcgtcaga    480
gatgctgcca ttgctgctgg tgctccagaa aactgtatcc aatggatcga atttggtggt    540
attgaagctt ccaacaaatt gatgaaccat cctggtgttg ctaccatctt agctactggt    600
ggtaacgcta tggtcaaggc tgcttactct tctggtaagc agcttttggg tgtcggtgct    660
ggtaacgtcc caacttacat cgaaaagacc tgtaatatca agcaagctgc taacgatgtt    720
```

```
gtcatgtcca agtctttcga caacggtatg atctgtgcct ccgaacaagc tgccatcatc    780
gacaaagaaa tctacgacca agttgttgaa gaaatgaaga ctttgggtgc ttacttcatc    840
aacgaagaag aaaaggccaa attggaaaaa ttcatgttcg gtgttaatgc ttactctgct    900
gatgtcaaca acgccagatt gaacccaaag tgtccaggta tgtctccaca atggttcgct    960
gaacaagtcg gtatcaaggt tccagaagac tgtaacatca tctgtgccgt tgtaaggaa    1020 gttggtccaa acgaaccatt gaccagagaa aagttgtctc cagttttggc catttgaag    1080 gctgaaaaca ctcaagatgg tattgacaag gctgaagcta tggtcgaatt caacggtcgt    1140
ggtcactctg ctgccattca ctccaatgac aaggctgttg ttgaaaaata cgctttgacc    1200
atgaaggctt gtcgtatctt gcacaacact ccatcttctc aaggtggtat cggttccatt    1260
tacaactaca tctggccatc tttcacttta ggttgtggtt cttacggtgg taactccgtt    1320
tctgccaatg ttacctacca caacttgttg aacatcaaga gattggctga cagaagaaac    1380
aacttacaat ggttcagagt cccaccaaag atcttcttcg aacctcactc cattagatac    1440
ttggctgaat tgaaggaatt gtccaagatt ttcattgtct ctgacagaat gatgtacaaa    1500
ttgggttacg ttgacagagt tatggatgtc ttgaagagaa gatccaacga agttgaaatt    1560
gaaatcttca tcgatgttga accagaccca tccattcaaa ccgtccaaaa gggtttggct    1620
gtcatgaaca ctttcggtcc agacaacatc attgccattg gtggtggttc tgccatggat    1680
gctgccaaga tcatgtggtt attatacgaa catccagaag ctgatttctt cgctatgaag    1740
caaaaattca tcgatttaag aaagagagct ttcaagttcc caaccatggg taagaaggcc    1800
agattaatct gtatcccaac cacttctggt accggttctg aagtcacccc attcgctgtc    1860
atctctgacc acgaaactgg taagaagtat ccattggctg actactcttt gaccccatcc    1920
gttgccattg ttgacccaat gtttaccatg tccttgccta agagagccat tgctgacact    1980
ggtttggatg tcttagtcca cgctactgaa gcttacgttt ctgttatggc taacgaatac    2040
actgacggtt tggccagaga agctgtcaaa ttggttttcg aaaacttgtt gaaatcttac    2100
aacggtgact tggaagctcg tgaaaagatg cacaacgctg ctaccattgc tggtatggcc    2160
tttgcttctg ctttcttggg tatggaccat tccatggctc acaaggtcgg tgctgctttc    2220
catttgccac acggtagatg tgttgccgtt tgttgcctc acgttatcag atacaacggt    2280
caaaagccaa gaaagttggc catgtggcca agtacaact tctacaaggc tgatcaaaga    2340
tacatggaat tggctcaaat ggtcggtttg aagtgtaaca ccccagctga aggtgtcgaa    2400
gcctttgcca aggcttgtga agaattgatg aaggctacta aaccatcac tggtttcaag    2460 aaggccaaca ttgatgaagc tgcttggatg tccaaggttc cagaaatggc tctattggct    2520
ttcgaagacc aatgttctcc agctaaccca agagtcccaa tggttaagga catggaaaag    2580
attttgaagg ctgcttacta cccaatcgct                                    2610
```

<210> SEQ ID NO 50
<211> LENGTH: 870
<212> TYPE: PRT
<213> ORGANISM: Entamoeba histolytcia

<400> SEQUENCE: 50

Met Ser Thr Gln Gln Thr Met Thr Val Asp Glu His Ile Asn Gln Leu
1               5                   10                  15

Val Arg Lys Ala Gln Val Ala Leu Lys Glu Tyr Leu Lys Pro Glu Tyr
            20                  25                  30

-continued

```
Thr Gln Glu Lys Ile Asp Tyr Ile Val Lys Lys Ala Ser Val Ala Ala
             35                  40                  45

Leu Asp Gln His Cys Ala Leu Ala Ala Ala Val Glu Glu Thr Gly
 50                  55                  60

Arg Gly Ile Phe Glu Asp Lys Ala Thr Lys Asn Ile Phe Ala Cys Glu
 65                  70                  75                  80

His Val Thr His Glu Met Arg His Ala Lys Thr Val Gly Ile Ile Asn
             85                  90                  95

Val Asp Pro Leu Tyr Gly Ile Thr Glu Ile Ala Glu Pro Val Gly Val
            100                 105                 110

Val Cys Gly Val Thr Pro Val Thr Asn Pro Thr Ser Thr Ala Ile Phe
            115                 120                 125

Lys Ser Leu Ile Ser Ile Lys Thr Arg Asn Pro Ile Val Phe Ser Phe
130                 135                 140

His Pro Ser Ala Leu Lys Cys Ser Ile Met Ala Ala Lys Ile Val Arg
145                 150                 155                 160

Asp Ala Ala Ile Ala Gly Ala Pro Glu Asn Cys Ile Gln Trp Ile
                165                 170                 175

Glu Phe Gly Gly Ile Glu Ala Ser Asn Lys Leu Met Asn His Pro Gly
            180                 185                 190

Val Ala Thr Ile Leu Ala Thr Gly Gly Asn Ala Met Val Lys Ala Ala
            195                 200                 205

Tyr Ser Ser Gly Lys Pro Ala Leu Gly Val Gly Ala Gly Asn Val Pro
            210                 215                 220

Thr Tyr Ile Glu Lys Thr Cys Asn Ile Lys Gln Ala Ala Asn Asp Val
225                 230                 235                 240

Val Met Ser Lys Ser Phe Asp Asn Gly Met Ile Cys Ala Ser Glu Gln
                245                 250                 255

Ala Ala Ile Ile Asp Lys Glu Ile Tyr Asp Gln Val Val Glu Glu Met
                260                 265                 270

Lys Thr Leu Gly Ala Tyr Phe Ile Asn Glu Glu Lys Ala Lys Leu
            275                 280                 285

Glu Lys Phe Met Phe Gly Val Asn Ala Tyr Ser Ala Asp Val Asn Asn
290                 295                 300

Ala Arg Leu Asn Pro Lys Cys Pro Gly Met Ser Pro Gln Trp Phe Ala
305                 310                 315                 320

Glu Gln Val Gly Ile Lys Val Pro Glu Asp Cys Asn Ile Ile Cys Ala
                325                 330                 335

Val Cys Lys Glu Val Gly Pro Asn Glu Pro Leu Thr Arg Glu Lys Leu
            340                 345                 350

Ser Pro Val Leu Ala Ile Leu Lys Ala Glu Asn Thr Gln Asp Gly Ile
            355                 360                 365

Asp Lys Ala Glu Ala Met Val Glu Phe Asn Gly Arg Gly His Ser Ala
370                 375                 380

Ala Ile His Ser Asn Asp Lys Ala Val Val Glu Lys Tyr Ala Leu Thr
385                 390                 395                 400

Met Lys Ala Cys Arg Ile Leu His Asn Thr Pro Ser Ser Gln Gly Gly
                405                 410                 415

Ile Gly Ser Ile Tyr Asn Tyr Ile Trp Pro Ser Phe Thr Leu Gly Cys
            420                 425                 430

Gly Ser Tyr Gly Gly Asn Ser Val Ser Ala Asn Val Thr Tyr His Asn
            435                 440                 445

Leu Leu Asn Ile Lys Arg Leu Ala Asp Arg Arg Asn Asn Leu Gln Trp
```

```
            450                 455                 460
Phe Arg Val Pro Pro Lys Ile Phe Phe Glu Pro His Ser Ile Arg Tyr
465                 470                 475                 480

Leu Ala Glu Leu Lys Glu Leu Ser Lys Ile Phe Ile Val Ser Asp Arg
                485                 490                 495

Met Met Tyr Lys Leu Gly Tyr Val Asp Arg Val Met Asp Val Leu Lys
                500                 505                 510

Arg Arg Ser Asn Glu Val Glu Ile Glu Ile Phe Ile Asp Val Glu Pro
            515                 520                 525

Asp Pro Ser Ile Gln Thr Val Gln Lys Gly Leu Ala Val Met Asn Thr
            530                 535                 540

Phe Gly Pro Asp Asn Ile Ile Ala Ile Gly Gly Ser Ala Met Asp
545                 550                 555                 560

Ala Ala Lys Ile Met Trp Leu Leu Tyr Glu His Pro Glu Ala Asp Phe
                565                 570                 575

Phe Ala Met Lys Gln Lys Phe Ile Asp Leu Arg Lys Arg Ala Phe Lys
                580                 585                 590

Phe Pro Thr Met Gly Lys Lys Ala Arg Leu Ile Cys Ile Pro Thr Thr
            595                 600                 605

Ser Gly Thr Gly Ser Glu Val Thr Pro Phe Ala Val Ile Ser Asp His
            610                 615                 620

Glu Thr Gly Lys Lys Tyr Pro Leu Ala Asp Tyr Ser Leu Thr Pro Ser
625                 630                 635                 640

Val Ala Ile Val Asp Pro Met Phe Thr Met Ser Leu Pro Lys Arg Ala
                645                 650                 655

Ile Ala Asp Thr Gly Leu Asp Val Leu Val His Ala Thr Glu Ala Tyr
                660                 665                 670

Val Ser Val Met Ala Asn Glu Tyr Thr Asp Gly Leu Ala Arg Glu Ala
            675                 680                 685

Val Lys Leu Val Phe Glu Asn Leu Leu Lys Ser Tyr Asn Gly Asp Leu
            690                 695                 700

Glu Ala Arg Glu Lys Met His Asn Ala Ala Thr Ile Ala Gly Met Ala
705                 710                 715                 720

Phe Ala Ser Ala Phe Leu Gly Met Asp His Ser Met Ala His Lys Val
                725                 730                 735

Gly Ala Ala Phe His Leu Pro His Gly Arg Cys Val Ala Val Leu Leu
                740                 745                 750

Pro His Val Ile Arg Tyr Asn Gly Gln Lys Pro Arg Lys Leu Ala Met
            755                 760                 765

Trp Pro Lys Tyr Asn Phe Tyr Lys Ala Asp Gln Arg Tyr Met Glu Leu
            770                 775                 780

Ala Gln Met Val Gly Leu Lys Cys Asn Thr Pro Ala Glu Gly Val Glu
785                 790                 795                 800

Ala Phe Ala Lys Ala Cys Glu Glu Leu Met Lys Ala Thr Glu Thr Ile
                805                 810                 815

Thr Gly Phe Lys Lys Ala Asn Ile Asp Glu Ala Ala Trp Met Ser Lys
                820                 825                 830

Val Pro Glu Met Ala Leu Leu Ala Phe Glu Asp Gln Cys Ser Pro Ala
            835                 840                 845

Asn Pro Arg Val Pro Met Val Lys Asp Met Glu Lys Ile Leu Lys Ala
            850                 855                 860

Ala Tyr Tyr Pro Ile Ala
865                 870
```

<210> SEQ ID NO 51
<211> LENGTH: 2658
<212> TYPE: DNA
<213> ORGANISM: Piromyces sp. E2

<400> SEQUENCE: 51

| | | | | | |
|---|---|---|---|---|---|
| atgtccggat | tacaaatgtt | ccaaaacctt | tctctttacg | gtagtctcgc | cgaaatcgat | 60 |
| actagcgaaa | agcttaacga | agctatggac | aaattaactg | ctgcccaaga | acaattcaga | 120 |
| gaatacaacc | aagaacaagt | tgacaaaatc | ttcaaggctg | ttgctttagc | tgcttctcaa | 180 |
| aaccgtgttg | ctttcgctaa | gtacgcacac | gaagaaaccc | aaaagggtgt | tttcgaagat | 240 |
| aaggttatca | agaacgaatt | cgctgctgat | tacatttacc | acaagtactg | caatgacaag | 300 |
| accgccggta | tcattgaata | tgatgaagcc | aatggtctta | tggaaattgc | tgaaccagtt | 360 |
| ggtccagttg | ttggtattgc | tccagttact | aacccaactt | ctactatcat | ctacaagtct | 420 |
| ttaattgcct | aaagacccg | taactgtatt | atcttctcac | cacatccagg | agctcacaag | 480 |
| gcctctgttt | tcgttgttaa | ggtcttacac | caagctgctg | ttaaggctgg | tgccccagaa | 540 |
| aactgtattc | aaatcatctt | cccaagatg | gatttaacta | ctgaattatt | acaccaccaa | 600 |
| aagactcgtt | tcatttgggc | tactggtggt | ccaggtttag | ttcacgcctc | ttacacttct | 660 |
| ggtaagccag | ctcttggtgg | tggtccaggt | aatgctccag | ctcttattga | tgaaacttgt | 720 |
| gatatgaacg | aagctgttgg | ttctatcgtt | gtttctaaga | cttccgattg | tggtatgatc | 780 |
| tgtgccactg | aaaacgctgt | tgtcgttgtc | gaatctgtct | acgaaaactt | cgttgctacc | 840 |
| atgaagaagc | gtggtgccta | cttcatgact | ccagaagaaa | ccaagaaggc | ttctaacctt | 900 |
| cttttcggag | aaggtatgag | attaaatgct | aaggctgttg | gtcaaactgc | caagactta | 960 |
| gctgaaatgg | ccggtttcga | agtcccagaa | acaccgttg | ttctctgtgg | tgaagcttct | 1020 |
| gaagttaaat | tcgaagaacc | aatggctcac | gaaaagttaa | ctactatcct | cggtatctac | 1080 |
| aaggctaagg | actttgacga | tggtgtcaga | ttatgtaagg | aattagttac | tttcggtggt | 1140 |
| aagggtcaca | ctgctgttct | ctacaccaac | caaaacaaca | aggaccgtat | tgaaaagtac | 1200 |
| caaaacgaag | ttccagcctt | ccacatctta | gttgacatgc | catcttccct | cggttgtatt | 1260 |
| ggtgatatgt | acaacttccg | tcttgctcca | gctcttacca | ttacttgtgg | tactatgggt | 1320 |
| ggtggttcct | cctctgataa | cattggtcca | agcacttac | ttaacatcaa | gcgtgttggt | 1380 |
| atgagacgcg | aaaacatgct | ttggttcaag | attccaaagt | ctgtctactt | caagcgtgct | 1440 |
| atcctttctg | aagctttatc | tgacttacgt | gacacccaca | agcgtgctat | cattattacc | 1500 |
| gatagaacta | tgactatgtt | aggtcaaact | gacaagatca | ttaaggcttg | tgaaggtcat | 1560 |
| ggtatggtct | gcactgtcta | cgataaggtt | gtcccagatc | caactatcaa | gtgtattatg | 1620 |
| gaaggtgtta | atgaaatgaa | cgtcttcaag | ccagatttag | ctattgctct | tggtggtggt | 1680 |
| tctgctatgg | atgccgctaa | gatgatgcgt | ttattctacg | aatacccaga | ccaagactta | 1740 |
| caagatattg | ctactcgttt | cgtcgatatc | cgtaagcgtg | ttgttggttg | tccaaagctt | 1800 |
| ggtagactta | ttaagactct | tgtctgtatc | ccaactacct | ctggtactgg | tgccgaagtt | 1860 |
| actccattcg | ctgtcgttac | ctctgaagaa | ggtcgtaagt | acccattagt | cgactacgaa | 1920 |
| cttactccag | atatggctat | tgttgatcca | gaattcgctg | ttggtatgcc | aaagcgttta | 1980 |
| acttcttgga | ctggtattga | tgctcttacc | cacgccattg | aatcttacgt | ttctattatg | 2040 |
| gctactgact | tcactagacc | atactctctc | cgtgctgttg | gtcttatctt | cgaatccctt | 2100 |

-continued

```
tcccttgctt acaacaacgg taaggatatt gaagctcgtg aaaagatgca caatgcttct    2160
gctattgctg gtatggcctt tgccaacgct tccttggtt gttgtcactc tgttgctcac    2220
caacttggtt ccgtctacca cattccacac ggtcttgcca acgctttaat gctttctcac    2280
atcattaagt acaacgctac tgactctcca gttaagatgg gtaccttccc acaatacaag    2340
tacccacaag ctatgcgtca ctcgctgaa attgctgaac tcttattacc accaactcaa    2400
gttgttaaga tgactgatgt tgataaggtt caatacttaa ttgaccgtgt tgaacaatta    2460
aaggctgacg ttggtattcc aaagtctatt aaggaaactg gaatggttac tgaagaagac    2520
ttcttcaaca aggttgacca agttgctatc atggccttcg atgaccaatg tactggtgct    2580
aacccacgtt acccattagt ttctgaatta aaacaattaa tgattgatgc ctggaacggt    2640
gttgtcccaa agctctaa                                                   2658
```

<210> SEQ ID NO 52
<211> LENGTH: 885
<212> TYPE: PRT
<213> ORGANISM: Piromyces sp. E2

<400> SEQUENCE: 52

```
Met Ser Gly Leu Gln Met Phe Gln Asn Leu Ser Leu Tyr Gly Ser Leu
1               5                   10                  15

Ala Glu Ile Asp Thr Ser Glu Lys Leu Asn Glu Ala Met Asp Lys Leu
            20                  25                  30

Thr Ala Ala Gln Glu Gln Phe Arg Glu Tyr Asn Gln Glu Gln Val Asp
        35                  40                  45

Lys Ile Phe Lys Ala Val Ala Leu Ala Ala Ser Gln Asn Arg Val Ala
    50                  55                  60

Phe Ala Lys Tyr Ala His Glu Glu Thr Gln Lys Gly Val Phe Glu Asp
65                  70                  75                  80

Lys Val Ile Lys Asn Glu Phe Ala Ala Asp Tyr Ile Tyr His Lys Tyr
                85                  90                  95

Cys Asn Asp Lys Thr Ala Gly Ile Ile Glu Tyr Asp Glu Ala Asn Gly
            100                 105                 110

Leu Met Glu Ile Ala Glu Pro Val Gly Pro Val Val Gly Ile Ala Pro
        115                 120                 125

Val Thr Asn Pro Thr Ser Thr Ile Ile Tyr Lys Ser Leu Ile Ala Leu
    130                 135                 140

Lys Thr Arg Asn Cys Ile Ile Phe Ser Pro His Pro Gly Ala His Lys
145                 150                 155                 160

Ala Ser Val Phe Val Val Lys Val Leu His Gln Ala Ala Val Lys Ala
                165                 170                 175

Gly Ala Pro Glu Asn Cys Ile Gln Ile Ile Phe Pro Lys Met Asp Leu
            180                 185                 190

Thr Thr Glu Leu Leu His His Gln Lys Thr Arg Phe Ile Trp Ala Thr
        195                 200                 205

Gly Gly Pro Gly Leu Val His Ala Ser Tyr Thr Ser Gly Lys Pro Ala
    210                 215                 220

Leu Gly Gly Gly Pro Gly Asn Ala Pro Ala Leu Ile Asp Glu Thr Cys
225                 230                 235                 240

Asp Met Asn Glu Ala Val Gly Ser Ile Val Val Ser Lys Thr Phe Asp
                245                 250                 255

Cys Gly Met Ile Cys Ala Thr Glu Asn Ala Val Val Val Glu Ser
            260                 265                 270
```

-continued

```
Val Tyr Glu Asn Phe Val Ala Thr Met Lys Lys Arg Gly Ala Tyr Phe
            275                 280                 285

Met Thr Pro Glu Glu Thr Lys Lys Ala Ser Asn Leu Leu Phe Gly Glu
    290                 295                 300

Gly Met Arg Leu Asn Ala Lys Ala Val Gly Gln Thr Ala Lys Thr Leu
305                 310                 315                 320

Ala Glu Met Ala Gly Phe Glu Val Pro Glu Asn Thr Val Val Leu Cys
                325                 330                 335

Gly Glu Ala Ser Glu Val Lys Phe Glu Pro Met Ala His Glu Lys
            340                 345                 350

Leu Thr Thr Ile Leu Gly Ile Tyr Lys Ala Lys Asp Phe Asp Asp Gly
        355                 360                 365

Val Arg Leu Cys Lys Glu Leu Val Thr Phe Gly Gly Lys Gly His Thr
    370                 375                 380

Ala Val Leu Tyr Thr Asn Gln Asn Asn Lys Asp Arg Ile Glu Lys Tyr
385                 390                 395                 400

Gln Asn Glu Val Pro Ala Phe His Ile Leu Val Asp Met Pro Ser Ser
                405                 410                 415

Leu Gly Cys Ile Gly Asp Met Tyr Asn Phe Arg Leu Ala Pro Ala Leu
            420                 425                 430

Thr Ile Thr Cys Gly Thr Met Gly Gly Gly Ser Ser Ser Asp Asn Ile
        435                 440                 445

Gly Pro Lys His Leu Leu Asn Ile Lys Arg Val Gly Met Arg Arg Glu
    450                 455                 460

Asn Met Leu Trp Phe Lys Ile Pro Lys Ser Val Tyr Phe Lys Arg Ala
465                 470                 475                 480

Ile Leu Ser Glu Ala Leu Ser Asp Leu Arg Asp Thr His Lys Arg Ala
                485                 490                 495

Ile Ile Ile Thr Asp Arg Thr Met Thr Met Leu Gly Gln Thr Asp Lys
            500                 505                 510

Ile Ile Lys Ala Cys Glu Gly His Gly Met Val Cys Thr Val Tyr Asp
        515                 520                 525

Lys Val Val Pro Asp Pro Thr Ile Lys Cys Ile Met Glu Gly Val Asn
    530                 535                 540

Glu Met Asn Val Phe Lys Pro Asp Leu Ala Ile Ala Leu Gly Gly Gly
545                 550                 555                 560

Ser Ala Met Asp Ala Ala Lys Met Met Arg Leu Phe Tyr Glu Tyr Pro
                565                 570                 575

Asp Gln Asp Leu Gln Asp Ile Ala Thr Arg Phe Val Asp Ile Arg Lys
            580                 585                 590

Arg Val Val Gly Cys Pro Lys Leu Gly Arg Leu Ile Lys Thr Leu Val
        595                 600                 605

Cys Ile Pro Thr Thr Ser Gly Thr Gly Ala Glu Val Thr Pro Phe Ala
    610                 615                 620

Val Val Thr Ser Glu Glu Gly Arg Lys Tyr Pro Leu Val Asp Tyr Glu
625                 630                 635                 640

Leu Thr Pro Asp Met Ala Ile Val Asp Pro Glu Phe Ala Val Gly Met
                645                 650                 655

Pro Lys Arg Leu Thr Ser Trp Thr Gly Ile Asp Ala Leu Thr His Ala
            660                 665                 670

Ile Glu Ser Tyr Val Ser Ile Met Ala Thr Asp Phe Thr Arg Pro Tyr
        675                 680                 685

Ser Leu Arg Ala Val Gly Leu Ile Phe Glu Ser Leu Ser Leu Ala Tyr
```

```
                690                 695                 700
Asn Asn Gly Lys Asp Ile Glu Ala Arg Glu Lys Met His Asn Ala Ser
705                 710                 715                 720

Ala Ile Ala Gly Met Ala Phe Ala Asn Ala Phe Leu Gly Cys Cys His
                725                 730                 735

Ser Val Ala His Gln Leu Gly Ser Val Tyr His Ile Pro His Gly Leu
                740                 745                 750

Ala Asn Ala Leu Met Leu Ser His Ile Ile Lys Tyr Asn Ala Thr Asp
                755                 760                 765

Ser Pro Val Lys Met Gly Thr Phe Pro Gln Tyr Lys Tyr Pro Gln Ala
                770                 775                 780

Met Arg His Tyr Ala Glu Ile Ala Glu Leu Leu Leu Pro Pro Thr Gln
785                 790                 795                 800

Val Val Lys Met Thr Asp Val Asp Lys Val Gln Tyr Leu Ile Asp Arg
                805                 810                 815

Val Glu Gln Leu Lys Ala Asp Val Gly Ile Pro Lys Ser Ile Lys Glu
                820                 825                 830

Thr Gly Met Val Thr Glu Glu Asp Phe Phe Asn Lys Val Asp Gln Val
                835                 840                 845

Ala Ile Met Ala Phe Asp Asp Gln Cys Thr Gly Ala Asn Pro Arg Tyr
                850                 855                 860

Pro Leu Val Ser Glu Leu Lys Gln Leu Met Ile Asp Ala Trp Asn Gly
865                 870                 875                 880

Val Val Pro Lys Leu
                885
```

ACETYL-CoA PRODUCING ENZYMES IN YEAST

CROSS REFERENCE TO RELATED APPLICATIONS

This application is a Continuation of U.S. application Ser. No. 12/670,050, filed May 7, 2010, which is a § 371 National Stage Application of International Application No. PCT/EP2008/059119, filed Jul. 11, 2008, which claims priority to European Application No. 07112956.3, filed Jul. 23, 2007, U.S. Provisional Application No. 60/935,031, filed Jul. 23, 2007, European Application No. 07123976.8, filed Dec. 21, 2007, European Application No. 08101747.7, filed Feb. 19, 2008, and U.S. Provisional Application No. 61/064,120, filed Feb. 19, 2008, the content of all of which are incorporated herein by reference in their entireties.

BACKGROUND OF THE INVENTION

The present invention is in the field of metabolites production in yeast using heterologous expression systems. In particular, the present invention relates to the metabolic engineering of yeast strains capable of producing metabolites that require cytosolic acetyl-CoA as a precursor, such as butanol-producing yeast strains. The present invention relates to an assay system for identifying heterologous enzymes capable of converting pyruvate, acetaldehyde or acetate into cytosolic acetyl-CoA when expressed in the cytosol in yeast.

Acetyl-coenzyme A (CoA) is an essential intermediate in numerous metabolic pathways, and is a key precursor in the synthesis of many industrial relevant compounds, such as fatty acids, carotenoids, isoprenoids, vitamins, amino acids, lipids, wax esters, (poly)saccharides polyhydroxyalkanoates, statins, polyketides and acetic esters (such as ethyl acetate and isoamyl acetate). In particular, acetyl-CoA is also the precursor of the industrially important bulk chemical 1-butanol.

Compared to bacteria, such as *E. coli*, yeast cells provide a very suitable alternative to produce the above-mentioned acetyl-CoA derived products, in that yeast is not susceptible to phage or other infection since yeast-based processes may be run at low pH. Therefore, the use of yeast does not require a sterile process, thereby lowering the cost price of the product of interest.

When natural (wild type) yeast is not able to produce the acetyl-CoA-derived product of interest, the use of metabolic engineering can provide for yeast cells expressing heterologous genes that could support such a process. In such cases, the heterologous gene products are usually targeted to the cytosolic compartment of yeast. As the biosynthesis of acetyl-CoA-derived product will take place completely or partially in the cytosol, the supply of sufficient amounts of the precursor acetyl-CoA in the cytosolic compartment is crucial. In *Saccharomyces cerevisiae*, biosynthesis of acetyl-CoA takes place in two separate compartments. In mitochondria, acetyl-CoA is synthesized by oxidative decarboxylation of pyruvate catalyzed by the pyruvate dehydrogenase complex (PDH), with the following overall reaction stoichiometry:

In cytosol, acetyl-CoA is synthesized via the pyruvate dehydrogenase (PDH) by-pass, involving the enzymes pyruvate decarboxylase (PDC), acetaldehyde dehydrogenase (ALD), and acetyl-CoA synthetase (ACS), with the following overall reaction stoichiometry:

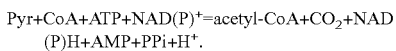

Pyruvate-decarboxylase-negative (Pdc−) mutant of the yeast *S. cerevisiae* does not have a functional PDH by-pass, and cannot grow on minimal medium with glucose as the sole carbon source due to inability to supply (sufficient) cytosolic acetyl-CoA for growth (Flikweert et al., (1996) Yeast 12:247-57). The PDH by-pass is therefore essential in providing acetyl-CoA in the cytosolic compartment. However, the PDH bypass in yeast is not optimal with respect to the energy balance, as can be seen from the overall reaction stoichiometry: 2 moles of ATP are needed per acetyl-CoA synthesized via the PDH-bypass since in the acetyl-CoA synthetase reaction ATP is hydrolyzed to AMP. In contrast, the mitochondrial pathway via the PDH requires no ATP. The additional ATP requirement of the PDH by-pass can present a problem for synthesizing the product of interest from cytosolic acetyl-CoA precursor, as more carbon source needs to be diverted for ATP generation, via e.g. oxidative phosphorylation and/or substrate phosphorylation (e.g. glycolysis), thereby lowering the overall yield of the product on carbon.

When yeast is metabolically engineered to produce 1-butanol, heterologous biosynthetic genes of 1-butanol can be expressed in the cytosol in yeast cells (WO 2007/041269). In general 1 mole of glucose give rise to 2 moles of acetyl-CoA via glycolysis, which is the precursor of 1 mole of butanol; hence a maximum of 1 mole of butanol can be synthesized per mole of glucose if cell growth and maintenance is not considered. However, when the PDH by-pass is used in combination with butanol biosynthesis, this maximal theoretical yield cannot be achieved due to energy imbalance: whereas 2 moles of ATP are generated per mole of glucose converted in glycolysis, a total of 4 moles (2 times 2 mole) of ATP are needed in the PDH by-pass to form 2 moles of acetyl-CoA, which are converted to 1 mole of butanol. Thus, there is a net shortage of ATP if the PDH by-pass were used to synthesize 1 mole of 1-butanol from 1 mole of glucose.

Thus, there is a need for the identification of possible alternative metabolic routes for producing cytosolic acetyl-CoA in yeast, for the production of acetyl-CoA-derived products, in particular butanol, wherein the PDH by-pass is not required.

Butanol is an important industrial chemical and is suitable as an alternative engine fuel having improved properties over ethanol. Butanol also finds use as a solvent for a wide variety of chemical and textile processes, in the organic synthesis of plastics, as a chemical intermediate and as a solvent in the coating and food and flavor industry. Butanol can be produced from biomass (biobutanol) as well as fossil fuels (petrobutanol).

The chemical synthesis of butanol in one of its isomers can be accomplished by a variety of available methods known in the art (see e.g. Ullmann's Encyclopedia of Industrial Chemistry, 6th edition, 2003, Wiley-VCHVerlag GmbH and Co., Weinheim, Germany, Vol. 5, pp. 716-719). These processes have the disadvantage that they are based on the use of petrochemical derivates, are generally expensive, and are not environmentally friendly.

Biological synthesis of butanol can be achieved by fermentation using the acetone-butanol-ethanol (ABE) process carried out by the bacteria *Clostridium acetobutylicum* or other *Clostridium* species. An important disadvantage of the ABE process, however, is that it results in a mixture of acetone, 1-butanol and ethanol. Moreover, the use of bacteria requires sterile process conditions and generally renders the process susceptible to bacteriophage infection. Yeast cells thus provide a very suitable alternative as described above.

SUMMARY OF THE INVENTION

The present inventors have now identified alternative metabolic routes for increasing the production of cytosolic acetyl-CoA in yeast which can overcome the problems of the PDH by-pass.

One possible route includes the direct conversion of acetaldehyde to acetyl-CoA without ATP consumption, by use of an acetylating acetaldehyde dehydrogenase (E.C. 1.2.1.10) (see FIG. 2, reaction A, ACDH). Another route includes the direct conversion of pyruvate to acetyl-CoA by an enzyme or a multi-enzyme-complex without ATP consumption, for instance, by use of a pyruvate:NADP oxidoreductase (E.C. 1.2.1.51) see FIG. 2, reaction C, PNO). In these two possible routes, the formation of 1 mole of butanol per mole of glucose would result in the formation of 2 moles of ATP. Yet another route includes the conversion of acetate to acetyl-CoA with 1 ATP consumed per acetyl-CoA formed by an alternative enzyme or a combination of enzymes, for instance, by use of acetate:CoA ligase (ADP-forming, E.C. 6.2.1.13), or by use of ATP:acetate phosphotransferase (E.C. 2.7.2.1) in combination with acetyl-CoA:Pi acetyltransferase (E.C. 2.3.1.8). In this route, the formation of 1 mole of butanol per mole of glucose is ATP-balanced, i.e. no ATP will be formed. The present inventors have now found that such an alternative to the PDH by-pass can result in acetyl-CoA synthesis in the cytosol of the yeast, and that such acetyl-CoA can be used biosynthetically to produce higher amounts of desirable fementation products, such as butanol.

In a first aspect, the present invention provides a method of identifying a heterologous polypeptide having enzymatic activity for converting pyruvate, acetaldehyde or acetate into acetyl-CoA in (the cytosol of) a yeast cell comprising:
providing a mutated yeast cell, wherein said mutation comprises an inactivation of at least one gene of the (PDH) by-pass, selected from the genes encoding the enzymes pyruvate decarboxylase (PDC), acetaldehyde dehydrogenase (ALD), and acetyl-CoA synthetase (ACS);
transforming said mutated yeast cell with an expression vector comprising at least one heterologous nucleotide sequence operably linked to a promoter functional in yeast and said at least one heterologous nucleotide sequence encoding at least one candidate polypeptide having potential enzymatic activity for converting pyruvate, acetaldehyde or acetate into acetyl-CoA;
testing said recombinant mutated yeast cell for its ability to grow on minimal medium containing glucose as sole carbon source, and
identifying said candidate polypeptide as a heterologous polypeptide having enzymatic activity for converting pyruvate, acetaldehyde or acetate into acetyl-CoA in (the cytosol of) said yeast cell when growth of said cell is observed.

In a preferred embodiment of said method the yeast cell is a cell of *Saccharomyces cerevisiae* and the heterologous nucleotide sequence is codon (pair) optimized for expression in *Saccharomyces cerevisiae*.

In another preferred embodiment, said mutation comprises an inactivation of the gene for acetyl-CoA synthetase isoform 2 (acs2).

In another preferred embodiment, said at least one candidate polypeptide having enzymatic activity for converting acetaldehyde into acetyl-CoA is a (putative) acetylating acetaldehyde dehydrogenases.

Alternatively, said at least one heterologous polypeptide having enzymatic activity for converting pyruvate, acetaldehyde or acetate into acetyl-CoA in (the cytosol of) a yeast cell may consist of two or more enzymes working together to achieve the desired conversion from pyruvate, acetaldehyde or acetate into acetyl-CoA.

In another aspect, the present invention provides an integration vector for the integration in a yeast genome of a heterologous nucleotide sequence encoding a polypeptide having enzymatic activity for converting pyruvate, acetaldehyde or acetate into acetyl-CoA, and the subsequent expression of the heterologous polypeptide therefrom.

In another aspect, the present invention provides an expression vector expressing heterologous polypeptides in yeast, said expression vector comprising a heterologous nucleotide sequence operably linked to a promoter functional in yeast and said heterologous nucleotide sequence encoding a polypeptide having enzymatic activity for converting pyruvate, acetaldehyde or acetate into acetyl-CoA in (the cytosol of) said yeast cell.

In a preferred embodiment of said vector the polypeptide having enzymatic activity for converting pyruvate, acetaldehyde or acetate into acetyl-CoA is identified by a method according to the present invention as described above.

In another preferred embodiment, said polypeptide is selected from SEQ ID NO: 19, 22, 25, 28 and 52 and functional homologues thereof.

In another preferred embodiment, said expression vector is for expression in *Saccharomyces cerevisiae*, wherein said heterologous nucleotide sequence is codon (pair) optimized for expression in *Saccharomyces cerevisiae*.

In another preferred embodiment, said heterologous nucleotide sequence is selected from SEQ ID NO: 20, 23, 26 and 29.

In another aspect, the present invention provides a recombinant yeast cell comprising the expression vector of the present invention as described above.

In a preferred embodiment, the recombinant yeast cell further comprises an inactivation of at least one gene of the (PDH) by-pass, selected from the genes encoding the enzymes pyruvate decarboxylase (PDC), acetaldehyde dehydrogenase (ALD), and acetyl-CoA synthetase (ACS).

Preferably, a yeast cell according to the present invention comprises an inactivation of a gene encoding an acetyl-CoA synthase.

In another preferred embodiment, the recombinant yeast cell further comprises an inactivation of a gene (nucleotide sequence) encoding an enzyme capable of catalysing the conversion of acetaldehyde to ethanol, preferably a gene encoding an alcohol dehydrogenase.

As used herein, inactivation of a gene (nucleotide sequence) encoding an enzyme may be achieved by mutation, deletion or disruption of (part of) a gene or nucleotide sequence encoding an enzyme.

Preferably a yeast cell according to the present invention shows growth on minimal medium containing glucose as sole carbon source.

In another preferred embodiment of a yeast cell of the invention, said yeast cell further comprises one or more introduced genes encoding a recombinant pathway for the formation of 1-butanol from cytosolic acetyl-CoA. Suitable recombinant pathways from acetyl-CoA to 1-butanol are known in the art. Such pathways are for instance known from WO 2007/041269. Preferably said one or more introduced genes encode enzymes that produce acetoacetyl-CoA, 3-hydroxybutyryl-CoA, crotonyl-CoA, butyryl-CoA, butylaldehyde and/or 1-butanol. Said enzymes can be:

acetyl-CoA acetyltransferase (E.C. 2.3.1.9 [Enzyme Nomenclature 1992, Academic Press, San Diego]; although, enzyme's with a broader substrate range (E.C. 2.3.1.16) will be functional as well), which converts 2 moles of acetyl-CoA to acetoacetyl-CoA;

NADH-dependent or NADPH-dependent 3-hydroxybutyryl-CoA dehydrogenase E.C. 1.1.1.35 or E.C. 1.1.1.30, resp. E.C. 1.1.1.157 or E.C. 1.1.1.36), which converts acetoacetyl-CoA to 3-hydroxybutyryl-CoA;

3-hydroxybutyryl-CoA dehydratase (also named crotonase; E.C. 4.2.1.17 or E.C. 4.2.1.55), which converts 3-hydroxybutyryl-CoA to crotonyl-CoA;

NADH-dependent or NADPH-dependent butyryl-CoA dehydrogenase (E.C. 1.3.1.44 resp. E.C. 1.3.1.38 or E.C.1.3.99.2), which converts crotonyl-CoA to butyryl-CoA;

monofunctional NADH-dependent or NADPH-dependent aldehyde dehydrogenase (E.C. 1.2.1.10, or 1.2.1.57), which converts butyryl-CoA to butyraldehyde, and NADH-dependent or NADPH-dependent butanol dehydrogenase (E.C. 1.1.1.-), which converts butylaldehyde to 1-butanol, or bifunctional NADH-dependent or NADPH-dependent aldehyde/alcohol dehydrogenase (E.C. 1.1.1.1./ 1.2.1.10), which converts butyryl-CoA to 1-butanol via butyraldehyde In another preferred embodiment of the invention a yeast cell is a *Saccharomyces cerevisiae*.

In another aspect, the present invention provides a method of producing butanol, comprising the steps of fermenting a suitable carbon substrate with a yeast cell according to the present invention and recovering the butanol produced during said fermentation.

DETAILED DESCRIPTION OF THE INVENTION

Definitions

Figure 1:
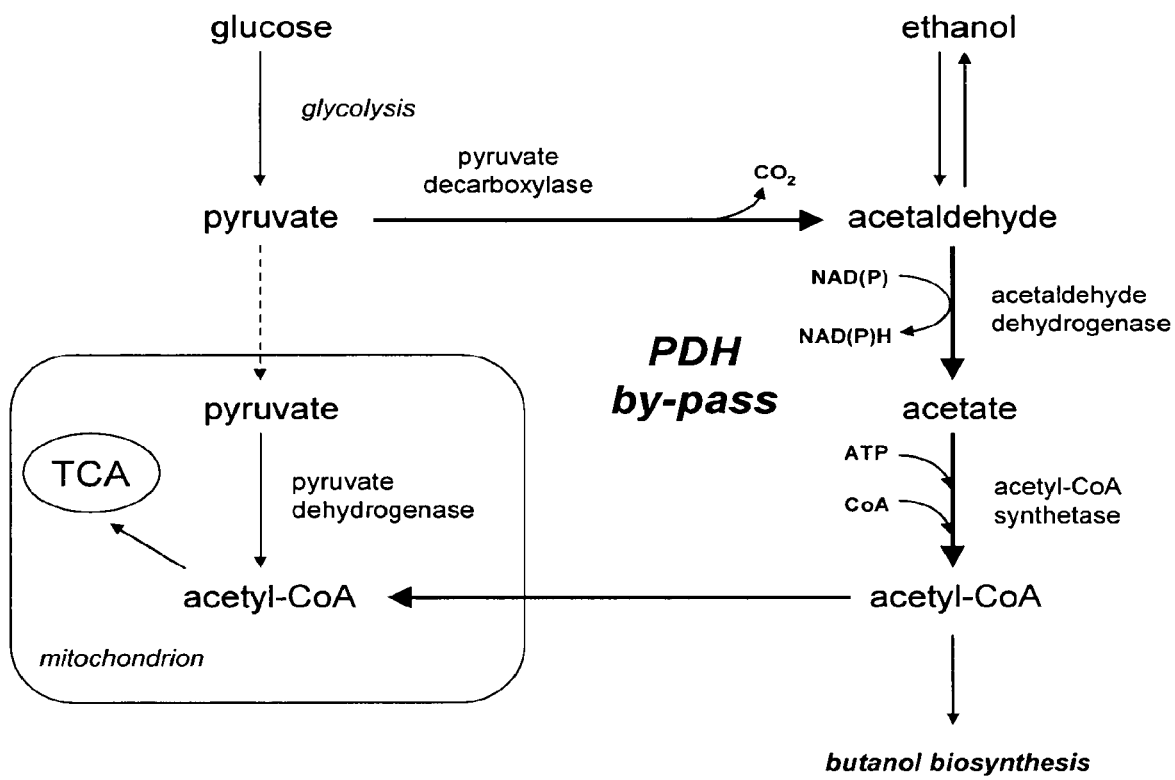
FIG. 1 is a schematic presentation of the PDH by-pass showing the enzymes pyruvate decarboxylase (PDC; E.C. 4.1.1.1), acetaldehyde dehydrogenase (ALD; E.C. 1.2.1.3, E.C. 1.2.1.4 and E.C. 1.2.1.5), and acetyl-CoA synthetase (ACS; E.C. 6.2.1.1).

The term "butanol" refers to n-butanol, or 1-butanol.

The term "yeast" refers to a phylogenetically diverse group of single-celled fungi, most of which are in the division of Ascomycota and Basidiomycota. The budding yeasts ("true yeasts") are classified in the order Saccharomycetales, with *Saccharomyces cerevisiae* as the most well known species The term "recombinant yeast" as used herein, is defined as a cell which contains a nucleotide sequence and/or protein, or is transformed or genetically modified with a nucleotide sequence that does not naturally occur in the yeast, or it contains additional copy or copies of an endogenous nucleic acid sequence (or protein), or it contains a mutation, deletion or disruption of an endogenous nucleic acid sequence.

The term "mutated" as used herein regarding proteins or polypeptides means that at least one amino acid in the wild-type or naturally occurring protein or polypeptide sequence has been replaced with a different amino acid, or deleted from the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sambrook et al., Molecular Cloning-A Laboratory Manual, 2nd ed., Vol. 1-3 (1989). The term "mutated" as used herein regarding genes means that at least one nucleotide in the nucleotide sequence of that gene or a regulatory sequence thereof, has been replaced with a different nucleotide, or has been deleted from the sequence via mutagenesis, resulting in the transcription of a non-functional protein sequence or the knockout of that gene.

The term "gene", as used herein, refers to a nucleic acid sequence containing a template for a nucleic acid polymerase, in eukaryotes, RNA polymerase II. Genes are transcribed into mRNAs that are then translated into protein.

The term pyruvate dehydrogenase (PDH) by-pass refers to the enzymatic cascade form pyruvate to acetyl-CoA in the cytosol of yeast, and which consists of the following enzymes: pyruvate decarboxylase (PDC; E.C. 4.1.1.1) converting pyruvate into acetaldehyde; acetaldehyde dehydrogenase (ALD; E.C. 1.2.1.3, E.C. 1.2.1.4 and E.C. 1.2.1.5), converting acetaldehyde into acetate; and acetyl-CoA synthetase (ACS; E.C. 6.2.1.1), converting acetate into acetyl-CoA.

The term "nucleic acid" as used herein, includes reference to a deoxyribonucleotide or ribonucleotide polymer, i.e. a polynucleotide, in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation.

Sequence identity is herein defined as a relationship between two or more amino acid (polypeptide or protein) sequences or two or more nucleic acid (polynucleotide) sequences, as determined by comparing the sequences. Usually, sequence identities are compared over the whole length of the sequences compared. In the art, "identity" also means the degree of sequence relatedness between amino acid or nucleic acid sequences, as the case may be, as determined by the match between strings of such sequences.

Preferred methods to determine identity are designed to give the largest match between the sequences tested. Methods to determine identity are codified in publicly available computer programs. Preferred computer program methods to determine identity and similarity between two sequences include BLASTP, BLASTN (Altschul, S. F. et al., J. Mol. Biol. 215:403-410 (1990), publicly available from NCBI and other sources (BLAST Manual, Altschul, S., et al., NCBI NLM NIH Bethesda, Md. 20894). Preferred parameters for amino acid sequences comparison using BLASTP are gap open 11.0, gap extend 1, Blosum 62 matrix.

Every nucleic acid sequence herein that encodes a polypeptide also, by reference to the genetic code, describes every possible silent variation of the nucleic acid. The term "conservatively modified variants" applies to both amino acid and nucleic acid sequences. With respect to particular nucleic acid sequences, conservatively modified variants refers to those nucleic acids which encode identical or conservatively modified variants of the amino acid sequences due to the degeneracy of the genetic code. The term "degeneracy of the genetic code" refers to the fact that a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation.

"Expression" refers to the transcription of a gene into structural RNA (rRNA, tRNA) or messenger RNA (mRNA) with subsequent translation into a protein.

As used herein, "heterologous" in reference to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

As used herein "promoter" is a DNA sequence that directs the transcription of a (structural) gene. Typically, a promoter is located in the 5'-region of a gene, proximal to the transcriptional start site of a (structural) gene. Promoter sequences may be constitutive, inducible or repressible. If a promoter is an inducible promoter, then the rate of transcription increases in response to an inducing agent.

The term "vector" as used herein, includes reference to an autosomal expression vector and to an integration vector used for integration into the chromosome.

The term "expression vector" refers to a DNA molecule, linear or circular, that comprises a segment encoding a polypeptide of interest under the control of (i.e., operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both. In particular an expression vector comprises a nucleotide sequence that comprises in the 5' to 3' direction and operably linked: (a) a yeast-recognized transcription and translation initiation region, (b) a coding sequence for a polypeptide of interest, and (c) a yeast-recognized transcription and translation termination region. "Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e., operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is nonfunctional in that organism. Integration of the segment comprising the gene of interest may be selected if an appropriate marker is included within that segment.

As used herein, the term "operably linked" refers to a juxtaposition wherein the components so described are in a relationship permitting them to function in their intended manner. A control sequence "operably linked" to another control sequence and/or to a coding sequence is ligated in such a way that transcription and/or expression of the coding sequence is achieved under conditions compatible with the control sequence. Generally, operably linked means that the nucleic acid sequences being linked are contiguous and, where necessary to join two protein coding regions, contiguous and in the same reading frame.

By "host cell" is meant a cell which contains a vector and supports the replication and/or expression of the vector. Host cells may be prokaryotic cells such as E. coli, or eukaryotic cells such as yeast, insect, amphibian, or mammalian cells. Preferably, host cells are cells of the order of Actinomycetales, most preferably yeast cells, most preferably cells of Saccharomyces cerevicsiae.

"Transformation" and "transforming", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

The term "oligonucleotide" refers to a short sequence of nucleotide monomers (usually 6 to 100 nucleotides) joined by phosphorous linkages (e.g., phosphodiester, alkyl and aryl-phosphate, phosphorothioate, phosphotliester), or non-phosphorous linkages (e.g., peptide, sulfamate and others). An oligonucleotide may contain modified nucleotides having modified bases (e.g., 5-methyl cytosine) and modified sugar groups (e.g., 2'-O-methyl ribosyl, 2'-O-methoxyethyl ribosyl, 2'-fluoro ribosyl, 2'-amino ribosyl, and the like). Oligonucleotides may be naturally-occurring or synthetic molecules of double- and single-stranded DNA and double- and single-stranded RNA with circular, branched or linear shapes and optionally including domains capable of forming stable secondary structures (e.g., stem-and-loop and loop-stem-loop structures).

The term "polynucleotide" as used herein refers to a polymeric form of nucleotides of any length, either ribonucleotides or deoxyribonucleotides. Thus, this term includes double- and single-stranded DNA and RNA.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature; or (2) is linked to a polynucleotide other than that to which it is linked in nature; or (3) does not occur in nature.

The term "minimal medium" as used herein refers to a chemically defined medium, which includes only the nutrients that are required by the cells to survive and proliferate in culture. Typically, minimal medium is free of biological extracts, e.g., growth factors, serum, pituitary extract, or other substances, which are not necessary to support the survival and proliferation of a cell population in culture. For example, minimal medium generally includes as essential substances: at least one carbon source, such as glucose; at least one nitrogen source, such as ammonium, ammonium sulfate, ammonium chloride, ammonium nitrate or urea; inorganic salts, such as dipotassium hydrogenphosphate, potassium dihydrogen-phosphate and magnesium sulfate; and other nutrients, such as biotin and vitamins.

DESCRIPTION OF THE PREFERRED EMBODIMENTS

A method of the present invention provides a method for identifying heterologous enzymes capable of producing acetyl-CoA in the cytosol of a yeast cell. The heterologous enzyme may produce the acetyl-CoA using pyruvate, acetaldehyde or acetate as a substrate, preferably in a single conversion step. Preferably, the heterologous enzyme produces the acetyl-CoA from acetaldehyde. An enzyme capable of catalyzing said reaction is acetylating acetaldehyde dehydrogenase (acdh; E.C. 1.2.1.10) also referred to as acetaldehyde:NAD+ oxidoreductase (CoA-acetylating). The conversion of acetaldehyde into acetyl-CoA by acetylating acetaldehyde dehydrogenase is reversible and runs in the direction of acetyl-CoA when acetaldehyde accumulates in the cytosol. Such an accumulation may for instance be achieved by deletion of alcohol dehydrogenase (adh; E.C. 1.1.1.1).

The heterologous enzyme may also produce the acetyl-CoA from pyruvate. An enzyme capable of catalyzing said reaction is a pyruvate:NADP oxidoreductase (pno; E.C. 1.2.1.51). The reaction is stoichiometrically identical to the mitochondrial pyruvate dehydrogenase except that pno uses NADPH as a cofactor as compared to PDH that uses NADH. Compared to acdh, an important disadvantage of the pno enzyme system is that pno is oxygen sensitive, and that it is a large multimeric enzyme, and hence, its successful genetic incorporation (a 5-6 kb gene) is much more difficult than that of acdh. For this reason, the use of acdh is preferred in embodiments of the present invention.

An important feature of a test cell capable of revealing the desired enzymatic activity of a test polypeptide is that the cell is prototrophic as a result of the introduced polypeptide. With this, it is meant that the cell's nutritional requirements do not exceed those of the corresponding wild-type strain and that it will proliferate on minimal medium (in contrast to the auxotroph). In fact, the production of acetyl-CoA as supported by the test polypeptide will cancel the effect of the deletion of said at least one gene of the PDH by-pass, caused by the deletion of the gene for pyruvate decarboxylase (pdc; E.C. 4.1.1.1), acetaldehyde dehydrogenase (ald; E.C. 1.2.1.3, E.C. 1.2.1.4 or E.C. 1.2.1.5), or acetyl-CoA synthetase (acs; E.C. 6.2.1.1). Such complementation assays are well known in the art. In aspects of the present invention the assay is used to identify suitable sources of heterologous enzymes capable of sustaining cytosolic acetyl-CoA production in yeast cells.

The complementation assay is based on the provision of alternative routes to overcome the deleted enzyme activity of the PDH by-pass. Methods for effecting deletion of genes in yeast are well known in the art, and can for instance be achieved by oligonucleotide-mediated mutagenesis. Good results may be obtained with the plasmid pUG6 carrying the loxP-kanMX-loxP gene disruption cassette (Güldener et al. [1996] Nucleic Acids Res. 24(13):2519-24; GenPept accession no. P30114). Thus, the skilled person will be able to provide a yeast strain having a deleted acetaldehyde dehydrogenase and/or acetyl-CoA synthetase gene for blocking the PDH by-pass therein.

Saccharomyces cerevisiae comprises two acetyl-CoA synthetase isoforms, Acs1p and Acs2p. Both are the nuclear source of acetyl-CoA for histone acetylation. The production of cytosolic acetyl-CoA is also required for lipid production. Acs activity is essential, since an acs1 acs2 double null mutant is non-viable. An acs1 null mutant can grow with ethanol as the sole carbon source. The mutated yeast cell used in aspects of the present invention preferably has an inactivation of the acs2 gene.

Saccharomyces cerevisiae mutants carrying an inactivation of the acs2 gene are not able to grow on glucose as sole carbon source, because ACS1 is repressed and the protein is actively degraded. Complementation of such a delta acs2 mutant with a plasmid based acs gene will restore the cell's ability to grow on glucose as single carbon source. In addition, growth of such a mutant is complemented by the expression of genes supporting alternative routes for the production of sufficient cytosolic acetyl-CoA. Thus, transformation of the delta acs2 mutant with a plasmid from which a functional (heterologous) acdh or pno can be expressed will restore the mutant's ability to grow on glucose as sole carbon source. It should be understood that in addition to the removal of the ACS2 locus, one may also remove the ACS1 locus. Although it is believed that this may in some instances prevent the occurrence of revertants (mutations in the ACS1 locus leading to reversion of the delta acs2 phenotype), this was however not found to be essential. Double mutants (acs1/acs2Δ, strains) would be wholly dependant on the introduced acdh or pno gene for the production of cytosolic acetyl-CoA.

An important advantage of a complementation assay of the present invention is that it can be performed as a plate screening assay wherein successful complementation is observed as colony growth. This is much faster than experiments that require the analysis for the production of a desired metabolic product.

For complementation of the mutation, the yeast cell having the inactivated ald and/or acs gene is then transformed with a suitable expression vector comprising a nucleotide sequence of a heterologous test polypeptide.

Yeast expression vectors are widely available from a variety of commercial suppliers. To date, functional complementation of yeast mutations by foreign homologues has become a standard practice in engineering of Saccharomyces cerevisiae. Suitable expression vectors for heterologous gene expression may be based on artificial, inducible promoters such as the GAL promoter, but is preferably based on constitutive promotors such as the TDH3 promoter. Suitable systems are exemplified in the examples below. In certain production systems, the use of an inducible promotor may be preferred, as it would allow for temporal separation of stages for biomass production (promotor not induced) and fermentation product production (promoter induced). In another highly preferred embodiment in certain production systems, the vector is in integration vector for stable integrating the heterologous genes in the genome of the yeast production strain.

In order to achieve optimal expression in yeast, the codon (pair) usage of the heterologous gene may be optimized by using any one of a variety of synthetic gene design software packages, for instance GENEOPTIMIZER® from Geneart AG (Regensburg, Germany) for codon usage optimization or codon pair usage optimization as described in WO2008/000632. Such adaptation of codon usage ensures that the heterologous genes, which are for instance of bacterial origin, are effectively processed by the yeast transcription and translation machinery. Optimization of codon pair usage will result in enhanced protein expression in the yeast cell.

The optimized sequences may for instance be cloned into a high copy yeast expression plasmid, operably linked to a (preferably constitutive) promoter functional in yeast. Good results have been obtained with the plasmid YEplac112 (2μ TRP1) (Gietz & Sugino [1988] Gene 74(2):527-34).

Heterologous genes that encode a candidate polypeptide having potential enzymatic activity for converting pyruvate, acetaldehyde or acetate into acetyl-CoA may be identified in silico. Suitable enzymes described as possessing the capacity to convert acetaldehyde into acetyl-CoA are acetylating acetaldehyde dehydrogenases (E.C. 1.2.1.10). The nucleotide and amino acid sequences of over 200 of these enzymes from a variety of microbial origins are described in various databases (e.g. the KEGG (Kyoto Encyclopedia of Genes and Genomes) database).

The present inventors have selected several acetylating acetaldehyde dehydrogenases and tested these in the delta acs2 mutant-based assay system of the present invention. Many of these, though not all, were functional in S. cerevisiae when codon pair usage was optimized.

Functional homologues to these proteins can also be used in aspects of the present invention. The term "functional homologues" as used herein refers to a protein comprising the amino acid sequence of SEQ ID NO:19, 22, 25 or the acetaldehyde dehydrogenase part of SEQ ID NOs: 28 and 52 in which one or more amino acids are substituted, deleted, added, and/or inserted, and which protein has the same enzymatic functionality for substrate conversion, for instance an acetylating acetaldehyde dehydrogenase homologue is capable of converting acetaldehyde into acetyl-CoA. This functionality may be tested by use of an assay system comprising a recombinant yeast cell comprising an expression vector for the expression of the homologue in yeast, said expression vector comprising a heterologous nucleotide sequence operably linked to a promoter functional in yeast and said heterologous nucleotide sequence encoding the homologous polypeptide of which enzymatic activity for converting pyruvate, acetaldehyde or acetate into acetyl CoA in (the cytosol of) said yeast cell is to be tested, and performing a method for identifying a heterologous polypeptide having enzymatic activity for converting pyruvate, acetaldehyde or acetate into acetyl-CoA in (the cytosol of) a yeast cell as described herein using said assay system. Candidate homologues may be identified by using in silico similarity analyses. A detailed example of such an analysis is described in Example 2 below. The skilled person will be able to derive therefrom how suitable candidate homologues may be found and, optionally upon codon(pair) optimization, will be able to test the required functionality of such candidate homologues using the assay system of the present invention as described above. A suitable homologue represents a polypeptide having an amino acid sequence identity to an acetylating acetaldehyde dehydrogenase of more than 50%, preferably more than 60%, more preferably more than 70%, 80%, 90% or more, for instance having such an amino acid sequence identity to SEQ ID NOs:19, 22, 25, or the acetaldehyde dehydrogenase part of SEQ ID NOs:28 and 52 and having the required enzymatic functionality for converting acetaldehyde into acetyl-CoA. Similarly, enzymes described for the direct conversion of pyruvate into acetyl-CoA and the functional homologues thereof, as well as enzymes described for the conversion of acetate to acetyl-CoA and the functional homologues thereof, can also be used, similar as described for acetylating acetaldehyde dehydrogenase above.

A method of the present invention further comprises the step of testing the ability of the mutated and test-protein transformed yeast cell to grow on minimal medium containing glucose as sole carbon source. As stated earlier, this may suitably occur on solid (agar) media in Petri dishes (plates) where growth can be observed as growth of a colony, however, liquid media are equally suitable and growth may be detected by turbidity. Other methods for determining growth of the mutated and test-protein transformed yeast cell on minimal medium containing glucose as sole carbon source may also be used.

When the mutated and test-protein-transformed yeast cell is capable of growth on minimal medium with glucose, the candidate polypeptide is successfully identified as a heterologous polypeptide having enzymatic activity for converting pyruvate, acetaldehyde or acetate into acetyl-CoA in (the cytosol of) said yeast cell. Growth may suitably be observed as colony formation on solid growth media, in particular minimal medium containing glucose.

An expression vector for the expression of heterologous polypeptides in yeast, according to the present invention may be any expression vector suitable for transforming yeast. Innumerable examples are available in the art that can suitably be used to express heterologous nucleotide sequences in yeast. A very suitable vector in aspects of the invention is a plasmid. A highly preferred plasmid is YEplac112PtdhTadh (SEQ ID NO:40).

Generally, the heterologous nucleotide sequence encoding the polypeptide having enzymatic activity for converting pyruvate, acetaldehyde or acetate into acetyl CoA in (the cytosol of) said yeast cell, will be placed under control of a promoter functional in yeast. Preferably the promoter is a constitutive promoter. The promoter on plasmid YEplac112PtdhTadh is the TDH3 promoter.

The heterologous nucleotide sequences incorporated in the expression vector of the present invention may be any pno, acdh or other enzyme capable of converting pyruvate, acetaldehyde or acetate (respectively) into acetyl-CoA in the cytosol of the yeast. Preferred nucleotide sequences are those as identified herein, namely the nucleotide sequences encoding:

the ethanolamine utilization protein EutE from *E. coli* HS (nucleotide sequences with SEQ ID NO:18);
the hypothetical protein Lin1129 from *Listeria innocua* similar to ethanolamine utilization protein EutE, (nucleotide sequences with SEQ ID NO:21)
the acetaldehyde dehydrogenase EDK33116 from *Clostridium kluyveri* DSM 555 (nucleotide sequences with SEQ ID NO:24); and
the adhE homologue of *S. aureus* (nucleotide sequences with SEQ ID NO:27) encoding a bifunctional acetaldehyde/alcohol dehydrogenase in *Staphylococcus aureus* subsp. *aureus* N315, or the acetaldehyde dehydrogenase functional part thereof.
the adhE homologue of *Piromyces* sp. E2 (nucleotide sequence SEQ ID NO: 51) encoding a bifunctional acetaldehyde/alchol dehydrogenase, or the acetaldehyde dehydrogenase part thereof.

Also suitable are functional homologues of these nucleotide sequences, or of the polypeptides that they encode. With this term is meant that a nucleic acid sequence having more than 80%, 90% or 95% sequence identity with the nucleotide sequences encoding the above acdh enzymes, or having more than 50%, preferably more than 60%, 70%, 80%, 90%, or 95% sequence identity with the amino acid sequence of the above acdh enzymes, with the proviso that the polypeptides encoded by the homologous sequences exhibit functional enzymatic acdh activity.

As stated above, these nucleotide sequences can be optimized for expression in *Saccharomyces cerevisiae* by optimization of codon pair usage well known in the art. Codon pair optimized sequences for the SEQ ID NO:18, 21, 24, and 27 are provided in SEQ ID NO:20, 23, 26, and 29, respectively.

The expression vector of the invention may be used to transform a yeast cell. Methods of transformation include electroporation, glass bead and biolistic transformation, all of which are well known in the art and for instance described in Sambrook et al., Molecular Cloning-A Laboratory Manual, 2nd ed., Vol. 1-3 (1989).

A yeast cell according to the present invention comprises a heterologous nucleotide sequence encoding a polypeptide having enzymatic activity for converting pyruvate, acetaldehyde or acetate into acetyl-CoA in (the cytosol of) said yeast cell. Preferably, a yeast cell of the invention comprises a heterologous acdh or pno. The advantage of such a yeast cell is that it can produce acetyl-CoA by a metabolic route wherein the PDH by-pass is not required. This is energetically more favourable under anaerobic conditions, and may form the basis of any biological synthesis process using yeast cells under anaerobic conditions where acetyl-CoA is an intermediate. In addition to comprising the heterologous acdh or pno, the yeast cell of the invention may comprise various gene deletions or gene supplementations, depending on the intended use of the yeast.

Preferably a yeast cell according to the present invention comprises an inactivation of a nucleotide sequence (gene) encoding an enzyme capable of catalysing the conversion of acetaldehyde to ethanol, preferably an alcohol dehydrogenase, for instance to optimize acetaldehyde accumulation in the yeast cell.

If used in a method of screening for heterologous enzymes according to a method of the invention, the yeast cell comprises a deletion of at least one gene of the (PDH) by-pass, selected from the genes encoding the enzymes pyruvate decarboxylase (PDC), acetaldehyde dehydrogenase (ALD), and acetyl-CoA synthetase (ACS), preferably acetyl-CoA synthetase, most preferably acs2.

Figure 2:
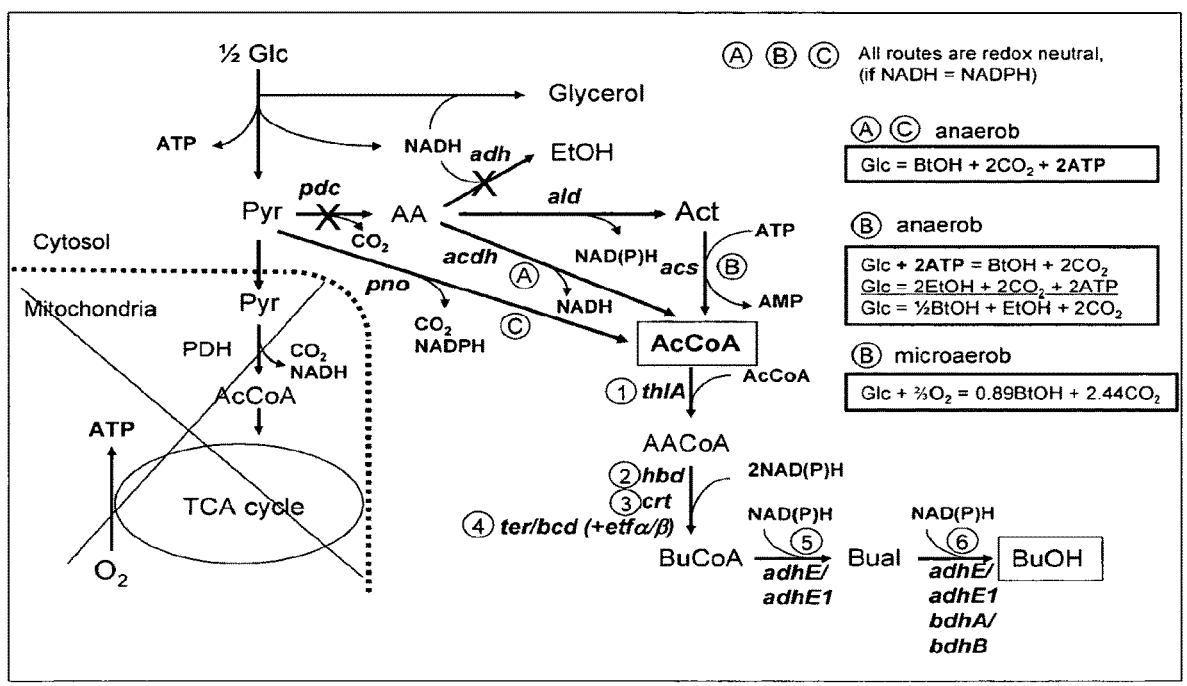
FIG. 2 shows a schematic metabolic route for butanol production in *Saccharomyces cerevisiae*. Reactions 1-6 are the butanol biosynthesis steps from *Clostridium acetobutylicum* introduced in yeast. A, B, and C indicate alternative reactions for acetyl-CoA biosynthesis in the cytosol. B indicates part of the pyruvate dehydrogenase by-pass (pdc, ald and acs), the natural source of cytosolic acetyl-CoA in yeast. Glc, glucose; EtOH, ethanol; Pyr, Pyruvate; AA, acetaldehyde; ACT, acetate; AcCoA, acetyl-CoA; AACoA, acetoacetyl-CoA; BuCoA, butyryl-CoA; Bual, butylaldehyde; BuOH, butanol; NAD(P)(H), nicotinamide adenine dinucleotide (phosphate) (in reduced form); ATP, adenosine triphosphate; AMP, adenosine monophosphate; TCA cycle, tricarboxylic acid cycle; PDH, pyruvate dehydrogenase; pdc, pyruvate decarboxylase; adh, alcohol dehydrogenase; acdh, acetylating acetaldehyde dehydrogenase; ald, acetaldehyde dehydrogenase; acs, acetyl-CoA synthetase; pno, pyruvate:NADP oxidoreductase. Enzymatic conversions indicated by reaction 1-6 indicate a heterologous butanol pathway from *Clostridium acetobutylicum*: thlB (or ThL) encoding acetyl-CoA acetyltransferase or thiolase [E.C. 2.3.1.9] (SEQ ID NO:30); hbd, 3-hydroxybutyryl-CoA dehydrogenase [E.C.1.1.1.157] (SEQ ID NO:31); crt, 3-hydroxybutyryl-CoA dehydratase [E.C.4.2.1.55] (SEQ ID NO:32); ter, trans-enoyl CoA reductase; bcd, butyryl-CoA dehydrogenase [E.C.1.3.99.2] (SEQ ID NO:33); etf αβ, heterodimeric electron transfer flavoprotein (etf α and elf β, SEQ ID NO:38 and SEQ ID NO:39, respectively); adhE/ adhE1, aldehyde/alcohol dehydrogenase E and E1 [E.C. 1.1.1.1/1.2.1.10] (SEQ ID NO:34 and 35, respectively); bdhA/bdhB, NAD(P)H-dependent butanol dehydrogenase A and B [E.C.:1.1.1.-] (SEQ ID NO:36 and 37, respectively).
Figure 3:
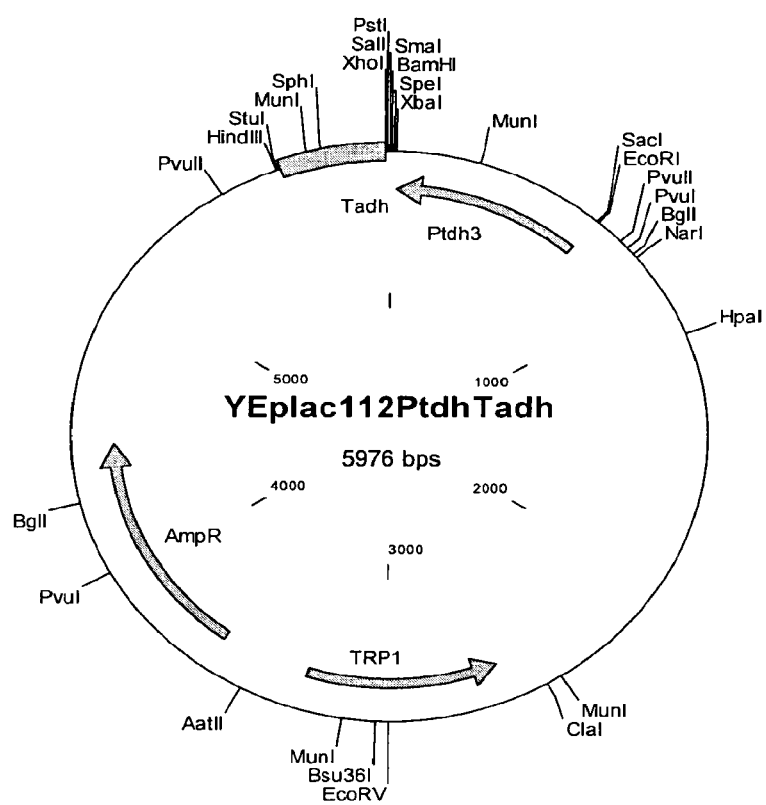
FIG. 3 shows the map of plasmid YEplac112PtdhTadh. The sequence of this plasmid is provided in SEQ ID NO:40.

If used in a method of producing a fermentation product, the yeast cell may optionally comprise a number of (heterologous) gene supplementations supporting the metabolic pathway from acetyl-CoA to said butanol. Such a pathway may consist only of heterologous gene products, or may make use of a mixture of heterologous and endogenous gene products. In the event the fermentation product is butanol, use can be made of a yeast comprising genes encoding enzymes for the butanol pathway of e.g. *Clostridium acetobutylicum* as described herein and in FIG. 2. In the event the yeast cell according to the present invention comprises genes encoding enzymes for butanol production, the yeast preferably comprises a nucleotide sequence encoding a butyryl-CoA dehydrogenase and at least one nucleotide sequence encoding a heterologous electron transfer flavoprotein (ETF). It was found that a yeast cell comprising an ETF in addition to genes of the butanol pathway produces an increased amount of butanol, A heterologous electron transfer flavoprotein in the eukaryotic cell according to the present invention may be a single protein or the ETF may comprise two or more subunits, for instance an alpha and a beta subunit. Preferably the ETF comprises an ETF alpha (SEQ ID NO: 38) and an ETF beta (SEQ ID NO: 39). The electron transfer flavoprotein may be derived from any suitable origin. Preferably, the ETF is derived from the same origin as the butyryl-CoA dehydrogenase. Preferably, the ETF is derived from prokaryotic origin preferably from a *Clostridium* sp., preferably a *Clostridium acetobutylicum* or a *Clostridium beijerinckii*.

A method for producing a fermentation product according to the present invention, preferably comprises growing a yeast under anaerobic conditions on a suitable carbon and energy source. Suitable sources of carbon and energy are C5 and C6 sugars (monosaccharides) such as glucose and polysaccharides such as starch. Other raw materials such as sugarcane, maize, wheat, barley, sugarbeets, rapeseed, and sunflower are also suitable. In some instances the raw material may be pre-digested by enzymatic treatment. Most preferably the carbon source is lignocellulose, which is composed of mainly cellulose, hemicellulose, pectin, and lignin. Lignocellulose is found, for example, in the stems, leaves, hulls, husks, and cobs of plants. Hydrolysis of these polymers by specific enzymatic treatment releases a mixture of neutral sugars including glucose, xylose, mannose, galactose, and arabinose. Lignocellulosic materials, such as wood, herbaceous material, agricultural residues, corn fiber, waste paper, pulp and paper mill residues can be used to produce butanol. Hydrolysing enzymes are for instance beta-linked glucans for the hydrolysis of cellulose (these enzymes include endoglucanases, cellobiohydrolases, glucohydrolases and beta-glucosidases); beta-glucosidases hydrolyze cellobiose; endo-acting and exo-acting hemicellulases and cellobiases for hydrolysis of hemicellulose, and acetylesterases and esterases that hydrolyze lignin glycoside bonds. These and other methods for hydrolysis of lignocellulose are well known in the art.

Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

The invention will now be illustrated by way of the following non-limiting examples.

EXAMPLES

The following examples illustrate the provision of a strain of *Saccharomyces cerevisiae* useful in assays and methods of the present invention, for instance in methods for identifying heterologous enzymes capable of forming cytosolic acetyl-CoA in *S. cerevisiae*. Such methods are useful in the identification of routes/enzymes which allow the cytosolic supply of acetyl-CoA in *S. cerevisiae* under anaerobic conditions.

In order to enhance cytosolic acetyl-CoA formation in our butanol production strain, a selection method was set up to identify heterologous enzymes forming cytosolic acetyl-CoA in *S. cerevisiae*. The test system is based on a delta acs2 yeast mutant deficient in cytosolic acetyl-CoA biosynthesis on glucose, such a strain is unable to grow on glucose as sole carbon source unless cytosolic acetyl-CoA formation is complemented. Complementation studies in such a strain can reveal which heterologous enzymes are suitable for use in butanol producing strains of *Saccharomyces cerevisiae*.

Acetylating acetaldehyde dehydrogenase was identified to be a good candidate for cytosolic acetyl-CoA supply over the homologous PDH by-pass because no ATP is dissipated. Twelve putative acetylating acetaldehyde dehydrogenases, identified based on sequence homology, were synthesized and checked for complementation of the delta acs2 yeast.

The codon pair optimized genes of the eutE homologues of *E. coli*, *L. innocua* and *C. kluyveri* and the adhE homologue of *S. aureus* were able to complement the acs2 yeast mutants (4 out of 7), resulting in growth of the acs2Δ *S. cerevisiae* host. The aim is to improve butanol biosynthesis in yeast by expression of one or more genes so identified.

In order to test if these heterologous routes for cytosolic acetyl-CoA supply work in *S. cerevisiae*, a screening system was developed based on *Saccharomyces cerevisiae* mutants carrying a deletion of the acs2 gene. These cells are not able to grow on glucose as sole carbon source unless the delta acs2 mutant is complemented with a plasmid based acs gene or complemented with the expression of any other gene generating sufficient cytosolic acetyl-CoA. So if it were to be transformed with a plasmid leading to active expression of acdh or pno, such a mutant should be able to grow again with glucose as single carbon source. The complementation studies were performed on plates. The following experiments were performed to set up and evaluate the test system.

Example 1

Construction of Delta acs2 Strain

The *S. cerevisiae* acs2 deleted strain (acs2Δ, strain) was produced by first performing a PCR on plasmid pUG6 (Güldener et al., 1996, supra) with the following oligonucleotides:

```
5'acs2::Kanlox
5'-tacacaaacagaatacaggaaagtaaatcaatacaataataaaacagctgaagcttcgtacgc-3'

3'acs2::Kanlox
5'-tctcattacgaaattttctcatttaagttatttctttttttgaggcataggccactagtggatctg-3'.
```

The resulting 1.4 kb fragment, containing the KanMX marker which confers resistance to G418, was used to transform *S. cerevisiae* CEN.PK113-3C (MATA trp1-289). After transformation the strain was plated on YPD (10 g 0 yeast extract (BD Difco), 20 g $l^{-1}$ peptone (BD Difco)), 10 g $l^{-1}$ glucose) with 200 mg/ml Geneticin (G418). In resistant transformants, correct integration was verified by PCR using oligonucleotides:
5'ACS2: 5'-gatattcggtagccgattcc-3' (SEQ ID NO: 3)
3'ACS2: 5'-ccgtaaccttctcgtaatgc-3' (SEQ ID NO: 4)
ACS2internal: 5'-cggattcgtcatcagcttca-3' (SEQ ID NO: 5)
KanA: 5'-cgcacgtcaagactgtcaag-3' (SEQ ID NO: 6)
KanB: 5'-tcgtatgtgaatgctggtcg-3' (SEQ ID NO: 7)
The phenotype was verified by testing for growth on YP with 1% glucose (YPD) or 1% ethanol+1% glycerol (YPEG) as the carbon source.

One transformant that had the correct PCR bands and did not grow on YP with glucose, but did grow on with YP with ethanol and glycerol as the carbon sources, was picked and named RWB060 (MA TA trp1-289 acs2::Kanlox).

Example 2

In Silico Identification of Putative Acetylating Acetaldehyde Dehydrogenases for Direct Conversion of Acetaldehyde to Acetyl-CoA Enzymes described for the conversion of acetaldehyde to acetyl-CoA are the so-called acetylating acetaldehyde dehydrogenases (ACDH) (E.C. 1.2.1.10) catalysing the following reaction:

Acetaldehyde(AA)+NAD$^+$+CoA<=>Acetyl-CoA+ NADH+H$^+$

From literature four types of proteins have been described that have this activity:

1) Bifunctional proteins that catalyze the reversible conversion of acetyl-CoA to acetaldehyde, and the subsequent reversible conversion of acetaldehyde to ethanol. An example of this type of proteins is the AdhE protein in *E. coli* (GenBank No: NP_415757). AdhE appears to be the evolutionary product of a gene fusion. The NH$_2$-terminal region of the AdhE protein is highly homologous to aldehyde:NAD$^+$ oxidoreductases, whereas the COOH-terminal region is homologous to a family of Fe$^{2+}$-dependent ethanol:NAD$^+$ oxidoreductases (Membrillo-Hernández et al., (2000) J. Biol. Chem. 275: 33869-33875). The *E. coli* AdhE is subject to metal-catalyzed oxidation and therefore oxygen-sensitive (Tamarit et al. (1998) J. Biol. Chem. 273:3027-32).

2) Proteins that catalyze the reversible conversion of acetyl-CoA to acetaldehyde in strictly or facultative anaerobic micro-organisms but do not possess alcohol dehydrogenase activity. An example of this type of proteins has been reported in *Clostridium kluyveri* (Smith et al. (1980) Arch. Biochem. Biophys. 203: 663-675). An acetylating acetaldehyde dehydrogenase has been annotated in the genome of *Clostridium kluyveri* DSM 555 (GenBank No: EDK33116). A homologous protein AcdH is identified in the genome of *Lactobacillus plantarum* (GenBank No: NP_784141). Another example of this type of proteins is the ald gene product in *Clostridium beijerinckii* NRRL B593 (Toth et al. (1999) Appl. Environ. Microbiol. 65: 4973-4980, GenBank No: AAD31841).

3) Proteins that are involved in ethanolamine catabolism. Ethanolamine can be utilized both as carbon and nitrogen source by many enterobacteria (Stojiljkovic et al. (1995) J. Bacteriol. 177: 1357-1366). Ethanolamine is first converted by ethanolamine ammonia lyase to ammonia and acetaldehyde, subsequently, acetaldehyde is converted by acetylating acetaldehyde dehydrogenase to acetyl-CoA. An example of this type of acetylating acetaldehyde dehydrogenase is the EutE protein in *Salmonella typhimurium* (Stojiljkovic et al. (1995) J. Bacteriol. 177: 1357-1366, GenBank No: AAL21357). *E. coli* is also able to utilize ethanolamine (Scarlett et al. (1976) J. Gen. Microbiol. 95:173-176) and has an EutE protein (GenBank No: AAG57564) which is homologous to the EutE protein in *S. typhimurium*.

4) Proteins that are part of a bifunctional aldolase-dehydrogenase complex involved in 4-hydroxy-2-ketovalerate catabolism. Such bifunctional enzymes catalyze the final two steps of the meta-cleavage pathway for catechol, an intermediate in many bacterial species in the degradation of phenols, toluates, naphthalene, biphenyls and other aromatic compounds (Powlowski and Shingler (1994) Biodegradation 5, 219-236). 4-Hydroxy-2-ketovalerate is first converted by 4-hydroxy-2-ketovalerate aldolase to pyruvate and acetaldehyde, subsequently acetaldehyde is converted by acetylating acetaldehyde dehydrogenase to acetyl-CoA. An example of this type of acetylating acetaldehyde dehydrogenase is the DmpF protein in *Pseudomonas* sp CF600 (GenBank No: CAA43226) (Shingler et al. (1992) J. Bacteriol. 174:711-24). *E. coli* has a homologous MphF protein (Ferrández et al. (1997) J. Bacteriol. 179: 2573-2581, GenBank No: NP_414885) to the DmpF protein in *Pseudomonas* sp. CF600.

Figure 4:
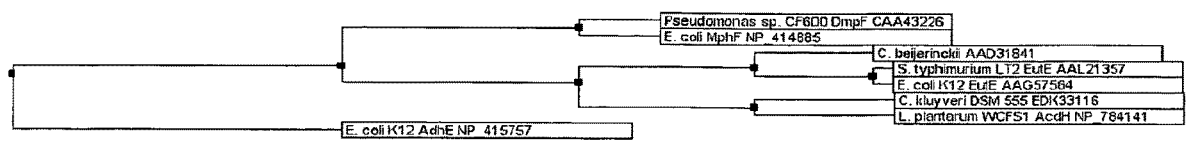
FIG. 4 shows an example of a similarity tree based on amino acid sequences of proteins of the types 1 to 4 as described in Example 2 and indicates the branches.

To identify the protein family members of acetylating acetaldehyde dehydrogenase, the amino acid sequences of the *E. coli* bifunctional AdhE protein (GenBank No: NP_415757), *L. plantarum* AcdH protein (acetylating) (GenBank No: NP_784141), the *E. coli* EutE protein (GenBank No: AAG57564) and the *E. coli* MhpF protein (GenBank No: NP_414885) were each run as a query sequence in a BLASTp search against the GenBank non-redundant protein database using default parameters. Amino acid sequences with an E-value smaller or equal to 1e-20 were extracted. Redundant sequences were removed and the remaining sequences were aligned and a similarity tree was built using Genedata Physolopher protein analyzer software, version 6.5.2. A similarity tree provides information on organism sequence similarity. The tree is created independently of the ClustalW algorithm by pairwise comparison of the amino acid sequences per residue position. At each position, the similarity is rated and summed up to an overall score for each sequence pair. Based on these pairwise scores a hierarchical clustering is performed, which arranges the sequences in a tree. Note that the ald gene product of *C. beijerinckii* (GenBank no: AAD31841) clustered together with the EutE proteins from *E. coli* and *S. typhimurium*. From this similarity tree four major branches could be defined, each branch contains one amino acid sequence that was used as a query for the BLASTp search. FIG. 4 shows an example of such a similarity tree, containing all sequences that are mentioned in this example.

At least one amino acid sequence was selected from each branch for complementation tests in *S. cerevisiae* delta acs2. Preferably, the selected amino acid sequences have experimental evidence of its biochemical function as acetylating acetaldehyde dehydrogenase. Such evidences can be found in public databases, such as in the BRENDA, UniProt and NCBI Entrez databases.

Example 3

Construction of Expression Plasmids and Complementation Test

To test whether acetylating acetaldehyde dehydrogenases (ACDH) could complement the deletion of ACS2 in *S. cerevisiae*, several genes coding for a (putative) ACDH were chosen from a variety of databases as described above.

To achieve optimal expression in yeast, the codon usage of all genes was adapted by codon pair optimization. These sequences were synthesized at Geneart AG (Regensburg, Germany).

The optimized sequences were cloned into the high copy yeast expression plasmid YEplac112PtdhTadh (SEQ ID NO:40; based on YEplac112 (2μ TRP1) (Gietz & Sugino [1988] Gene 74(2):527-34), allowing constitutive expression from the TDH3 promoter.

YEplac112PtdhTadh was made by cloning a KpnI-SacI fragment from p426GPD (Mumberg et al. [1995] Gene. 156(1):119-22), containing the TDH3 promoter and CYC1 terminator, into YEplac112 cut with KpnI-SacI. The resulting plasmid was cut with KpnI and SphI and the ends were made blunt then ligated to give YEplac112TDH. To obtain YEplac112PtdhTadh, YEplac112TDH was cut with PstI-HindIII and ligated to a 345 bp PstI-HindIII PCR fragment containing the ADH1 terminator (Tadh), thus replacing the CYC1 terminator and changing the polylinker between the promoter and terminator. The Tadh PCR fragment was generated using the following oligonucleotides:

MCS-5'Tadh: 5'-aaggtacctcta-gactagtcccgggctgcagtcgactcgagcgaatttcttatgatttatgatt-3' (SEQ ID NO: 8)

Tadh1-Hind: 5'-aggaag cttaggcctgtgtggaagaacgattacaacagg-3' (SEQ ID NO: 9)

PCR was done with VENT® DNA polymerase, according to the manufacturer's specifications.

The synthetic constructs containing the ACDH genes were cut with SpeI-PstI and ligated into YEplac112PtdhTadh digested with the same enzymes, resulting in pBOL058 through to pBOL068 and pBOL082. The names of the final plasmids and the genes they contain are given in Table 1.

Table 1: Overview on putative acetylating acetaldehyde dehydrogenases tested for complementation of delta acs2 S. cerevisiae strain. Genes which resulted in complementation are given in bold. SEQ ID NOs are provided for the DNA sequence of the wild type gene, the protein expressed therefrom, and the codon pair optimized DNA sequence.

TABLE 1

| Organisms | Name | Group* | Size (kb) | SEQ ID NO. DNA/PRT/OPT |
|---|---|---|---|---|
| Escherichia coli | adhE | 1 | 2.6 | |
| Entamoeba histolytica | adh2 | 1 | 2.6 | 48/50/49 |
| Staphylococcus aureus | adhE | 1 | 2.6 | 27/28/29 |
| Piromyces sp.E2 | adhE | 1 | 2.6 | 51/52 |
| Clostridium kluyveri | EDK33116 | 2 | 1.5 | 24/25/26 |
| Lactobacillus plantarum | acdH | 2 | 1.4 | |
| Escherichia coli | EutE | 3 | 1.4 | 18/19/20 |
| Listeria innocua | Lin1129 | 3 | 1.4 | 21/22/23 |
| Pseudomonas putida | YP 001268189 | 4 | 1.0 | |

*Group refers to the group of proteins having ACDH activity as defined in Example 2. Group 1: similar to bifunctional E. coli AdhE (AdhE-type of proteins); group 2: proteins having similarity to Lactobacillus plantarum AcdH (AcdH-type of proteins); group 3: similar to E. coli EutE (EutE-type of proteins); group 4: similar to E. coli MhpF (MhpF-type of proteins).

All plasmids were used to transform the delta acs2 yeast strain RWB060. As negative control, the empty vector YEplac112 was used. Transformants were plated on mineral medium (Verduyn et al. [1992] Yeast 8 (1992), pp. 501-517) containing either 1% glucose (MYD) or 1% ethanol+1% glycerol (MYEG) as single carbon source.

While for all constructs several transformants could be selected on minimal medium with ethanol/glycerol, this was not the case on the glucose containing plates.

TABLE 2

Result of a complementation experiment for putative acetylating acetaldehyde dehydrogenases in delta acs2 S. cerevisiae strain RWB060. Genes resulting in complementation are given in bold. MYEG and MYD columns indicate number of transformants on plates MYEG (ethanol/glycerol) and MYG (glucose).

| Organisms | Gene (GenPept accession) | plasmid | MYEG | MYD |
|---|---|---|---|---|
| | none | YEplac112 | 75 | 0 |
| Escherichia coli | adhE | pBOL059 | 6 | 0 |
| Entamoeba histolytica | adh2 | pBOL061 | 54 | 0 |
| Staphylococcus aureus | adhE (BAB41363) | pBOL064 | 36 | 39 |
| Piromyces sp.E2 | adhE | pBOL139 | 32 | 3 |
| Clostridium kluyveri | EDK33116 (EDK33116) | pBOL065 | 21 | 8 |
| Lactobacillus plantarum | acdH | pBOL058 | 6 | 0 |
| Escherichia coli | EutE (ABV06849) | pBOL066 | 24 | 18 |
| Listeria innocua | Lin1129 (CAC96360) | pBOL067 | 28 | 8 |
| Pseudomonas putida | YP 001268189 | pBOL068 | 32 | 0 |

On the glucose containing plates, transformants could only be selected for plasmids pBOL064, pBOL065, pBOL066, and pBOL067, not the empty vector. There was also a clear difference in colony size, depending on the plasmid used. While construct pBOL066 (E. coli eutE) resulted in biggest colonies, colonies of pBOL067 (L. innocua lin1129) appeared a bit smaller and pBOL065 (C. kluyveri edk3116) showed smallest colonies. Plasmid pBOL064 (S. aureus adhE) and plasmid pBOL139 (Piromyces sp. E2, adhE) were done at a later date, so could not be compared directly, Colonies containing pBOL64 seemed to be similar to colonies comprising pBOL066 and colonies comprising pBOL139 seemed to be similar to colonies comprising pBOL065.

To ensure that these results did not arise from spontaneous revertants, transformation experiments were repeated for some of the plasmids, giving the same results. In addition, for almost all plasmids four transformants were selected at random from the MYEG plates and restreaked onto MYD and MYEG plates.

In all experiments no growth was ever seen on glucose with the empty vector (YEplac112), while only pBOL065, pBOL066 and pBOL067 repeatedly gave good growth on glucose. Plasmid pBOL064 was not re-tested this way after the initial very positive result.

From these results, it was concluded that the codon pair optimized genes of the eutE homologues of:
- E. coli (SEQ ID NO:20) encoding the ethanolamine utilization protein EutE from E. coli HS;
- L. innocua (SEQ ID NO:23) encoding a hypothetical protein from L. innocua similar to ethanolamine utilization protein EutE, and
- C. kluyveri (SEQ ID NO:26) encoding acetylating acetaldehyde dehydrogenase in Clostridium kluyveri DSM 555;

and the codon pair optimized gene of the adhE homologue of
- S. aureus (SEQ ID NO:29) encoding a bifunctional acetaldehyde/alcohol dehydrogenase in Staphylococcus aureus subsp. aureus N315;

and the non codon pair optimized gene of the adhE homologue
- Piromyces sp. E2 (SEQ ID NO:51) encoding a bifunctional acetaldehyde/alcohol dehydrogenase are able to complement the acs2 yeast mutants. These genes encode an enzymatic activity allowing the formation of cytosolic acetyl-CoA from acetaldehyde in yeast.

CONCLUSIONS

The supply of cytosolic acetyl-CoA is believed to be a bottleneck in the butanol production in yeast. In order to identify heterologous genes encoding for enzymes forming cytosolic acetyl-CoA in S. cerevisiae a test system based on a delta acs2 yeast mutant was established.

Due to its deficiency in cytosolic acetyl-CoA biosynthesis on glucose, the acs2Δ strain is unable to grow with glucose as sole carbon source.

9 putative acetylating acetaldehyde dehydrogenases identified as candidates for cytosolic acetyl-CoA supply from acetaldehyde were expressed in the acs2Δ yeast. In total, 5 of these 9 genes complemented growth of the acs2Δ strain with glucose as single carbon source. Therewith, the use of the delta acs2 strain as pre-selection tool for feasible routes for cytosolic supply of acetyl-CoA was shown.

4 of 5 acetylating acetaldehyde dehydrogenases identified thus far, eutE homologues of E. coli, L. innocua and C. kluyveri and the adhE homologue of S. aureus, and Piromyces sp. E2, were successfully integrated in butanol producing strains of S. cerevisiae. The effect on butanol production was investigated as described in Examples below.

This test system may also be used, to analyse whether pyruvate:NADP oxidoreductase can successfully be overexpressed in yeast. Due to the oxygen sensitivity, this test has to be performed anaerobically.

Examples 4-6 below describe the testing 4 of the 5 selected ACDH genes from Example 3 for improvement of butanol production.

Example 4

Construction of a Butanol Producing Yeast Strain and Knocking Out the ADH1 and ADH2 Genes The six Clostridium acetobutylicum genes involved in butanol biosynthesis from Acetyl-CoA are listed in Table 3. The genes were codon pair optimized for S. cerevisiae as described in WO2008/000632 and expressed from yeast promoters and terminators as listed in Table 3.

Two yeast integration vectors (pBOL34 [SEQ ID NO:41] and pBOL36 [SEQ ID NO:42]), each containing 3 of the six codon pair optimised genes from Clostridium acetobutylicum involved in butanol biosynthesis, were designed and synthesized at Geneart.

The genes ThiL, Hbd and Crt are expressed from pBOL34 containing a AmdS selection marker. The final three genes, Bcd, BdhB and AdhE were expressed from a integration vector with an AmdS selection marker named pBOL36.

TABLE 3

Genes used for butanol production in S. cerevisiae including the promoter (1000 bp) and terminator (500 bp)

| Gene | activity | Promotor | Terminator |
|---|---|---|---|
| ThiT, | acetyl CoA c-acetyltransfrase [E.C. 2.3.1.9 | ADH1 | TDH1 |
| Hbd | 3-hydroxybutyryl-CoA dehydrogenase [E.C.1.1.1.157] | ENO1 | PMA1 |

TABLE 3-continued

Genes used for butanol production in S. cerevisiae including the promoter (1000 bp) and terminator (500 bp)

| Gene | activity | Promotor | Terminator |
|---|---|---|---|
| Crt | 3-hydroxybutyryl-CoA dehydratase [E.C.4.2.1.55] | TDH1 | ADH1 |
| Bcd | butyryl-CoA dehydrogenase [E.C.1.3.99.2], | PDC1 | TDH1 |
| BdhB | NADH-dependent butanol dehydrogenase [E.C.1.1.1.—], | ENO1 | PMA1 |
| adhE | alcohol/acetaldehyde CoA dehydrogenase [E.C.: 1.1.1.1/ 1.2.1.10] | TDH1 | ADH2 |

For integration in the ADH2 locus, pBOL36 was linearized by a BsaBI digestion. S. cerevisiae CEN.PK113-5D (MATa MAL2-8c SUC2 ura3-52) was transformed with the linear fragment and grown on plates with YCB (Difco) and 5 mM acetamide as nitrogen source.

The AmdS marker was removed by recombination by growing the transformants for 6 hours in YEPD in 2 ml tubes at 30° C. Cells were subsequently plated on 1.8% agar medium containing YCB (Difco) and 40 mM fluoracetamide and 30 mM phosphate buffer pH 6.8 supporting growth only from cells that have lost the AmdS marker. Correct integration and recombination were confirmed by PCR. The correct integration of the fragment upstream was confirmed with the following primers:

P1: 5'-GAATTGAAGGATATCTACATCAAG-3' (SEQ ID NO: 10) and

P2: 5'-CCCATCTACGGAACCCTGATCAAGC-3' (SEQ ID NO: 11).

The correct integration of the fragment downstream was confirmed with the following primers:

P3: 5'-GATGGTGTCACCATTACCAGGTCTAG-3' (SEQ ID NO: 12) and

P4: 5'-GTTCTCTGGTCAAGTTGAAGTCCA TTTTGA TTGA TTTGACTGTGTTA TTTTGCGTG-3' (SEQ ID NO: 13).

The resulting strain was named BLT021.

pBOL34 was linearized by a PsiI digestion and integrated in the ADH1 locus of BLT021. The transformants were grown on plates containing YCB (Difco) and 5 mM acetamide. For removal of the AmdS selection marker, colonies were inoculated in YEPD and grown for 6 hours in 2 ml tubes at 30° C. The cells were plated on YCB (Difco) and 40 mM fluoracetamide and 0.1% ammonium sulphate.

Correct integration and recombination were confirmed by PCR. The correct integration of the fragment upstream was confirmed with the following primer set:

P5: 5'-GAACAAT AGAGCGACCA TGACCTTG-3' (SEQ ID NO: 14) and

P6: 5'-GACATCAGCGTCACCAGCCTTGATG-3' (SEQ ID NO: 15).

The correct integration of the fragment downstream was confirmed with the following primer set:

P7: 5'-GATTGAAGGTTTCAAGAACAGGTGATG-3' (SEQ ID NO: 16) and

P8: 5'-GGCGA TCAGAGTTGAAAAAAAAA TG-3' (SEQ ID NO: 17).

The resulting strain was named BLT057.

Example 5

Introducing ETFα and ETFβ in BLT057

The ETF genes and the Acdh genes as listed in Table 4 were codon pair optimized for S. cerevisiae as described in WO2008/000632 and expressed from yeast promoters and terminators as listed in Table 4.

TABLE 4

Promoters and terminators used for expression of codon pair optimized ETF genes and Acdh genes in *S. cerevisiae*

|  | Promotor | Terminator |
|---|---|---|
| Etfα(CpO) | tef1 | tdh2 |
| Etfβ(CpO) | tdh2 | tef1 |
| Acdh64 (AdhE S. aureus) | tdh3 | adh |
| Acdh65 (Clostridium) | tdh3 | adh |
| Acdh66 (EutE E. coli) | tdh3 | adh |
| Acdh67 (lin1129 Ec) | tdh3 | Adh |

The integration vectors expressing ETFα and ETFβ only (pBOL113, [SEQ ID NO:43]) or ETFα and ETFβ combined with Acdh64 (pBOL115, [SEQ ID NO:44]), Acdh65 (pBOL116, [SEQ ID NO:45]), Acdh66 (pBOL118, [SEQ ID NO:46]) or Acdh67 (pBOL120, [SEQ ID NO:47]) were synthesized by Geneart AG.

The vectors, pBOL113, pBOL115, pBOL116, pBOL118 and pBOL120, were linearized with StuI and integrated in the ura3-52 locus of strain BLT057.

The transformants were grown in YNB (Difco) w/o amino acids+2% galactose to select for uracil prototrophic strains. The strains derived from strain BLT057 with pBOL113/115/116/118/120 integrated in the genome were designated strains: BLT071, BLT072, BLT073, BLT074 and BLT075, respectively.

Example 6

Improved Butanol Production by Expressing Positive Acdh Genes

Strains BLT071 through BLT075 as prepared in Example 5 were grown in Verduyn medium (Verduyn et al. (1992) Yeast 8: 501-517) in which the ammonium sulphate is replaced by 2 g/l ureum and which further contains 4 wt. % galactose. Cells were grown in 100 ml shake flasks containing 50 ml of medium for 72 hours at 30° C. at 180 rpm in a rotary shaker.

The butanol concentration was determined in the supernatant of the culture. Samples were analysed on a HS-GC equipped with a flame ionisation detector and an automatic injection system. Column J&W DB-1 length 30 m, id 0.53 mm, df 5 µm. The following conditions were used: helium as carrier gas with a flow rate of 5 ml/min. Column temperature was set at 110° C. The injector was set at 140° C. and the detector performed at 300° C. The data was obtained using Chromeleon software. Samples were heated at 60° C. for 20 min in the headspace sampler. One (1) ml of the headspace volatiles were automatically injected on the column.

1-Butanol production of the various strains was as follows:
BLT057: 120 mg/l
BLT071: 450 mg/l
BLT072: 500 mg/l
BLT073: 600 mg/l
BLT074: 670 mg/l
BLT075: 700 mg/l The results show that introduction of electron transfer flavoproteins (ETF alpha and ETF beta) and/or introduction of acetylating acetaldehyde dehydrogenases as identified by a complementation assay of Example 3, increase the butanol production level.

The invention claimed is:

1. A recombinant yeast cell comprising a heterologous nucleotide sequence encoding a polypeptide having enzymatic activity for the direct conversion of acetaldehyde into acetyl-CoA in the cytosol of said yeast cell wherein the polypeptide is an acetylating acetaldehyde dehydrogenase (EC 1.2.1.10), wherein said polypeptide has at least 70% sequence identity with at least one amino acid sequence selected from the group consisting of SEQ ID NOs: 19, 22, 25, and 28.

2. The recombinant yeast cell of claim 1, comprising a vector for the expression of the heterologous polypeptide in yeast, said vector comprising a heterologous nucleotide sequence operably linked to a promoter functional in yeast.

3. The recombinant yeast cell according to claim 1, further comprising an inactivation of at least one gene of the pyruvate dehydrogenase (PDH) by-pass, selected from the group consisting of genes encoding the enzymes pyruvate decarboxylase (PDC; EC 4.1.1.1), acetaldehyde dehydrogenase (ALD; EC 1.2.1.3, EC 1.2.1.4, or EC 1.2.1.5), and acetyl-CoA synthetase (ACS; EC 6.2.1.1).

4. The recombinant yeast cell according to claim 1, wherein said yeast cell shows growth on minimal medium containing glucose as sole carbon source.

5. The recombinant yeast cell according to claim 1, further comprising an inactivation of a gene encoding an enzyme that catalyses the conversion of acetaldehyde into ethanol, optionally an alcohol dehydrogenase.

6. The recombinant yeast cell according to claim 1, further comprising one or more introduced genes encoding a recombinant pathway for the formation of 1-butanol from acetyl-CoA.

7. The recombinant yeast cell according to claim 6, wherein said one or more introduced genes encode enzymes that produce acetoacetyl-CoA, 3-hydroxybutyryl-CoA, crotonyl-CoA, butyryl-CoA, butylaldehyde and/or 1-butanol.

8. The recombinant yeast cell according to claim 1, wherein said yeast is *Saccharomyces cerevisiae*.

9. The recombinant yeast cell according to claim 1, wherein the yeast is *Saccharomyces cerevisiae*, and wherein said heterologous nucleotide sequence is codon pair optimized for expression in *Saccharomyces cerevisiae*.

10. The recombinant yeast cell according to claim 9, wherein said heterologous nucleotide sequence is selected from the group consisting of SEQ ID NOs: 20, 23, 26, and 29.

11. The recombinant yeast cell according to claim 1, wherein said yeast cell comprises an inactivation of a gene encoding an acetyl-CoA synthase.

12. The recombinant yeast cell of claim 1, wherein said polypeptide has at least 90% sequence identity with at least one amino acid sequence selected from the group consisting of SEQ ID NOs: 19, 22, 25, and 28.

13. The recombinant yeast cell of claim 1, wherein said polypeptide has at least 95% sequence identity with at least one amino acid sequence selected from the group consisting of SEQ ID NOs: 19, 22, 25, and 28.

14. A method of producing a fermentation product, comprising the steps of fermenting a suitable carbon substrate with the recombinant yeast cell according to claim 1 and recovering the fermentation product produced during said fermentation.

15. The method according to claim 14, wherein the fermentation product is butanol.

* * * * *